US00RE47761E

(19) United States
(12) Reissued Patent
Pei et al.

(10) Patent Number: US RE47,761 E
(45) Date of Reissued Patent: Dec. 10, 2019

(54) ANTI-AXL ANTIBODIES AND METHODS OF USE

(71) Applicant: Genentech, Inc., South San Francisco, CA (US)

(72) Inventors: Lin Pei, San Mateo, CA (US); Yan Wu, Foster City, CA (US); Xiaofen Ye, Foster City, CA (US)

(73) Assignee: Genentech, Inc., South San Francisco, CA (US)

(21) Appl. No.: 15/287,601

(22) Filed: Oct. 6, 2016

Related U.S. Patent Documents

Reissue of:
(64) Patent No.: 8,853,369
Issued: Oct. 7, 2014
Appl. No.: 13/708,685
Filed: Dec. 7, 2012

U.S. Applications:
(63) Continuation of application No. PCT/US2011/040825, filed on Jun. 17, 2011.

(60) Provisional application No. 61/356,508, filed on Jun. 18, 2010.

(51) Int. Cl.

| | |
|---|---|
| ***C07K 16/30*** | (2006.01) |
| ***A61K 39/395*** | (2006.01) |
| ***A61K 45/06*** | (2006.01) |
| ***C07K 16/22*** | (2006.01) |
| ***C07K 16/28*** | (2006.01) |
| *A61K 39/00* | (2006.01) |

(52) U.S. Cl.
CPC ..... *A61K 45/06* (2013.01); *A61K 39/39558* (2013.01); *C07K 16/22* (2013.01); *C07K 16/2863* (2013.01); *A61K 2039/505* (2013.01); *A61K 2039/507* (2013.01); *C07K 2317/21* (2013.01); *C07K 2317/31* (2013.01); *C07K 2317/73* (2013.01); *C07K 2317/76* (2013.01); *C07K 2317/92* (2013.01)

(58) Field of Classification Search
CPC .. A61K 95/06; A61K 39/39558; C07K 16/11; C07K 16/2863
See application file for complete search history.

(56) References Cited

U.S. PATENT DOCUMENTS

| | | | |
|---|---|---|---|
| 4,676,890 | A | 6/1987 | Segal et al. |
| 4,676,980 | A | 6/1987 | Segal et al. |
| 4,737,456 | A | 4/1988 | Weng et al. |
| 4,816,567 | A | 3/1989 | Cabilly et al. |
| 5,208,020 | A | 5/1993 | Chari et al. |
| 5,416,064 | A | 5/1995 | Chari et al. |
| 5,468,634 | A | 11/1995 | Liu |
| 5,571,894 | A | 11/1996 | Wels et al. |
| 5,591,828 | A | 1/1997 | Bosslet et al. |
| 5,624,821 | A | 4/1997 | Winter et al. |
| 5,635,483 | A | 6/1997 | Pettit et al. |
| 5,648,237 | A | 7/1997 | Carter et al. |
| 5,648,260 | A | 7/1997 | Winter et al. |
| 5,712,374 | A | 1/1998 | Kuntsmann et al. |
| 5,714,586 | A | 2/1998 | Kunstmann et al. |
| 5,731,168 | A | 3/1998 | Carter et al. |
| 5,739,116 | A | 4/1998 | Hamann et al. |
| 5,750,373 | A | 5/1998 | Garrard et al. |
| 5,767,285 | A | 6/1998 | Hamann et al. |
| 5,770,429 | A | 6/1998 | Lonberg et al. |
| 5,770,701 | A | 6/1998 | Mcgahren et al. |
| 5,770,710 | A | 6/1998 | Mcgahren et al. |
| 5,773,001 | A | 6/1998 | Hamann et al. |
| 5,780,588 | A | 7/1998 | Pettit et al. |
| 5,789,199 | A | 8/1998 | Joly et al. |
| 5,821,337 | A | 10/1998 | Carter et al. |
| 5,840,523 | A | 11/1998 | Simmons et al. |
| 5,869,046 | A | 2/1999 | Presta et al. |
| 5,877,296 | A | 3/1999 | Hamann et al. |
| 5,959,177 | A | 9/1999 | Hein et al. |
| 6,040,498 | A | 3/2000 | Stomp et al. |
| 6,075,181 | A | 6/2000 | Kucherlaopati et al. |
| 6,150,584 | A | 11/2000 | Kucherlapati et al. |
| 6,171,586 | B1 | 1/2001 | Lam et al. |
| 6,194,551 | B1 | 2/2001 | Idusogie et al. |
| 6,237,791 | B1 | 5/2001 | Beck et al. |
| 6,248,516 | B1 | 6/2001 | Winter et al. |
| 6,267,958 | B1 | 7/2001 | Andya et al. |
| 6,407,213 | B1 | 6/2002 | Carter et al. |
| 6,417,429 | B1 | 7/2002 | Hein et al. |
| 6,420,548 | B1 | 7/2002 | Vezina et al. |
| 6,602,677 | B1 | 8/2003 | Wood et al. |
| 6,602,684 | B1 | 8/2003 | Umana et al. |
| 6,630,579 | B2 | 10/2003 | Chari et al. |
| 6,737,056 | B1 | 5/2004 | Presta |
| 6,982,321 | B2 | 1/2006 | Winter |

(Continued)

FOREIGN PATENT DOCUMENTS

| | | |
|---|---|---|
| EP | 0 425 235 B1 | 9/1996 |
| EP | 1 502 603 A1 | 2/2005 |

(Continued)

OTHER PUBLICATIONS

Extended European Search Report and Search Opinion dated Mar. 2, 2017, for European Patent Application No. 15199508.1, filed on Jun. 11, 2011, 14 pages.

Brennan et al., "Preparation of bispecific antibodies by chemical recombination of monoclonal immunoglobulin G .sub.1 fragments" Science 229(4708):81-83 (Jul. 5, 1985).

Carter et al., "Humanization of an anti-p185 .sup.HER2 antibody for human cancer therapy" P Natl Acad Sci USA 89:4285-4289 (May 1992).

Chan and Chan. "Therapeutic Antibodies for Autoimmunity and Inflammation," Nature Reviews Immunology 10:301-316, (2010).

Coussens et al., "Inflammation and Cancer" *Nature* 420:860-867 (Dec. 2002).

(Continued)

*Primary Examiner* — Shri Ponnaluri
(74) *Attorney, Agent, or Firm* — Morrison & Foerster LLP

(57) ABSTRACT

The invention provides anti-Axl antibodies and methods of using the same.

21 Claims, 24 Drawing Sheets

Specification includes a Sequence Listing.

(56) References Cited

U.S. PATENT DOCUMENTS

| | | | | |
|---|---|---|---|---|
| 7,041,870 | B2 | 5/2006 | Tomizuka et al. | |
| 7,087,409 | B2 | 8/2006 | Barbas et al. | |
| 7,125,978 | B1 | 10/2006 | Vezina et al. | |
| 7,189,826 | B2 | 3/2007 | Rodman | |
| 7,214,755 | B2 | 5/2007 | Minami et al. | |
| 7,332,581 | B2 | 2/2008 | Presta | |
| 7,371,826 | B2 | 5/2008 | Presta | |
| 7,498,298 | B2 | 3/2009 | Doronina et al. | |
| 7,504,256 | B1 | 3/2009 | Ogawa et al. | |
| 7,521,541 | B2 | 4/2009 | Eigenbrot et al. | |
| 7,803,377 | B2 * | 9/2010 | Yan et al. | 424/145.1 |
| 8,313,913 | B2 | 11/2012 | Nakamura et al. | |
| 2002/0164328 | A1 | 11/2002 | Shinkawa et al. | |
| 2003/0115614 | A1 | 6/2003 | Kanda et al. | |
| 2003/0157108 | A1 | 8/2003 | Presta | |
| 2004/0093621 | A1 | 5/2004 | Shitara et al. | |
| 2004/0109865 | A1 | 6/2004 | Niwa et al. | |
| 2004/0110282 | A1 | 6/2004 | Kanda et al. | |
| 2004/0110704 | A1 | 6/2004 | Yamane et al. | |
| 2004/0132140 | A1 | 7/2004 | Satoh et al. | |
| 2005/0014934 | A1 | 1/2005 | Hinton et al. | |
| 2005/0079574 | A1 | 4/2005 | Bond | |
| 2005/0119455 | A1 | 6/2005 | Fuh et al. | |
| 2005/0123546 | A1 | 6/2005 | Umana et al. | |
| 2005/0260186 | A1 | 11/2005 | Bookbinder et al. | |
| 2005/0266000 | A1 | 12/2005 | Bond | |
| 2006/0025576 | A1 | 2/2006 | Miller et al. | |
| 2006/0104968 | A1 | 5/2006 | Bookbinder et al. | |
| 2007/0061900 | A1 | 3/2007 | Murphy et al. | |
| 2007/0117126 | A1 | 5/2007 | Sidhu et al. | |
| 2007/0134759 | A1 | 6/2007 | Nishiya et al. | |
| 2007/0160598 | A1 | 7/2007 | Dennis et al. | |
| 2007/0237764 | A1 | 10/2007 | Birtalan et al. | |
| 2007/0292936 | A1 | 12/2007 | Barthelemy et al. | |
| 2008/0069820 | A1 | 3/2008 | Fuh et al. | |
| 2008/0241884 | A1 | 10/2008 | Shitara et al. | |
| 2009/0162360 | A1 | 6/2009 | Klein et al. | |
| 2010/0150919 | A1 | 6/2010 | Appleton et al. | |
| 2011/0044984 | A1 | 2/2011 | Kitazawa et al. | |

FOREIGN PATENT DOCUMENTS

| | | | |
|---|---|---|---|
| WO | WO-93/01161 | A1 | 1/1993 |
| WO | WO-93/08829 | A1 | 5/1993 |
| WO | WO-93/16185 | A2 | 8/1993 |
| WO | WO-94/29351 | A2 | 12/1994 |
| WO | WO-97/30087 | A1 | 8/1997 |
| WO | 98/58964 | | 12/1998 |
| WO | WO-98/58964 | A1 | 12/1998 |
| WO | WO-99/22764 | A1 | 5/1999 |
| WO | WO-99/31140 | A1 | 6/1999 |
| WO | WO-99/51642 | A1 | 10/1999 |
| WO | WO-03/011878 | A2 | 2/2003 |
| WO | WO-2004/039955 | A2 | 5/2004 |
| WO | WO-2004/056312 | A2 | 7/2004 |
| WO | WO-2004/058147 | A2 | 7/2004 |
| WO | WO-2005/053742 | A1 | 6/2005 |
| WO | WO-2005/100402 | A1 | 10/2005 |
| WO | WO-2006/029879 | A2 | 3/2006 |
| WO | WO-2006/029879 | A3 | 3/2006 |
| WO | WO-2006/044908 | A2 | 4/2006 |
| WO | WO-2006/044908 | A3 | 4/2006 |
| WO | WO-2007/056470 | A2 | 5/2007 |
| WO | WO-2008/077546 | A1 | 7/2008 |
| WO | WO-2009/062690 | A1 | 5/2009 |
| WO | WO2009/063965 | A1 * | 5/2009 |
| WO | WO2011/014457 | A1 * | 2/2011 |

OTHER PUBLICATIONS

Hoogenboom and Winter, "By-passing immunisation human antibodies from synthetic repertoires of germline V .sub.H gene segments rearranged in vitro" J. Mol. Biol. 227:381-388 ( 1992).

Lode et al., "Targeted therapy with a novel enediyene antibiotic calicheamicin 0 .sup.I .sub.I effectively suppresses growth and dissemination of liver metastases in a syngeneic model of murine neuroblastoma" Cancer Res. 58:2925-2928 (Jul. 15, 1998).

Lonberg, "Human antibodies from transgenic animals" Nat Biotechnol 23(9):1117-1125 (Sep. 2005).

Okazaki et al., "Fucose depletion from human IgG1 oligosaccharide enhances binding enthalpy and association rate between IgG1 and Fyc.gamma.RIIIa" J Molec Biol 336:1239-1249.

Rudikoff et al. "Single Amino Acid Substitution Altering Antigen-Binding Specificity," Proc. Nat'l Acad. Sci. USA 1982; 79:1979-83.

Shields et al. et al., "High resolution mapping of the binding site on human IgG1 for Fc gamma Rl, Fc gamma RII, Fc gamma RIII, and FcRn and design of IgG1 variants with improved binding to the Fc gamma R" J Biol Chem 276(9):6591-6604 (Mar. 2, 2001).

Sun et al., "Coexpression of Gas6/Axl in human ovarian cancers" Oncology 66(6):450-7.

Tutt et al., "Trispecific F(ab') .sub.3 derivatives that use cooperative signalling via the TCR/CD3 complex and CD2 to activate and redirect resting cytotoxic T cells" J Immunol. 147(1):60-69 (Jul. 1, 1991).

Paul, Fundamental Immunology, 3rd Edition, 1993, pp. 292-295.*

Rudikoff et al., Proc. Nat'l Acad. Sci. USA 1982; 79:1979-83.*

Chan and Carter, Nature Reviews Immunology, 2010; 10:301-316.*

Almagro et al., "Humanization of antibodies" Frontiers in Bioscience 13:1619-1633 (Jan. 2008).

Baca et al., "Antibody humanization using monovalent phage display" J Biol Chem 272(16):10678-10684 ( 1997).

Balkwill and Mantovani, "Inflammation and cancer: back to Virchow?" Lancet 357(9255):539-45 (Feb. 17, 2001).

Balkwill, F. et al., "Smoldering and polarized inflammation in the initiation and promotion of malignant disease" Cancer Cell 7:211-217 (Mar. 2005).

Berclaz, "Estrogen dependent expression of the receptor tyrosine kinase axl in normal and malignant human breast" Ann Oncol. 12(6):819-24 (Jun. 2001).

Boerner et al., "Production of Antigen-Specific Human Monoclonal Antibodies From In Vitro—Primed Human Splenocytes" J Immunol 147(1):86-95 (Jul. 1991).

Brey et al., "Automated selection of DAB-labeled tissue for immunohistochemical quantification" J Histochem Cytochem. 51(5):575-84 (May 2003).

Bruggemann et al., "Comparison of the effector functions of human immunoglobulins using a matched set of chimeric antibodies" J EXP MED 166(5):1351-61 (Nov. 1987).

Chari et al , "Immunoconjugates containing novel maytasinoids: promising anticancer drugs" Cancer Res. 52:127-131 (Jan. 1, 1992).

Charlton Methods in Molecular Biology "14 Expression and Isolation of Recombinant Antibody Fragments in *E.coli*" B.K.C. Lo, edition, Totowa, NJ,:Humana Press vol. 248:245-54 ( 2003).

Chowdhury, "Engineering hot spots for affinity enhancement of antibodies" Methods Molec Biol 207:179-196 ( 2008).

Chung et al., "Expression of the proto-oncogene Axl in renal cell carcinoma" DNA Cell Biol. 22(8):533-40 (Aug. 2003).

Clackson et al., "Making antibody fragments using phage display libraries" Nature 352:624-628 (Aug. 15, 1991).

Clynes et al., "Fc receptors are required in passive and active immunity to melanoma" P Natl Acad Sci USA 95(2):652-656 (Jan. 1998).

Coussens, L. et al., "Inflammation and Cancer" Nature 420:860-867 (Dec. 2002).

Cragg et al., "Antibody specificity controls in vivo effector mechanisms of anti-CD20 reagents" Blood 103(7):2738-2743 ( 2004).

Cragg et al., "Complement-mediated lysis by anti-CD20 mAb correlates with segregation into lipid rafts" Blood 101(3):1045-1052 ( 2003).

Craven et al., "Receptor tyrosine kinases expressed in metastatic colon cancer" Int J Cancer 60(6):791-7 ( 1995).

Cree et al., "Methotrexate chemosensitivity by ATP luminescence in human leukemia cell lines and in breast cancer primary cultures: comparison of the TCA-100 assay with a clonogenic assay" Anticancer Drugs 6:398-404 ( 1995).

(56) References Cited

OTHER PUBLICATIONS

Crouch et al., "The use of ATP bioluminescence as a measure of cell proliferation and cytotoxicity" J Immunol Methods 160:81-88 ( 1993).
Cunningham et al., "High Resolution Epitope Mapping of hGH-Receptor Interactions by Alanine-Scanning Mutagenesis" Science 244(4908):1081-1085 (Jun. 2, 1989).
Dall'Acqua et al., "Antibody humanization by framework shuffling" Methods 36:43-60 ( 2005).
Dubowchik et al., "Doxorubicin immunoconjugates containing bivalent, lysosomally-cleavable dipeptide linkages" Bioorg Med Chem Lett 12:1529-32 ( 2002).
Duncan et al., "The binding site for Clq on IgG" Nature 322:738-740 ( 1988).
Eberhard et al., "Mutations in the epidermal growth factor receptor and in KRAS are predictive and prognostic indicators in patients with non-small-cell lung cancer treated with chemotherapy alone and in combination with erlotinib" J Clin Oncol. 23(25):5900-9 ( 2005).
Fellouse et al., "Synthetic antibodies from a four-amino-acid code: A dominant role for tyrosine in antigen recognition" P Natl Acad Sci USA 101(34):12467-12472 (Aug. 24, 2004).
Gazzano-Santoro et al., "A non-radioactive complement-dependent cytotoxicity assay for anti-CD20 monoclonal antibody" J Immunol Methods 202:163-171 ( 1997).
Gerngros, "Advances in the production of human therapeutic proteins in yeasts and filamentous fungi" Nature Biotechnology 22(11):1409-1414 (Nov. 2004).
Giaccone, "Epidermal growth factor receptor inhibitors in the treatment of non-small-cell lung cancer" J Clin Oncol. 23(14):3235-42 ( 2005).
Gjerdrum et al., "Axl is an essential epithelial-to-mesenchymal transition-induced regulator of breast cancer metastasis and patient survival" Proc Natl Acad Sci U S A 107(3):1124-9 ( 2010).
Graham et al., "Characteristics of a human cell ine transformed by DNA from human adenovirus type 5" J Gen Virol 36(1):59-72 (Jul. 1977).
Griffiths et al., "Human anti-self antibodies with high specificity from phage display libraries" EMBO J 12(2):725-734 (Feb. 1993).
Gruber et al., "Efficient tumor cell lysis mediated by a bispecific single chain antibody expressed in *Escherichia coli*" J Immunol, 152:5368-5374 ( 1994).
Guyer et al., "Immunoglobulin binding by mouse intestinal epithelial cell receptors" J Immunol 117(2):587-593 (Aug. 1976).
Haghnegahdar et al., "The tumorigenic and angiogenic effects of MGSA/GRO proteins in melanoma" J Leukoc Biol. 67(1):53-62 ( 2000).
Hellstrom et al., "Antitumor effects of L6, an IgG2a antibody that reacts with most human carcinomas" P Natl Acad Sci USA 83:7059-7063 (Sep. 1986).
Hellstrom et al., "Strong antitumor activities of IgG3 antibodies to a human melanoma-associated ganglioside" P Natl Acad Sci USA 82:1499-1502 (Mar. 1985).
Hinman et al., "Preparation and characterization of monoclonal antibody conjugates of the calicheamicins: A novel and potent family of antitumor antibiotics" Cancer Res 53:3336-3342 ( 1993).
Holland et al., "Multiple roles for the receptor tyrosine kinase axl in tumor formation" Cancer Res. 65(20):9294-303 ( 2005).
Holland et al., "R428, a selective small molecule inhibitor of Axl kinase, blocks tumor spread and prolongs survival in models of metastatic breast" Cancer Res. 70(4):1544-54 ( 2010).
Holliger et al., "'Diabodies': Small bivalent and bispecific antibody fragments" P Natl Acad Sci USA 90:6444-6448 (Jul. 1993).
Hong et al., "Receptor tyrosine kinase AXL is induced by chemotherapy drugs and overexpression of AXL confers drug resistance in acute myeloid leukemia" Cancer Lett. 268(2):314-24 ( 2008).
Hoogenboom et al., "Overview of antibody phage-display technology and its applications" Methods Mol Biol 178:1-37 ( 2002).
Hudson et al., "Engineered antibodies" Nature Medicine 9(1):129-134 (Jan. 2003).
Hutterer et al., "Axl and growth arrest-specific gene 6 are frequently overexpressed in human gliomas and predict poor prognosis in patients with glioblastoma multiforme" Clin Cancer Res. 14(1):130-8 ( 2008).
Idusogie et al., "Mapping of the C1q binding site on Rituxan, a chimeric antibody with a human IgG1 Fc" J Immunol 164:4178-4184 ( 2000).
Ito et al., "Expression of the Axl receptor tyrosine kinase in human thyroid carcinoma" Thyroid 9(6):563-7 ( 1999).
Janssen et al., "A novel putative tyrosine kinase receptor with oncogenic potential" Oncogene 6:2113-2120 ( 1991).
Jeffrey et al., "Dipeptide-based highly potent doxorubicin antibody conjugates" Bioorganic Med Chem Letters 16:358-362 ( 2006).
Kam et al., "Carbon nanotubes as multifunctional biological transporters and near-infrared agents for selective cancer cell destruction" P Natl Acad Sci USA 102(33):11600-11605 (Aug. 2005).
Kanda et al., "Comparison of cell lines for stable production of fucose-negative antibodies with enhanced ADCC" Biotechnol Bioeng 94(4):680-688 (Jul. 5, 2006).
Kashmiri et aL, "SDR grafting—a new approach to antibody humanization" Methods 36:25-34 ( 2005).
Kim et al., "Localization of the site of the murine IgG1 molecule that is involved in binding to the murine intestinal Fc receptor" Eur J Immunol 24(10):2429-2434 (Oct. 1994).
Kindt et al. Kuby Immunology "Antigens and Antibodies Chapter 4" 6th ed edition, N.Y.:W.H. Freeman and Co,:p. 91 ( 2007).
King et al., "Monoclonal antibody conjugates of doxorubicin prepared with branched peptide linkers. Inhibition of aggregation by methoxytriethyleneglycol chains" Journal of Medical Chemistry 45:4336-4343 ( 2002).
Klimka et al., "Human anti-CD30 recombinant antibodies by guided phage antibody selection using cell panning" Brit J Cancer 83(2):252-260 ( 2000).
Koorstra et al., "The Axl receptor tyrosine kinase confers an adverse prognostic influence in pancreatic cancer and represents a new therapeutic target" Cancer Biol Ther. 8(7):618-26 ( 2009).
Kostelny et al., "Formation of a bispecific antibody by the use of leucine zippers" J Immunol. 148:1547-1553 (Mar. 1, 1992).
Kozbor et al., "A human hybrid myeloma for production of human monoclonal antibodies" J Immunol 133(6):3001-3005 (Dec. 1984).
Kratz et al., "Prodrugs of anthracyclines in cancer chemotherapy" Curr Med Chem 13:477-523 ( 2006).
Lai et al., "An Extended Family of Protein-Tyrosine Kinase Genes Differentially Expressed in the Vertebrate Nervous System" Neuron 6:691-704 (May 1991).
Lee et al., "Bivalent antibody phage display mimics natural immunoglobulin" J Immunol Methods 284:119-132 ( 2004).
Lee et al., "High-affinity human antibodies from phage-displayed synthetic Fab libraries with a single framework scaffold" J Mol Biol. 340(5):1073-93 ( 2004).
Li et al., "Axl as a potential therapeutic target in cancer: role of Axl in tumor growth, metastasis and angiogcnesis" Oncogene 28:3442-3455 ( 2009).
Li et al., "Human antibodies for immunotherapy development generated via a human B cell hybridoma technology" P Natl Acad Sci USA 103(10):3557-62 (Mar. 2006).
Li et al., "Optimization of humanized IgGs in glycoengineered *Pichia pastoris*" Nat Biotechnol 24(2):210-215 (Feb. 2006).
Liang et al., "Cross-species vascular endothelial growth factor (VEGF)-blocking antibodies completely inhibit the growth of human tumor xenografts and measure the contribution of stromal VEGF" J Biol Chem 281(2):951-61 (Jan. 2006).
Liang et al., "Function blocking antibodies to neuropilin-1 generated from a designed human synthetic antibody phage library" J. Mol. Biol. 366:815-829 ( 2007).
Loges et al., "Malignant cells fuel tumor growth by educating infiltrating leukocytes to produce the mitogen Gas6" Blood 115(11):2264-73 ( 2010).
Lonberg, "Fully human antibodies from transgenic mouse and phage display platforms" Current Opin Immunol 20:450-459 ( 2008).
Yes Lonberg, "Human antibodies from transgenic animals" Nat Biotechnol 23(9):1117-1125 (Sep. 2005).

(56) References Cited

OTHER PUBLICATIONS

Mahadevan et al., "A novel tyrosine kinase switch is a mechanism of imatinib resistance in gastrointestinal stromal tumors" Oncogene 26(27):3909-19 ( 2007).
Marks and Bradbury Methods Mol Biol, Antibody Engineering "Selection of human antibodies from phage display libraries" Benny K. C. Lo,Humana Press, vol. 248:161-176 ( 2004).
Marks et al., "By-passing immunization, Human antibodies from V-gene libraries displayed on phage" J. Mol. Biol. 222:581-597 ( 1991).
Mather et al., "Culture of testicular cells in hormone-supplemented serum-free medium" Ann. NY Acad. Sci. 383:44-68 ( 1982).
Mather, "Establishment and characterization of two distinct mouse testicular epithelial cell lines" Biol. Reprod. 23:243-252 ( 1980).
McCafferty et al., "Phage Antibodies: Filamentous Phage Displaying Antibody Variable Domains" Nature 348:552-554 (Dec. 1990).
Meric et al., "Expression profile of tyrosine kinases in breast cancer" Clin Cancer Res. 8(2):361-7 ( 2002).
Millstein et al., "Hybrid hybridomas and their use in immunohistochemistry" Nature 305:537-539 ( 1983).
Morrison et al., "Chimeric human antibody molecules: Mouse antigen-binding domains with human constant region domains" P Natl Acad Sci USA 81:6851-6855 (Nov. 1984).
Mosmann, "Rapid colorimetric assay for cellular growth and survival: Application to proliferation and cytotoxicity assays" J Immunol Methods 65:55-63 ( 1983).
Nagy et al., "Stability of cytotoxic luteinizing hormone-releasing hormone conjugate (AN-152) containing doxorubicin 14-O-hemiglutarate in mouse and human serum in vitro: implications for the design of preclinical studies" P Natl Acad Sci USA 97(2):829-34 (Jan. 18, 2000).
Ni, "Research progress and future perspectives in antibodomics and antibodomic drugs" Xiandai Mianyixue ((Abstract only)), 26(4):265-168 ( 2006).
O'Bryan et al., "Axl, A Transforming Gene Isolated From Primary Human Myeloid Leukemia Cells, Encodes a Novel Receptor Tyrosine Kinase" Mol Cell Biol 11(10):5016-5031 (Oct. 1991).
Osbourn et al., "From rodent reagents to human therapeutics using antibody guided selection" Methods 36:61-68 ( 2005).
Paez et al., "EGFR Mutations in Lung Cancer: Correlation with Clinical Response to Gefitinib Therapy" Science 304:1497-1500 (Jun. 4, 2004).
Petkova et al., "Enhanced half-life of genetically engineered human IgG1 antibodies in a humanized FcRn mouse model: potential application in humorally mediated autoimmune disease" Int Immunol 18(12):1759-69 (Dec. 2006).
Pollard, J., "Tumour-educated macrophages promote tumour progression and metastasis" Nat Rev Cancer 4:71-8 (Jan. 2004).
Portolano et al., "Lack of promiscuity in autoantigen-specific H and L chain combinations as revealed by human H and L chain 'Roulette'" J Immunol 150(3):880-887 (Feb. 1993).
Presta et al., "Humanization of an antibody directed against IgE" J. Immunol. 151(5):2623-2632 (Sep. 1, 1993).
Queen et al., "A humanized antibody that binds to the interleukin 2 receptor" P Natl Acad Sci USA 86(24):10029-10033 (Dec. 1989).
Ravetch and Kinet, "Fc receptors" Annu Rev Immunol 9:457-492 ( 1991).
Reichmann et al., "Reshaping human antibodies for therapy" Nature 332:323-327 (Mar. 24, 1988).
Rikova et al., "Global survey of phosphotyrosine signaling identifies oncogenic kinases in lung cancer" Cell 131(6):1190-203 ( 2007).
Ripka et al., "Two chinese hamster ovary glycosylation mutants affected in the conversion of GDP-mannose to GDP-fucose" Arch Biochem Biophys 249(2):533-545 (Sep. 1986).
Rosok et al., "A combinatorial library strategy for the rapid humanization of anticarcinoma BR96 Fab" J Biol Chem 271(37):22611-22618 (Sep. 13, 1996).
Sainaghi et al., "Gas6 induces proliferation in prostate carcinoma cell lines expressing the Axl receptor" J Cell Physiol. 204(1):36-44 ( 2005).
Sandler et al., "Paclitaxel-carboplatin alone or with bevacizumab for non-small-cell lung cancer" New Engl J Med 355(24):2542-50 (Dec. 2006).
Shieh et al., "Expression of axl in lung adenocarcinoma and correlation with tumor progression" Neoplasia 7(12):1058-64 ( 2005).
Sidhu et al., "Phage-displayed antibody libraries of synthetic heavy chain complementarity determining regions" J Mol Biol 338:299-310 ( 2004).
Sims et al., "A Humanized CD18 Antibody Can Block Function without Cell Destruction" J. Immunol. 151(4):2296-2308 (Aug. 1993).
Sun et al., "Coexpression of Gas6/Axl in human ovarian cancers" Oncology 66(6):450-7 ( 2004).
Tai et al., "Axl promotes cell invasion by inducing MMP-9 activity through activation of NF-kappaB and Brg-1" Oncogene 27(29):4044-55 ( 2008).
Torgov et al., "Generation of an intensely potent anthracycline by a monoclonal antibody-(beta)-galactosidase conjugate" Bioconjugate Chemistry 16:717-721 ( 2005).
Traunecker et al., "Bispecific single chain molecules (Janusins) target cytotoxic lymphocytes on HIV infected cells" EMBO J 10(12):3655-3659 ( 1991).
Tsao et al., "Molecular analysis of the epidermal growth factor receptor (EGFR) gene and protein expression in patients treated with erlotinib in National Cancer Institute of Canada Clinical Trials Group trial BR.21" Meeting Anstracts, J. Clin Oncol 23:7007, (2005).
Urlaub et al., "Isolation of chinese hamster cell mutants deficient in dihydrofolate reductase activity" P Natl Acad Sci USA 77(7):4216 (Jul. 1980).
Vajkoczy et al., "Dominant-negative inhibition of the Axl receptor tyrosine kinase suppresses brain tumor cell growth and invasion and prolongs survival" Proc Natl Acad Sci U S A. 103(15):5799-804 ( 2006).
van Dijk et al., "Human antibodies as next generation therapeutics" Curr Opin Chem Biol. 5(4):368-74 ( 2001).
Vollmers and Brandlein, "Death by stress: natural IgM-induced apoptosis" Methods Find Exp Clin Pharmacol 27(3):185-191 ( 2005).
Vollmers and Brandlein, "The 'early birds': Natural IgM antibodies and immune surveillance" Histol Histopathol 20:927-937 ( 2005).
Winter et al., "Making antibodies by phage display technology" Annu. Rev. Immunol. 12:433-455 ( 1994).
Wright et al., "Effect of glycosylation on antibody function: implications for genetic engineering" Trends Biotechnol. 15(1):26-32 ( 1997).
Wu et al., "Clinical significance of AXL kinase family in gastric cancer" Anticancer Res. 22:1071-8 ( 2002).
Yamane-Ohnuki et al., "Establishment of FUT8 knockout Chinese hamster ovary cells: an ideal host cell line for producing completely defucosylated antibodies with enhanced antibody-dependent cellular cytotoxicity" Biotechnol Bioeng 87(5):614-622 (Sep. 5, 2004).
Yauch et al., "Epithelial versus mesenchymal phenotype determines in vitro sensitivity and predicts clinical activity of erlotinib in lung cancer patients" Clin Cancer Res. 11:8686-98 ( 2005).
Zhang et al., "AXL is a potential target for therapeutic intervention in breast cancer progression" Cancer Res. 68(6):1905-15 ( 2008).
Zhang et al., "Epidermal growth factor receptor-related protein inhibits cell growth and induces apoptosis of BxPC3 pancreatic cancer cells" Cancer Res 65(9):3877-3882 (May 1, 2005).
Ye et al., "An anti-Axl monoclonal antibody attenuates xenograft tumor growth and enchances the effect of multiple anticancer therapies" Oncogene 29:5254-5264 (2010).

* cited by examiner

| Clone # | H1 | | | | | | | | | | SEQ ID NO: |
|---|---|---|---|---|---|---|---|---|---|---|---|
| | 26 | 27 | 28 | 29 | 30 | 31 | 32 | 33 | 34 | 35 | |
| 327.6 | G | F | T | F | T | G | H | W | I | H | 1 |
| 327.6.S2 | G | F | S | L | S | G | S | W | I | H | 7 |
| 327.6.S11 | G | F | S | F | T | G | T | W | I | H | 13 |
| 327.6.S50 | G | F | T | F | T | G | S | W | I | H | 19 |
| 327.6.S52 | G | F | T | F | T | G | S | W | I | H | 25 |
| 327.6.S65 | G | F | T | F | T | G | S | W | I | H | 31 |
| 327.42 | G | F | T | F | T | G | T | G | I | H | 37 |
| 327.42.S8 | G | F | T | F | T | G | T | G | I | H | 43 |
| 327.42.S31 | G | F | S | F | T | S | I | G | I | H | 49 |
| 327.42.S13 | G | F | T | F | T | G | T | G | I | H | 55 |
| 327.42.S43 | G | F | S | V | R | G | T | G | L | H | 61 |
| 327.42.S52 | G | F | T | F | T | G | T | G | I | H | 67 |
| 327.42.S63 | G | F | T | F | T | G | T | G | I | H | 73 |
| 327.42.S73 | G | F | T | F | T | G | T | G | I | H | 79 |
| 327.42.H2 | G | F | T | F | T | G | T | G | I | H | 85 |
| 327.42.H4 | G | F | T | F | T | G | T | G | I | H | 91 |
| 327.42.H20 | G | F | T | F | T | G | T | G | I | H | 97 |

*FIG. 1A*

| Clone # | H2 | | | | | | | | | | | | | | | | | | SEQ ID NO: |
|---|---|---|---|---|---|---|---|---|---|---|---|---|---|---|---|---|---|---|---|
| | 49 | 50 | 51 | 52 | 52a | 53 | 54 | 55 | 56 | 57 | 58 | 59 | 60 | 61 | 62 | 63 | 64 | 65 | |
| 327.6 | G | W | I | S | P | Y | G | G | S | T | Y | Y | A | D | S | V | K | G | 2 |
| 327.6.S2 | G | W | I | N | P | Y | R | G | Y | A | Y | Y | A | D | S | V | K | G | 8 |
| 327.6.S11 | G | W | I | A | P | Y | S | R | H | P | Y | Y | A | D | S | V | K | G | 14 |
| 327.6.S50 | G | W | I | S | P | Y | G | G | S | T | Y | Y | A | D | S | V | K | G | 20 |
| 327.6.S52 | G | W | I | S | P | Y | G | G | S | T | Y | Y | A | D | S | V | K | G | 26 |
| 327.6.S65 | G | W | I | S | P | Y | G | G | S | T | Y | Y | A | D | S | V | K | G | 32 |
| 327.42 | A | G | I | S | P | A | G | G | Y | T | Y | Y | A | D | S | V | K | G | 38 |
| 327.42.S8 | A | G | I | P | P | V | G | S | Y | T | Y | Y | A | D | S | V | K | G | 44 |
| 327.42.S31 | A | G | I | P | P | V | G | R | Y | T | Y | Y | A | D | S | V | K | G | 50 |
| 327.42.S13 | A | G | I | S | P | A | G | G | Y | T | Y | Y | A | D | S | V | K | G | 56 |
| 327.42.S43 | A | G | I | S | P | V | G | G | Y | T | Y | Y | A | D | S | V | K | G | 62 |
| 327.42.S52 | A | G | I | S | P | A | G | G | Y | T | Y | Y | A | D | S | V | K | G | 68 |
| 327.42.S63 | A | G | I | S | P | A | G | G | Y | T | Y | Y | A | D | S | V | K | G | 74 |
| 327.42.S73 | A | G | I | S | P | A | G | G | Y | T | Y | Y | A | D | S | V | K | G | 80 |
| 327.42.H2 | A | G | I | S | P | A | G | G | Y | T | Y | Y | A | D | S | V | K | G | 86 |
| 327.42.H4 | A | G | I | S | P | A | G | G | Y | T | Y | Y | A | D | S | V | K | G | 92 |
| 327.42.H20 | A | G | I | S | P | A | G | G | Y | T | Y | Y | A | D | S | V | K | G | 98 |

*FIG. 1B*

| Clone # | H3 | | | | | | | | | | | | | | | | | | SEQ ID NO: |
|---|---|---|---|---|---|---|---|---|---|---|---|---|---|---|---|---|---|---|---|
| | 93 | 94 | 95 | 96 | 97 | 98 | 99 | 100 | A | B | C | D | E | F | G | H | 101 | 102 | |
| 327.6 | A | R | E | Y | S | G | W | G | G | S | S | V | G | Y | A | M | D | Y | 3 |
| 327.6.S2 | A | R | E | Y | S | G | W | G | G | S | S | V | G | Y | A | M | D | Y | 9 |
| 327.6.S11 | A | R | E | Y | S | G | W | G | G | S | S | V | G | Y | A | M | D | Y | 15 |
| 327.6.S50 | A | R | E | Y | N | D | W | R | G | S | S | V | G | Y | A | M | D | Y | 21 |
| 327.6.S52 | A | R | E | Y | S | G | W | A | S | S | Y | V | G | Y | A | M | D | Y | 27 |
| 327.6.S65 | A | R | E | Y | P | G | W | G | G | S | S | I | G | Y | E | M | D | Y | 33 |
| 327.42 | A | R | W | R | S | L | S | S | G | | | | | | | M | D | Y | 39 |
| 327.42.S8 | A | R | W | R | S | L | S | S | G | | | | | | | M | D | Y | 45 |
| 327.42.S31 | A | R | W | R | S | L | S | S | G | | | | | | | M | D | Y | 51 |
| 327.42.S13 | A | R | W | R | S | L | S | S | G | | | | | | | M | D | Y | 57 |
| 327.42.S43 | A | R | W | R | S | L | S | S | G | | | | | | | M | D | Y | 63 |
| 327.42.S52 | A | R | W | R | S | L | S | S | G | | | | | | | M | D | Y | 69 |
| 327.42.S63 | A | R | W | R | S | L | S | S | G | | | | | | | M | D | Y | 75 |
| 327.42.S73 | A | R | W | R | S | L | S | S | G | | | | | | | M | D | Y | 81 |
| 327.42.H2 | A | R | W | R | S | L | S | S | G | | | | | | | M | D | Y | 87 |
| 327.42.H4 | A | R | W | R | S | L | S | S | G | | | | | | | M | D | Y | 93 |
| 327.42.H20 | A | R | W | R | S | L | S | S | G | | | | | | | M | D | Y | 99 |

* Blank entries denote amino acid residues that are not present

FIG. 1C

| Clone # | L1 | | | | | | | | | | | SEQ ID NO: |
|---|---|---|---|---|---|---|---|---|---|---|---|---|
| | 24 | 25 | 26 | 27 | 28 | 29 | 30 | 31 | 32 | 33 | 34 | |
| 327.6 | R | A | S | Q | D | V | S | T | A | V | A | 4 |
| 327.6.S2 | R | A | S | Q | D | V | S | T | A | V | A | 10 |
| 327.6.S11 | R | A | S | Q | D | V | S | T | A | V | A | 16 |
| 327.6.S50 | R | A | S | Q | D | V | S | T | A | V | A | 22 |
| 327.6.S52 | R | A | S | Q | D | V | S | T | A | V | A | 28 |
| 327.6.S65 | R | A | S | Q | D | V | S | T | A | V | A | 34 |
| 327.42 | R | A | S | Q | D | V | S | T | A | V | A | 40 |
| 327.42.S8 | R | A | S | Q | D | V | S | T | A | V | A | 46 |
| 327.42.S31 | R | A | S | Q | D | V | S | T | A | V | A | 52 |
| 327.42.S13 | R | A | S | Q | D | V | S | T | A | V | A | 58 |
| 327.42.S43 | R | A | S | Q | D | V | S | T | A | V | A | 64 |
| 327.42.S52 | R | A | S | Q | D | V | S | T | A | V | A | 70 |
| 327.42.S63 | R | A | S | Q | D | V | S | T | A | V | A | 76 |
| 327.42.S73 | R | A | S | Q | D | V | S | T | A | V | A | 82 |
| 327.42.H2 | R | A | S | Q | I | I | G | I | S | L | A | 88 |
| 327.42.H4 | R | A | S | Q | S | I | R | N | S | L | A | 94 |
| 327.42.H20 | R | A | S | Q | I | I | G | R | S | L | A | 100 |

FIG. 1D

| Clone # | L2 | | | | | | | SEQ ID NO: |
|---|---|---|---|---|---|---|---|---|
| | 50 | 51 | 52 | 53 | 54 | 55 | 56 | |
| 327.6 | S | A | S | F | L | Y | S | 5 |
| 327.6.S2 | S | A | S | F | L | Y | S | 11 |
| 327.6.S11 | S | A | S | F | L | Y | S | 17 |
| 327.6.S50 | S | A | S | F | L | Y | S | 23 |
| 327.6.S52 | S | A | S | F | L | Y | S | 29 |
| 327.6.S65 | S | A | S | F | L | Y | S | 35 |
| 327.42 | S | A | S | F | L | Y | S | 41 |
| 327.42.S8 | S | A | S | F | L | Y | S | 47 |
| 327.42.S31 | S | A | S | F | L | Y | S | 53 |
| 327.42.S13 | S | A | S | F | L | Y | S | 59 |
| 327.42.S43 | S | A | S | F | L | Y | S | 65 |
| 327.42.S52 | S | A | S | F | L | Y | S | 71 |
| 327.42.S63 | S | A | S | F | L | Y | S | 77 |
| 327.42.S73 | S | A | S | F | L | Y | S | 83 |
| 327.42.H2 | A | A | S | N | L | A | S | 89 |
| 327.42.H4 | V | A | S | S | L | A | S | 95 |
| 327.42.H20 | V | A | S | N | L | A | S | 101 |

FIG. 1E

| Clone # | L3 | | | | | | | | | SEQ ID NO: |
|---|---|---|---|---|---|---|---|---|---|---|
| | 89 | 90 | 91 | 92 | 93 | 94 | 95 | 96 | 97 | |
| 327.6 | Q | Q | S | Y | T | T | P | P | T | 6 |
| 327.6.S2 | Q | Q | S | Y | T | T | P | P | T | 12 |
| 327.6.S11 | Q | Q | S | Y | T | T | P | P | T | 18 |
| 327.6.S50 | Q | Q | S | Y | S | N | P | Y | T | 24 |
| 327.6.S52 | Q | Q | S | Y | T | S | P | S | T | 30 |
| 327.6.S65 | Q | Q | S | Y | Y | F | R | S | T | 36 |
| 327.42 | Q | Q | S | Y | T | T | P | P | T | 42 |
| 327.42.S8 | Q | Q | S | K | T | T | P | P | T | 48 |
| 327.42.S31 | Q | Q | S | Y | M | S | P | L | T | 54 |
| 327.42.S13 | Q | Q | S | K | R | T | P | P | T | 60 |
| 327.42.S43 | Q | Q | A | K | T | T | P | P | T | 66 |
| 327.42.S52 | Q | Q | A | K | S | T | P | P | T | 72 |
| 327.42.S63 | Q | Q | A | K | R | T | P | P | T | 78 |
| 327.42.S73 | Q | Q | A | K | T | T | P | P | T | 84 |
| 327.42.H2 | Q | Q | S | Y | S | T | P | L | T | 90 |
| 327.42.H4 | Q | Q | S | Y | S | T | P | L | T | 96 |
| 327.42.H20 | Q | Q | S | N | A | T | P | P | T | 102 |

FIG. 1F

Clone YW327.6S2

VH

EVQLVESGGGLVQPGGSLRLSCAAS GFSLSGSWIH WVRQAPGKGLEWV
GWINPYRGYAYYADSVKG RFTISADTSKNTAYLQMNSLRAEDTAVYYC
AREYSGWGGSSVGYAMDY WGQGTLV (SEQ ID NO: 103)

VL

DIQMTQSPSSLSASVGDRVTITC RASQDVSTAVA WYQQKPGKAPKLLIY SASFLYS
GVPSRFSGSGSGTDFTLTISSLQPEDFATYYC QQSYTTPPT FGQGTKVEIKR
(SEQ ID NO:104)

Clone YW327.6S11

VH

EVQLVESGGGLVQPGGSLRLSCAAS GFSFTGTWIH WVRQAPGKGLEWV
GWIAPYSRHPYYADSVKG RFTISADTSKNTAYLQMNSLRAEDTAVYYC
AREYSGWGGSSVGYAMDY WGQGTLV (SEQ ID NO: 105)

VL

DIQMTQSPSSLSASVGDRVTITC RASQDVSTAVA WYQQKPGKAPKLLIY SASFLYS
GVPSRFSGSGSGTDFTLTISSLQPEDFATYYC QQSYTTPPT FGQGTKVEIKR
(SEQ ID NO: 106)

Clone YW327.42.S8

VH

EVQLVESGGGLVQPGGSLRLSCAAS GFTFTGTGIH WVRQAPGKGLEWV
AGIPPVGSYTYYADSVKG RFTISADTSKNTAYLQMNSLRAEDTAVYYC ARWRSLSSGMDY
WGQGTLV (SEQ ID NO: 107)

VL

DIQMTQSPSSLSASVGDRVTITC RASQDVSTAVA WYQQKPGKAPKLLIY SASFLYS
GVPSRFSGSGSGTDFTLTISSLQPEDFATYYC QQSKTTPPT FGQGTKVEIKR
(SEQ ID NO: 108)

Clone YW327.42.S31

VH

EVQLVESGGGLVQPGGSLRLSCAAS GFSFTSIGIH WVRQAPGKGLEWV
AGIPPVGRYTYYADSVKG RFTISADTSKNTAYLQMNSLRAEDTAVYYC ARWRSLSSGMDY
WGQGTLV (SEQ ID NO: 109)

VL

DIQMTQSPSSLSASVGDRVTITC RASQDVSTAVA WYQQKPGKAPKLLIY SASFLYS
GVPSRFSGSGSGTDFTLTISSLQPEDFATYYC QQSYMSPLT FGQGTKVEIKR
(SEQ ID NO: 110)

FIG. 2

FIG. 3A | FIG. 3B

FIG. 3

```
I
A    QVQLVQSGAEVKKPGASVKVSCKASGYTFT      -H1-      WVRQAPGQGLEWMG          -H2-      RVTIT
B    QVQLVQSGAEVKKPGASVKVSCKAS     -H1-            WVRQAPGQGLEWM         -H2-        RVTIT
C    QVQLVQSGAEVKKPGASVKVSCKAS     -H1-            WVRQAPGQGLEWM         -H2-        RVTIT
D    QVQLVQSGAEVKKPGASVKVSCKAS     -H1-            WVRQAPGQGLEWM         -H2-        RVTIT
II
A    QVQLQESGPGLVKPSQTLSLTCTVSGGSVS      -H1-      WIRQPPGKGLEWIG          -H2-      RVTIS
B    QVQLQESGPGLVKPSQTLSLTCTVS     -H1-            WIRQPPGKGLEWI         -H2-        RVTIS
C    QVQLQESGPGLVKPSQTLSLTCTVS     -H1-            WIRQPPGKGLEWI         -H2-        RVTIS
D    QVQLQESGPGLVKPSQTLSLTCTVS     -H1-            WIRQPPGKGLEWI         -H2-        RVTIS
III
A    EVQLVESGGGLVQPGGSLRLSCAASGFTFS      -H1-      WVRQAPGKGLEWVS          -H2-      RFTIS
B    EVQLVESGGGLVQPGGSLRLSCAAS     -H1-            WVRQAPGKGLEWV         -H2-        RFTIS
C    EVQLVESGGGLVQPGGSLRLSCAAS     -H1-            WVRQAPGKGLEWV         -H2-        RFTIS
D    EVQLVESGGGLVQPGGSLRLSCAAS     -H1-            WVRQAPGKGLEWV         -H2-        RFTIS
Acceptor
A    EVQLVESGGGLVQPGGSLRLSCAASGFNIK      -H1-      WVRQAPGKGLEWVS          -H2-      RFTIS
B    EVQLVESGGGLVQPGGSLRLSCAAS     -H1-            WVRQAPGKGLEWV         -H2-        RFTIS
C    EVQLVESGGGLVQPGGSLRLSCAAS     -H1-            WVRQAPGKGLEWV         -H2-        RFTIS
Second Acceptor
A    EVQLVESGGGLVQPGGSLRLSCAASGFNIK      -H1-      WVRQAPGKGLEWVS          -H2-      RFTIS
B    EVQLVESGGGLVQPGGSLRLSCAAS     -H1-            WVRQAPGKGLEWV         -H2-        RFTIS
C    EVQLVESGGGLVQPGGSLRLSCAAS     -H1-            WVRQAPGKGLEWV         -H2-        RFTIS
D    EVQLVESGGGLVQPGGSLRLSCAAS     -H1-            WVRQAPGKGLEWV         -H2-        RFTIS
```

FIG. 3A

| | | | | |
|---|---|---|---|---|
| I | | | | |
| A | ADTSTSTAYMELSSLRSEDTAVYYCAR | -H3- | WGQGTLVTVSS | SEQ ID NO: 19 |
| B | ADTSTSTAYMELSSLRSEDTAVYYCAR | -H3- | WGQGTLVTVSS | SEQ ID NO: 20 |
| C | ADTSTSTAYMELSSLRSEDTAVYYCA | -H3- | WGQGTLVTVSS | SEQ ID NO: 21 |
| D | ADTSTSTAYMELSSLRSEDTAVYYC | -H3- | WGQGTLVTVSS | SEQ ID NO: 22 |
| II | | | | |
| A | VDTSKNQFSLKLSSVTAADTAVYYCAR | -H3- | WGQGTLVTVSS | SEQ ID NO: 23 |
| B | VDTSKNQFSLKLSSVTAADTAVYYCAR | -H3- | WGQGTLVTVSS | SEQ ID NO: 24 |
| C | VDTSKNQFSLKLSSVTAADTAVYYCA | -H3- | WGQGTLVTVSS | SEQ ID NO: 25 |
| D | VDTSKNQFSLKLSSVTAADTAVYYC | -H3- | WGQGTLVTVSS | SEQ ID NO: 26 |
| III | | | | |
| A | RDNSKNTLYLQMNSLRAEDTAVYYCAR | -H3- | WGQGTLVTVSS | SEQ ID NO: 27 |
| B | RDNSKNTLYLQMNSLRAEDTAVYYCAR | -H3- | WGQGTLVTVSS | SEQ ID NO: 28 |
| C | RDNSKNTLYLQMNSLRAEDTAVYYCA | -H3- | WGQGTLVTVSS | SEQ ID NO: 29 |
| D | RDNSKNTLYLQMNSLRAEDTAVYYC | -H3- | WGQGTLVTVSS | SEQ ID NO: 30 |
| Acceptor | | | | |
| A | ADTSKNTAYLQMNSLRAEDTAVYYCSR | -H3- | WGQGTLVTVSS | SEQ ID NO: 31 |
| B | ADTSKNTAYLQMNSLRAEDTAVYYCSR | -H3- | WGQGTLVTVSS | SEQ ID NO: 32 |
| C | ADTSKNTAYLQMNSLRAEDTAVYYCS | -H3- | WGQGTLVTVSS | SEQ ID NO: 33 |
| Second Acceptor | | | | |
| A | ADTSKNTAYLQMNSLRAEDTAVYYCAR | -H3- | WGQGTLVTVSS | SEQ ID NO: 34 |
| B | ADTSKNTAYLQMNSLRAEDTAVYYCAR | -H3- | WGQGTLVTVSS | SEQ ID NO: 35 |
| C | ADTSKNTAYLQMNSLRAEDTAVYYCA | -H3- | WGQGTLVTVSS | SEQ ID NO: 36 |
| D | ADTSKNTAYLQMNSLRAEDTAVYYC | -H3- | WGQGTLVTVSS | SEQ ID NO: 37 |

FIG. 3B

Framework Sequences of huMAb4D5-8 Light Chain

LC-FR1 $^{1}$Asp Ile Gln Met Thr Gln Ser Pro Ser Ser Leu Ser Ala Ser Val Gly Asp Arg Val Thr Ile Thr Cys$^{23}$ (SEQ ID NO: 126)

LC-FR2 $^{35}$Trp Tyr Gln Gln Lys Pro Gly Lys Ala Pro Lys Leu Leu Ile Tyr$^{49}$ (SEQ ID NO: 127)

LC-FR3 $^{57}$Gly Val Pro Ser Arg Phe Ser Gly Ser Arg Ser Gly Thr Asp Phe Thr Leu Thr Ile Ser Ser Leu Gln Pro Glu Asp Phe Ala Thr Tyr Tyr Cys$^{88}$ (SEQ ID NO: 164)

LC-FR4 $^{98}$Phe Gly Gln Gly Thr Lys Val Glu Ile Lys$^{107}$ (SEQ ID NO: 129)

Framework Sequences of huMAb4D5-8 Heavy Chain

HC-FR1 $^{1}$Glu Val Gln Leu Val Glu Ser Gly Gly Gly Leu Val Gln Pro Gly Gly Ser Leu Arg Leu Ser Cys Ala Ala Ser$^{25}$ (SEQ ID NO: 122)

HC-FR2 $^{36}$Trp Val Arg Gln Ala Pro Gly Lys Gly Leu Glu Trp Val$^{48}$ (SEQ ID NO: 123)

HC-FR3 $^{66}$Arg Phe Thr Ile Ser Ala Asp Thr Ser Lys Asn Thr Ala Tyr Leu Gln Met Asn$^{83}$ Ser$^{83a}$ Leu$^{83b}$ Arg$^{83c}$ Ala Glu Asp Thr Ala Val Tyr Tyr Cys$^{92}$ (SEQ ID NO: 154)

HC-FR4 $^{103}$Trp Gly Gln Gly Thr Leu Val Thr Val Ser Ser$^{113}$ (SEQ ID NO: 125)

*FIG. 5*

Framework Sequences of huMAb4D5-8 Light Chain Modified at Position 66 (Underlined)

LC-FR1 $^{1}$Asp Ile Gln Met Thr Gln Ser Pro Ser Ser Leu Ser Ala Ser Val Gly Asp Arg Val Thr Ile Thr Cys$^{23}$ (SEQ ID NO: 126)

LC-FR2 $^{35}$Trp Tyr Gln Gln Lys Pro Gly Lys Ala Pro Lys Leu Leu Ile Tyr$^{49}$ (SEQ ID NO: 127)

LC-FR3 $^{57}$Gly Val Pro Ser Arg Phe Ser Gly Ser <u>Gly</u> Ser Gly Thr Asp Phe Thr Leu Thr Ile Ser Ser Leu Gln Pro Glu Asp Phe Ala Thr Tyr Tyr Cys$^{88}$ (SEQ ID NO: 128)

LC-FR4 $^{98}$Phe Gly Gln Gly Thr Lys Val Glu Ile Lys$^{107}$ (SEQ ID NO: 129)

Framework Sequences of huMAb4D5-8 Heavy Chain Modified at Postions 71, 73 and 78 (Underlined)

HC-FR1 $^{1}$Glu Val Gln Leu Val Glu Ser Gly Gly Gly Leu Val Gln Pro Gly Gly Ser Leu Arg Leu Ser Cys Ala Ala Ser$^{25}$ (SEQ ID NO: 122)

HC-FR2 $^{36}$Trp Val Arg Gln Ala Pro Gly Lys Gly Leu Glu Trp Val$^{48}$ (SEQ ID NO: 123)

HC-FR3 $^{66}$Arg Phe Thr Ile Ser <u>Arg</u> Asp <u>Asn</u> Ser Lys Asn Thr <u>Leu</u> Tyr Leu Gln Met Asn83 Ser83a Leu83b Arg83c Ala Glu Asp Thr Ala Val Tyr Tyr Cys$^{92}$ (SEQ ID NO: 124)

HC-FR4 $^{103}$Trp Gly Gln Gly Thr Leu Val Thr Val Ser Ser$^{113}$ (SEQ ID NO: 125)

*FIG. 6*

MAWRCPRMGRVPLAWCLALCGWACMAPRGTQAEESPFVGNPGNI
TGARGLTGTLRCQLQVQGEPPEVHWLRDGQILELADSTQTQVPLGEDEQDDWIVVSQL
RITSLQLSDTGQYQCLVFLGHQTFVSQPGYVGLEGLPYFLEEPEDRTVAANTPFNLSC
QAQGPPEPVDLLWLQDAVPLATAPGHGPQRSLHVPGLNKTSSFSCEAHNAKGVTTSRT
ATITVLPQQPRNLHLVSRQPTELEVAWTPGLSGIYPLTHCTLQAVLSDDGMGIQAGEP
DPPEEPLTSQASVPPHQLRLGSLHPHTPYHIRVACTSSQGPSSWTHWLPVETPEGVPL
GPPENISATRNGSQAFVHWQEPRAPLQGTLLGYRLAYQGQDTPEVLMDIGLRQEVTLE
LQGDGSVSNLTVCVAAYTAAGDGPWSLPVPLEAWRPVKEPSTPAFSWPWWYVLLGAVV
AAACVLILALFLVHRRKKETRYGEVFEPTVERGELVVRYRVRKSYSRRTTEATLNSLG
ISEELKEKLRDVMVDRHKVALGKTLGEGEFGAVMEGQLNQDDSILKVAVKTMKIAICT
RSELEDFLSEAVCMKEFDHPNVMRLIGVCFQGSERESFPAPVVILPFMKHGDLHSFLL
YSRLGDQPVYLPTQMLVKFMADIASGMEYLSTKRFIHRDLAARNCMLNENMSVCVADF
GLSKKIYNGDYYRQGRIAKMPVKWIAIESLADRVYTSKSDVWSFGVTMWEIATRGQTP
YPGVENSEIYDYLRQGNRLKQPADCLDGLYALMSRCWELNPQDRPSFTELREDLENTL
KALPPAQEPDEILYVNMDEGGGYPEPPGAAGGADPPTQPDPKDSCSCLTAAEVHPAGR
YVLCPSTTPSPAQPADRGSPAAPGQEDGA (SEQ ID NO: 165)

*FIG. 12*

ANTI-AXL ANTIBODIES AND METHODS OF USE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

RELATED APPLICATIONS

This application *is a reissue application of U.S. Pat. No. 8,853,369 B2 which issued from U.S. patent application Ser. No. 13/708,685, filed Dec. 7, 2012, which* is a continuation of International Application No. PCT/US2011/040825, filed Jun. 17, 2011, which claims priority under 35 USC §119 to U.S. Provisional Application No. 61/356,508, filed Jun. 18, 2010, the contents of which are incorporated by reference in their entirety.

SEQUENCE LISTING

The instant application contains a Sequence Listing which has been submitted in ASCII format via EFS-Web and is hereby incorporated by reference in its entirety. Said ASCII COPY, created on [Mar. 15, 2013] *Oct. 5, 2016*, is named [P4436R1C1-US SL.txt] *146392038030seqlisting.txt* and is [67,128] *67,064* bytes in size.

FIELD OF THE INVENTION

The present invention relates to anti-Axl antibodies and methods of using the same.

BACKGROUND

Axl is a member of the TAM (Tyro3, Axl, and Mer) family of receptor tyrosine kinases (O'Bryan et al, 1991; Lai et al, 1991). It was originally identified as a transforming gene in hematological malignancies (O'Bryan et al, 1991; Janssen et al, 1991). Dysregulation of Axl or its ligand Gas6 is implicated in the pathogenesis of a variety of human cancers. Axl overexpression has been reported in a wide array of human cancers (Berclaz et al, 2001; Craven et al, 1995; Shieh et al, 2005; Sun et al, 2004; Ito et al, 1999) and is associated with invasiveness and metastasis in lung (Shieh et al, 2005), prostate (Sainaghi et al, 2005), breast (Meric et al, 2002; Zhang et al, 2008), gastric (Wu et al, 2002), and pancreatic (Koorstra et al, 2009) cancers, renal cell carcinoma (Chung et al, 2003), as well as glioblastoma (Hutterer et al, 2008). Recently, by profiling of phosphotyrosine signaling, activated Axl protein was detected in about 5% primary tumors of NSCLC (Rikova et al, 2007). Axl expression is induced by targeted and chemotherapy drugs and drug-induced Axl expression confers resistance to chemotherapy in acute myeloid leukemia (Hong et al, 2008), as well as resistance to imatinib and Lapatinib/Herceptin in gastrointestinal stromal tumors (Mehadevan, et al, 2007) and breast cancer (Liu et al, 2009), respectively. Other publications relating to Axl and anti-Axl antibodies include WO2004/039955, WO2009/063965; co-owned U.S. application No. 61/228,915 filed Jul. 27, 2009; WO2009/062690; WO2004/008147; U.S. Pat. No. 5,468,634.

It is clear that there continues to be a need for agents that have clinical attributes that are optimal for development as therapeutic agents. The invention described herein meets this need and provides other benefits.

All references cited herein, including patent applications and publications, are incorporated by reference in their entirety.

SUMMARY

The invention provides anti-Axl antibodies and methods of using the same.

In one aspect, the invention provides an isolated antibody that binds to human Axl, wherein the antibody binds human Axl with an affinity of ≤600 pM, wherein the antibody binds mouse Axl with an affinity of ≤1 nM. In some embodiments, the antibody promotes Axl receptor downregulation. In some embodiments, the antibody inhibits constitutive Axl activation. In some embodiments, the antibody binds a polypeptide comprising, consisting essentially of or consisting of the following amino acid sequence:

(SEQ ID NO: 111)
MAWRCPRMGRVPLAWCLALCGWACMAPRGTQAEESPFVGNPGNITGARGL

TGTLRCQLQVQGEPPEVHWLRDGQILELADSTQTQVPLGEDEQDDWIVVS

QLRITSLQLSDTGQYQCLVFLGHQTFVSQPGYVG.

In further embodiments, the antibody is a monoclonal antibody. In some embodiments, the antibody is a human, humanized, or chimeric antibody. In some embodiments, the antibody is is an antibody fragment that binds Axl. In some embodiments, the antibody is a human antibody.

In one aspect, the invention provides an anti-Axl antibody, wherein the antibody comprises (a) HVR-H1 comprising $GFX_1X_2X_3X_4X_5X_6X_7H$, wherein $X_1$ is S or T; $X_2$ is L, F or V; $X_3$ is S, T, or R; $X_4$ is G or S; $X_5$ is S, H, T or I; $X_6$ is W or G; $X_7$ is I or L (SEQ ID NO:112), (b) HVR-H2 comprising $X_1X_2IX_3PX_4X_5X_6X_7X_8YYADSVKG$, wherein $X_1$ is G or A; $X_2$ is W or G; $X_3$ is N, S, A or P; $X_4$ is Y, A or V; $X_5$ is R, G, or S; $X_6$ is G R or S; $X_7$ is Y, S, H or Y; $X_8$ is A, T, or P (SEQ ID NO:113) and/or HVR-H2 comprising $X_1X_2IX_3PX_4X_5X_6X_7X_8X_9X_{10}YYADSVKG$, wherein $X_1$ is G or A; $X_2$ is W or G; $X_3$ is N, S, A or P; $X_4$ is Y, A or V; $X_5$ is R, G, or S; $X_6$ is G R or S; $X_7$ is Y, S, H or Y; $X_8$ is A, T, or P; $X_9$ is any amino acid or absent; $X_{10}$ is any amino acid or absent (SEQ ID NO:166); (c) HVR-H3 comprising $ARX_1X_2X_3X_4X_5X_6X_7X_8X_9X_{10}X_{11}X_{12}X_{13}MDY$, wherein $X_1$ is E or W; $X_2$ is Y or R; $X_3$ is S, N or P; $X_4$ is G, D, or L; $X_5$ is W or S; $X_6$ is G, R, A, or S; $X_7$ is G or S; $X_8$ is S or absent; $X_9$ is S, Y or absent; $X_{10}$ is V, I or absent; $X_{11}$ is G or absent; $X_{12}$ is Y or absent; $X_{13}$ is A, E or absent (SEQ ID NO:114); (d) HVR-L1 comprising $RASQX_1X_2X_3X_4X_5X_6A$, wherein $X_1$ is D, I or S; $X_2$ is V or I; $X_3$ is S, G or R; $X_4$ is T, I, N or R; $X_5$ is A or S; $X_6$ is V or L (SEQ ID NO:115); (e) HVR-L2 comprising $X_1ASX_2LX_3S$, wherein $X_1$ is S, A, or V; $X_2$ is F, N or S; $X_3$ is Y or A (SEQ ID NO:116); and (f) HVR-L3 comprising $QQX_1X_2X_3X_4X_5X_6T$, wherein $X_1$ is S or A; $X_2$ is Y, K or N; $X_3$ is T, S, Y, M, R or A; $X_4$ is T, N, S, or F; $X_5$ is P or R; $X_6$ is P, Y, S or L (SEQ ID NO:117).

In another aspect, the invention provides an anti-Axl antibody wherein the antibody comprises (a) HVR-H1 comprising $GFX_1X_2X_3GX_4WIH$, wherein $X_1$ is T or S, $X_2$ is F or L, $X_3$ is T or S, $X_4$ is H, S or T (SEQ ID NO:118); (b) HVR-H2 comprising $GWIX_1PYX_2X_3X_4X_5YYADSVKG$, wherein $X_1$ is S, N or A; $X_2$ is G, R or S; $X_3$ is G or R; $X_4$ is S, Y or H; $X_5$ is T, A or P (SEQ ID NO:119); (c) HVR-H3 comprising $AREYX_1X_2WX_3X_4SX_5X_6GYX_7MDY$, wherein $X_1$ is S, N or P; $X_2$ is G or D; $X_3$ is G, R, or A; $X_4$ is G or S; $X_5$ is S or Y; $X_6$ is V or I; $X_7$ is A or E (SEQ ID NO:120); and (d) HVR-L3 comprising $QQSYX_1X_2X_3X_4T$, wherein $X_1$ is T, S or Y; $X_2$ is T, N, S or F; $X_3$ is P or R; $X_4$ is P, Y or S (SEQ ID NO:121).

In another aspect, the invention provides an anti-Axl antibody comprising (a) HVR-H3 comprising the amino acid sequence of SEQ ID NO:9, (b) HVR-L3 comprising the amino acid sequence of SEQ ID NO:12, and (c) HVR-H2 comprising the amino acid sequence of SEQ ID NO:8.

In another aspect, the invention provides an anti-Axl antibody comprising (a) HVR-H1 comprising the amino acid sequence of SEQ ID NO:7, (b) HVR-H2 comprising the amino acid sequence of SEQ ID NO:8, and (c) HVR-H3 comprising the amino acid sequence of SEQ ID NO:9.

In another aspect, the invention provides an anti-Axl antibody comprising (a) HVR-L1 comprising the amino acid sequence of SEQ ID NO:10; (b) HVR-L2 comprising the amino acid sequence of SEQ ID NO:11; and (c) HVR-L3 comprising the amino acid sequence of SEQ ID NO:12.

In another aspect, the invention provides an anti-Axl antibody comprising (a) HVR-L1 comprising the amino acid sequence of SEQ ID NO:10; (b) HVR-L2 comprising the amino acid sequence of SEQ ID NO:11; and (c) HVR-L3 comprising the amino acid sequence of SEQ ID NO:12.

In some embodiments, the antibody further comprises a heavy chain variable domain or light chain variable domain framework sequence shown in FIG. 3A-B, 4, 5 or 6.

In one aspect, the invention provides an anti-Axl antibody comprising (a) a VH sequence having at least 95% sequence identity to the amino acid sequence of SEQ ID NO:103; (b) a VL sequence having at least 95% sequence identity to the amino acid sequence of SEQ ID NO:104; or (c) a VH sequence as in (a) and a VL sequence as in (b). In some embodiments, the antibody comprises a VH sequence of SEQ ID NO:103. In some embodiments, the antibody comprises a VL sequence of SEQ ID NO:104. In some embodiments, the antibody comprises a VH sequence of SEQ ID NO:103 and a VL sequence of SEQ ID NO:104.

In some embodiments, the antibody is a full length IgG1 antibody.

The invention also provides isolated nucleic acid encoding any of the antibodies of the invention.

The invention also provides host cells comprising the nucleic acids of the invention.

The invention also provides methods of producing an antibody comprising culturing the host cell of the invention so that the antibody is produced. In some embodiments, the methods further comprise recovering the antibody from the host cell.

The invention also provides an immunoconjugate comprising any of the anti-Axl antibodies of the invention and a cytotoxic agent.

The invention also provides avpharmaceutical formulation comprising comprising any of the anti-Axl antibodies of the invention and a pharmaceutically acceptable carrier. In some embodiments, the pharmaceutical formulation further comprises an additional therapeutic agent. In some embodiments, the additional therapeutic agent is selected from a VEGF antagonist, an EGFR antagonist, and a chemotherapeutic agent.

The invention also provides any of the anti-Axl antibodies described herein for use as a medicament. In some embodiments, the use is for treating cancer. In some embodiments, the use is for treating immune disorder, cardiovascular disorder, thrombosis or diabetes. In some embodiments, the use is for inhibiting cell proliferation. In some embodiments, the use is for promoting Axl downregulation. In some embodiments, the use is for inhibiting angiogenesis.

The invention also provides any of the anti-Axl antibodies described herein for use in the manufacture of a medicament. In some embodiments, the medicament is for treatment of cancer. In some embodiments, the medicament is for treatment of immune disorder, cardiovascular disorder, thrombosis or diabetes. In some embodiments, the medicament is for inhibiting cell proliferation, inhibiting angiogenesis, promoting Axl downregulation, inhibiting metastasis, inhibiting angiogenesis.

The invention also provides methods of treating an individual having cancer comprising administering to the individual an effective amount of any of the anti-Axl antibodies disclosed herein. In some embodiments, the methods further comprise administering an additional therapeutic agent to the individual. In some embodiments, the additional therapeutic agent is selected from the group consisting of a VEGF antagonist, an EGFR antagonist and a chemotherapeutic agent.

The invention also provides methods of treating an individual having immune disorder, cardiovascular disorder, thrombosis or diabetes comprising administering to the individual an effective amount of any of the anti-Axl antibodies disclosed herein.

The invention also provides methods of inhibiting angiogenesis, inhibiting cell proliferation, promoting Axl receptor downregulation or inhibiting metastasis in an individual comprising administering to the individual an effective amount of any of the anti-Axl antibodies disclosed herein to inhibit angiogenesis, inhibit cell proliferation, promote Axl receptor downregulation or inhibit metastasis.

The invention also provides methods of inhibiting constitutive Axl activation comprising administering to the individual an effective amount of any of the anti-Axl antibodies disclosed herein. to inhibit constitutive Axl.

In one aspect, the invention provides methods for treating a subject suffering from a cancer associated with an EGFR activating mutation or an EGFR gene amplification, wherein the subject has developed a resistance to treatment with an EGFR antagonist, comprising determining whether the subject has Axl expression, an Axl activating mutation or an Axl gene amplification, and administering to those subjects having an Axl activating mutation or an Axl gene amplification an EGFR antagonist and any of the anti-Axl antibodies described herein.

In one aspect, the invention provides methods for treating a subject suffering from a cancer associated with an EGFR activating mutation or an EGFR gene amplification, comprising: (i) monitoring a subject being treated with an EGFR antagonist to determine if the subject develops Axl expression, an Axl activating mutation or an Axl gene amplification, and (ii) modifying the treatment regimen of the subject to include any of the anti-Axl antibodies described herein in addition to the EGFR antagonist where the subject has developed an Axl activating mutation or an Axl gene amplification.

In one aspect, the invention provides methods for treating a subject suffering from a cancer associated with an EGFR activating mutation or an EGFR gene amplification, comprising: (i) monitoring a subject being treated with EGFR antagonist to determine if the subject develops a resistance to the inhibitor, (ii) testing the subject to determine whether the subject has Axl expression, an Axl activating mutation or an Axl gene amplification, and (iii) modifying the treatment regimen of the subject to include any of the anti-Axl antibodies described herein in addition to the EGFR antagonist where the subject has an Axl activating mutation or an Axl gene amplification.

In one aspect, the invention provides methods for evaluating an EGFR antagonist, comprising: (i) monitoring a population of subjects being treated with an EGFR antagonist to identify those subjects that develop a resistance to the therapeutic, (ii) testing the resistant subjects to determine whether the subjects have Axl expression, an Axl activating mutation or an Axl gene amplification, and (iii) modifying the treatment regimen of the subjects to include any of the anti-Axl antibodies described herein in addition to the EGFR antagonist where the subjects have Axl expression, an Axl activating mutation or an Axl gene amplification.

In one aspect, the invention provides methods for reducing EGFR phosphorylation in a cancer cell, wherein said cancer cell has acquired resistance to an EGFR antagonist, and wherein said cell comprises an Axl activating mutation or an Axl gene amplification, comprising the step of contacting the cell with any of the anti-Axl antibodies described herein and an EGFR antagonist.

In one aspect, the invention provides methods for reducing PI3K mediated signaling in a cancer cell, wherein said cancer cell has acquired resistance to an EGFR antagonist, and wherein said cell comprises Axl expression, an Axl activating mutation or an Axl gene amplification, comprising the step of contacting the cell with any of the anti-Axl antibodies described herein and an EGFR antagonist.

In one aspect, the invention provides methods for reducing EGFR-mediated signaling in a cancer cell, wherein said cancer cell has acquired resistance to an EGFR antagonist, and wherein said cell comprises Axl expression, an Axl activating mutation or an Axl gene amplification, comprising contacting the cell with any of the anti-Axl antibodies described herein and an EGFR antagonist.

In one aspect, the invention provides methods for restoring sensitivity of a cancer cell to an EGFR antagonist, wherein said cancer cell has acquired resistance to an EGFR antagonist, and wherein said cell comprises Axl expression, an Axl activating mutation or an Axl gene amplification, comprising contacting the cell with any of the anti-Axl antibodies described herein and an EGFR antagonist.

In one aspect, the invention provides methods for reducing growth or proliferation of a cancer cell, wherein said cancer cell has acquired resistance to an EGFR antagonist, and wherein said cell comprises Axl expression, an Axl activating mutation or an Axl gene amplification, comprising the step of contacting the cell with any of the anti-Axl antibodies described herein and an EGFR antagonist.

In one aspect, the invention provides methods for increasing apoptosis of a cancer cell, wherein said cancer cell has acquired resistance to an EGFR antagonist, and wherein said cell comprises Axl expression, an Axl activating mutation or an Axl gene amplification, comprising the step of contacting the cell with any of the anti-Axl antibodies described herein and an EGFR antagonist.

In one aspect, the invention provides methods for reducing resistance of a cancer cell to an EGFR antagonist, wherein said cancer cell has acquired resistance to an EGFR antagonist, and wherein said cell comprises an Axl activating mutation or an Axl gene amplification, comprising the step of contacting the cell with any of the anti-Axl antibodies described herein and an EGFR antagonist.

In one aspect, the invention provides methods for treating acquired EGFR antagonist resistance in a cancer cell, wherein said cell comprises an Axl activating mutation or an Axl gene amplification, comprising contacting the cell with any of the anti-Axl antibodies described herein and an EGFR antagonist.

In some embodiments, the cancer cell is any EGFR-driven cancer. In some embodiments, the cancer cell comprises an EGFR activating mutation. In some embodiments, the cancer cell comprises an EGFR gene amplification. In some embodiments, the EGFR gene amplification is at least 2-fold. In some embodiments, the Axl amplification is at least 2-fold. In some embodiments, the cancer cell comprises an EGFR gene mutation associated with increased resistance to an EGFR antagonist. In some embodiments, the EGFR gene mutation associated with increased resistance to an EGFR antagonist is a T790M mutation of EGFR. In some embodiments, the EGFR antagonist is a small molecule therapeutic, a nucleic acid therapeutic, or a protein therapeutic. In some embodiments, the EGFR antagonist is an antibody, an antisense molecule, or a small molecule kinase inhibitor. In some embodiments, the EGFR antagonist is an EGFR kinase inhibitor selected from the group consisting of: gefitinib, erlotinib, cetuximab, pantinumumab. In some embodiments, the EGFR antagonist is an anti-EGFR antibody selected from the group consisting of: cetuximab, panitumumab. In some embodiments, the nucleic acid therapeutic is a siRNA molecule.

In one aspect, the invention provides methods for identifying a subject as a candidate for treatment with an EGFR antagonist and any of the anti-Axl antibodies described herein, wherein said subject has been treated with an EGFR antagonist and suffers from cancer that has acquired resistance to said EGFR antagonist, comprising detecting Axl expression, an Axl activating mutation or Axl gene amplification in a cancer cell from said subject.

In one aspect, the invention provides methods for identifying a subject who is being treated with an EGFR antagonist and who is at risk for acquiring resistance to said EGFR antagonist, comprising detecting the presence of Axl expression, an Axl activating mutation or an Axl gene amplification in a cancer cell from said subject, wherein the presence of said Axl expression, Axl activating mutation or Axl gene amplification indicates a risk for acquiring said resistance.

In one aspect, the invention provides methods for treating a subject suffering from a cancer that is resistant to treatment with an EGFR antagonist, comprising administering to the subject an EGFR antagonist and any of the anti-Axl antibodies described herein.

In one aspect, the invention provides methods for treating a subject suffering from a cancer associated with an EGFR activating mutation or an EGFR gene amplification, wherein the subject has developed a resistance to treatment with an EGFR antagonist, comprising determining whether the subject has Axl expression, such as elevated Axl levels and/or activity, and administering to those subjects having Axl expression, such as elevated Axl activity an EGFR antagonist and any of the anti-Axl antibodies described herein.

In one aspect, the invention provides methods for treating a subject suffering from a cancer associated with an EGFR activating mutation or an EGFR gene amplification, comprising: (i) monitoring a subject being treated with an EGFR antagonist to determine if the subject develops Axl expression, such as elevated levels and/or Axl activity, and (ii) modifying the treatment regimen of the subject to include any of the anti-Axl antibodies described herein in addition to the EGFR antagonist where the subject has developed Axl expression, such as elevated Axl levels and/or activity.

In one aspect, the invention provides methods for treating a subject suffering from a cancer associated with an EGFR activating mutation or an EGFR gene amplification, comprising: (i) monitoring a subject being treated with EGFR antagonist to determine if the subject develops a resistance to the inhibitor, (ii) testing the subject to determine whether the subject has Axl expression, such as elevated Axl levels and/or activity, and (iii) modifying the treatment regimen of the subject to include any of the anti-Axl antibodies described herein in addition to the EGFR antagonist where the subject has elevated Axl levels and/or activity.

In another aspect, the invention provides a method for (i) restoring the sensitivity of a cancer cell to an EGFR antagonist, (ii) reducing resistance of a cancer cell to an EGFR antagonist, and/or (iii) treating acquired EGFR antagonist resistance in a cancer cell, by contacting the cell with an EGFR antagonist and any of the anti-Axl antibodies described herein. In exemplary embodiments, the cancer cell has acquired a resistance to an EGFR antagonist and comprises elevated levels of Axl activity and/or expression, e.g., associated with an activating mutation in the Axl gene, an Axl gene amplification, or Gas6 mediated Axl activation. The methods disclosed herein may be used to restore the sensitivity, reduce the resistance, and/or treat an acquired resistance, of a cancer cell.

In another aspect, the invention provides a method for reducing growth and/or proliferation of a cancer cell, or increasing apoptosis of a cancer cell, by contacting the cell with an EGFR antagonist and any of the anti-Axl antibodies described herein. In exemplary embodiments, the cancer cell has acquired a resistance to an EGFR antagonist and comprises elevated Axl activity and/or expression, e.g., associated with an activating mutation in the Axl gene, an Axl gene amplification, or Gas6 mediated Axl activation.

BRIEF DESCRIPTION OF THE FIGURES

FIGS. 1A-F: Heavy chain and light chain HVR loop sequences of anti-Axl antibodies. The figures show the heavy chain HVR sequences, H1, H2, and H3, and light chain HVR sequences, L1, L2, and L3. Amino acid positions are numbered according to the Kabat numbering system as described herein.

FIG. 2: depict the amino acid sequences of the heavy chain variable regions and light chain variable regions of anti-Axl antibodies.

FIGS. 3A-B and 4: depict exemplary acceptor human consensus framework sequences for use in practicing the instant invention with sequence identifiers as follows:

Variable Heavy (VH) Consensus Frameworks (FIG. 3A-B)

human VH subgroup I consensus framework minus Kabat CDRs (SEQ ID NOS:131-133 and 125, respectively, in order of appearance)

human VH subgroup I consensus framework minus extended hypervariable regions (SEQ ID NOS:134-135, 133, 125, 134-136, 125, 134-135, 137, and 125, respectively, in order of appearance)

human VH subgroup II consensus framework minus Kabat CDRs (SEQ ID NOS:138-140, and 125, respectively, in order of appearance)

human VH subgroup II consensus framework minus extended hypervariable regions (SEQ ID NOS:141-142, 140, 125, 141-143, 125, 141-142, 144, and 125, respectively, in order of appearance)

human VH subgroup II consensus framework minus extended human VH subgroup III consensus framework minus Kabat CDRs (SEQ ID NOS:145-147 and 125, respectively, in order of appearance)

human VH subgroup III consensus framework minus extended hypervariable regions (SEQ ID NOS:122-123, 147, 125, 122-123, 148, 125, and 122-125, respectively, in order of appearance)

human VH acceptor framework minus Kabat CDRs (SEQ ID NOS:149, 146, 150, and 125, respectively, in order of appearance)

human VH acceptor framework minus extended hypervariable regions (SEQ ID NOS:122-123, 150, 125, 122-123, 151, and 125, respectively, in order of appearance) human VH acceptor 2 framework minus Kabat CDRs (SEQ ID NOS:149, 146, 152, and 125, respectively, in order of appearance)

human VH acceptor 2 framework minus extended hypervariable regions (SEQ ID NOS:122-123, 152, 125, 122-123, 153, 125, 122-123, 154, and 125, respectively, in order of appearance)

Figure 4:
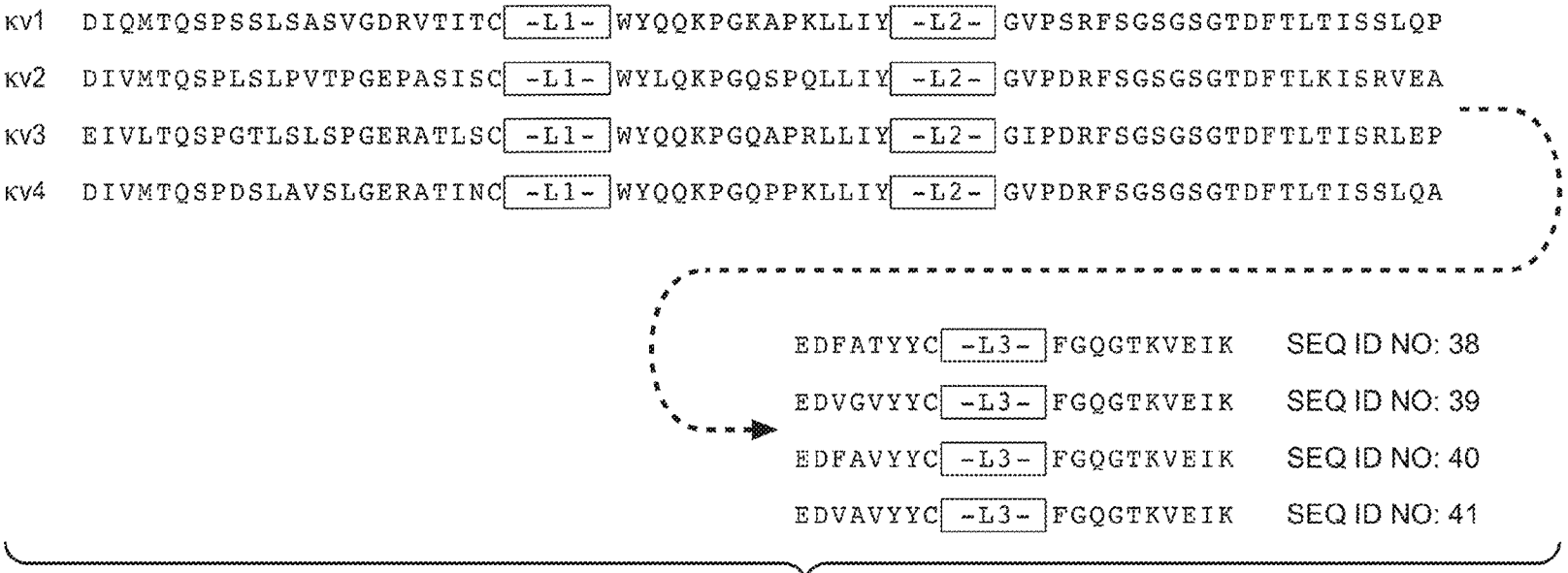

Variable Light (VL) Consensus Frameworks (FIG. 4)

human VL kappa subgroup I consensus framework (SEQ ID NOS:126-129, respectively, in order of appearance)

human VL kappa subgroup II consensus framework (SEQ ID NOS:155-157 and 129, respectively, in order of appearance)

human VL kappa subgroup III consensus framework (SEQ ID NOS:158-160 and 129, respectively, in order of appearance)

human VL kappa subgroup IV consensus framework (SEQ ID NOS: 161-163 and 129, respectively, in order of appearance)

FIG. 5: depicts framework region sequences of huMAb4D5-8 light (SEQ ID NOS:126-127, 164, and 129, respectively, in order of appearance) and heavy chains (SEQ ID NOS:122-123, 154, and 125, respectively, in order of appearance). Numbers in superscript/bold indicate amino acid positions according to Kabat.

FIG. 6: depicts modified/variant framework region sequences of huMAb4D5-8 light (SEQ ID NOS:126-129, respectively, in order of appearance) and heavy chains (SEQ ID NOS:122-125, respectively, in order of appearance). Numbers in superscript/bold indicate amino acid positions according to Kabat.

Figure 7A:
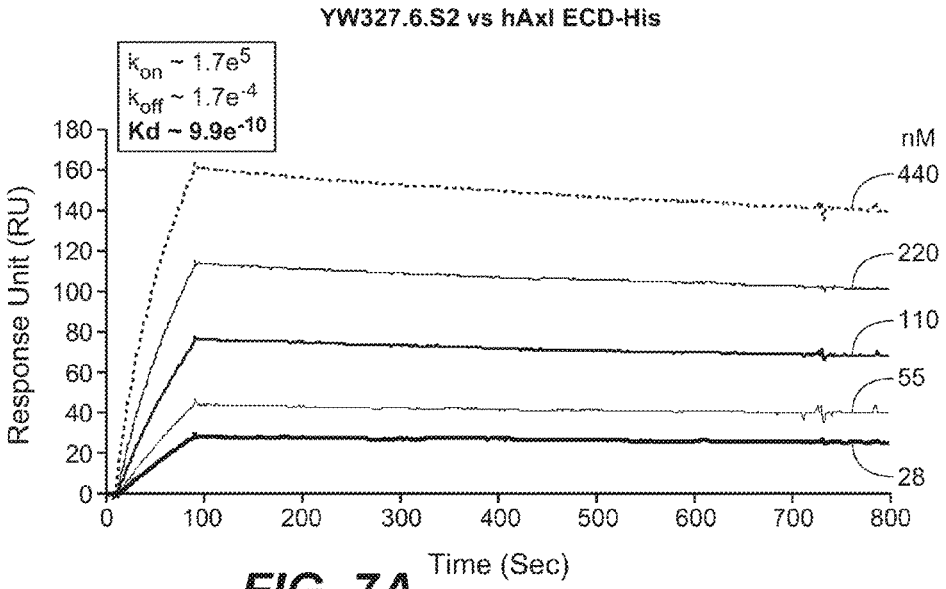
Figure 7B:
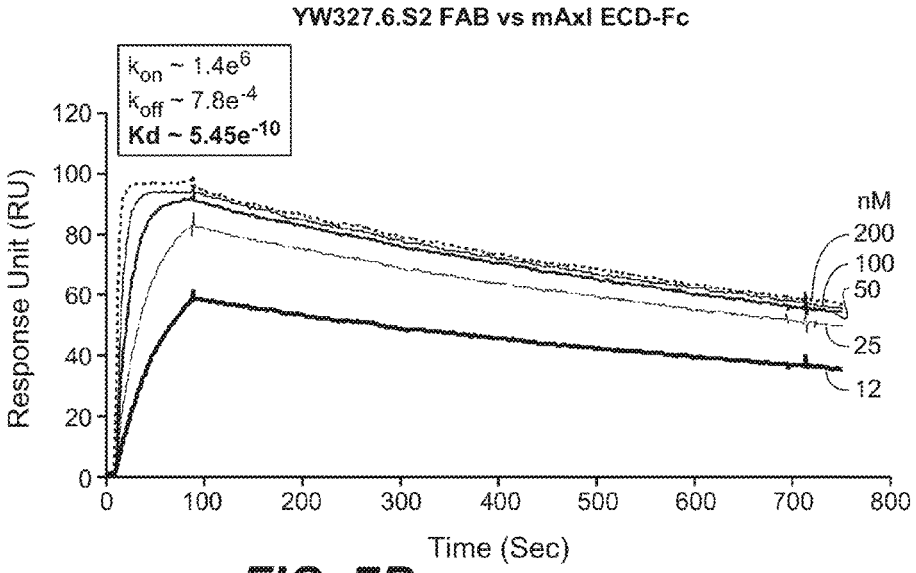
Figure 7C:
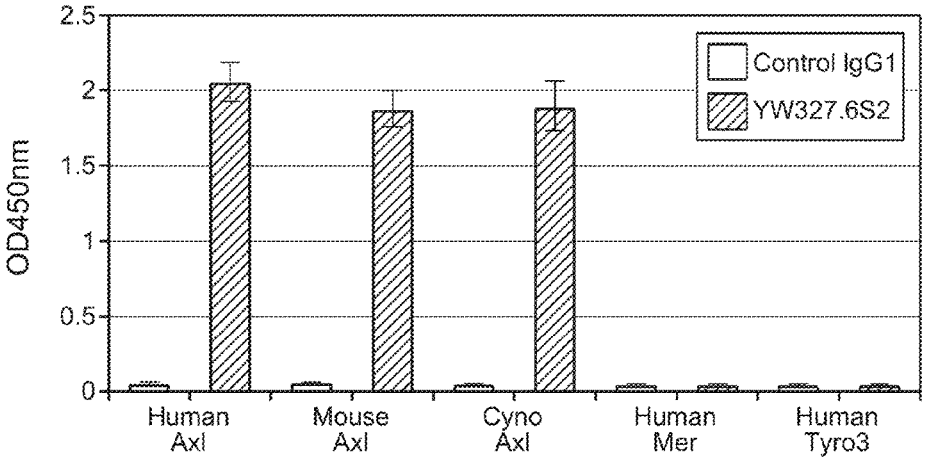
Figure 7D:
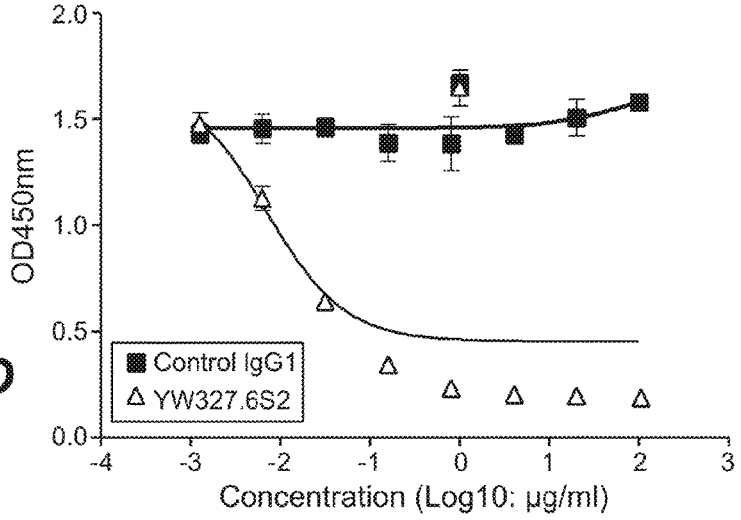
Figure 7E:
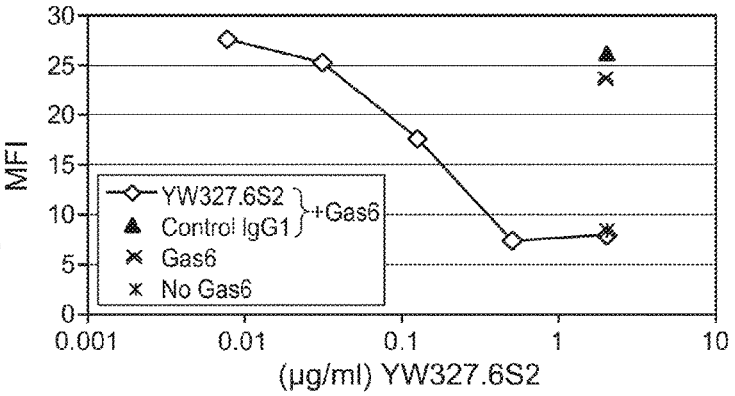

FIGS. 7A-H: Characterization of Axl mAb YW327.6S2. A-B. Affinity measurement of YW327.6S2 using BIAcore. Association rates ($k_{on}$) and dissociation rates ($k_{off}$) were calculated using the one-to-one Langmuir binding model. The equilibrium dissociation constant (Kd) was derived as the $k_{on}/k_{off}$ ratio. C. Cross reactivity of YW327.6S2. YW327.6S2 cross reacts with murine and cynomolgus Axl but not with Tyro3 or Mer. Plates were coated with anti-human IgG Fc, and then incubated with human Axl, Mer, Tyro3 Fcs, mouse or cynomolgus AxlFcs. After washing, isotype control antibody or YW327.6S2 was added and followed by HRP conjugated anti-human IgG. D-E. YW327.6S2 blocks Gas6 binding to Axl. FIG. 7D: ELISA. Plates were coated with anti-human IgG Fc and incubated with human Axl-Fc. After washing, Gas6 was added with or without antibodies. Binding of Gas6 was detected by biotylated anti-Gas6 antibody and streptavidin-HRP conjugate. FIG. 7E: FACS. HUVECs were harvested and treated with YW327.6S2 or control antibody and then incubated with Gas6 for 30 minutes on ice. Binding of Gas6 to the cell surface was detected by biotylated anti-Gas6 antibody and streptavidin-PE conjugate. F. YW327.6S2 down-regulates Axl expression. A549 cells were incubated with 1 μg/ml YW327.6S2 for indicated time, and cell surface Axl expression was determined by FACS (upper panel), and total protein expression by Western Blotting analysis (lower panel). G. YW327.6S2 inhibits Gas6-induced Axl phosphorylation & signaling. H1299 cells were cultured in serum free medium over night, pre-incubated with YW327.6S2 for 4 hrs, and treated with Gas6 for 30 minutes. Phosphorylated Axl was measured by ELISA (upper panel), and phosphorylated Akt by Western Blotting analysis (lower panel). H. YW327.6S2 inhibits Baf3Axl cell growth. Baf3Axl cells were grown in medium containing 200 ng/ml Gas6, and treated with YW327.6S2 at indicated concentrations for 72 hrs. Cell viability was measured by CellTiter Glo assay.

FIGS. 8A-F: YW327.6S2 attenuates A549 xenograft tumor growth and enhances the effect of anti-VEGF. A. Tumor growth curve. mAbs were administrated IP at 10 mg/kg (YW327.6S2 and isotype control antibody) or 1 mg/kg (anti-VEGF), twice a week, starting when the mean tumor size reached 100 $mm^3$ (day 0). Error bars represent standard error of the mean (n=10 for each group in each experiment). p=0.0003 (YW327.6S2 versus control), $p=10^{-11}$ (YW327.6S2 versus combination). B. Kaplan-Meier curve of various treatment groups. Mice were removed from the study when their tumor size reached 800 $mm^3$, and the animals remaining in each group (% remaining) were plotted. C. 12A11 enhances the effect of anti-VEGF. 12A11 and anti-VEGF was administrated IP at 30 mg/kg and 1 mg/kg, respectively, twice a week, starting when the mean tumor size reached 100 $mm^3$ (day 0). Error bars represent standard error of the mean (n=10 for each group in each experiment). p=0.006 (12A11 vs control); p=0.0001 (12A11 vs combination). D. YW327.6S2 down-regulates Axl expression. Mice were treated with YW327.6S2 at 10 mg/kg and tumors excised at the indicated time points. Cell lysates from tumors were analyzed by Western blot for Axl expression. E. YW327.6S2 induces apoptosis. Tumors treated with control or YW327.6S2 for 2 weeks were excised and CC3 IHC was performed to measure apoptosis. F. YW327.6S2 enhances the effect of anti-VEGF in reducing intra-tumoral vascular density. Tumors from mice treated as above in D were excised at 0 and 72 hr post dosing and tumor vasculature was visualized by staining with MECA32 immunohistochemistry and quantified by image analysis (expressed as microns square). Student's t test was performed for each pair ($p<0.05$ for control vs combination).

Figure 9A:
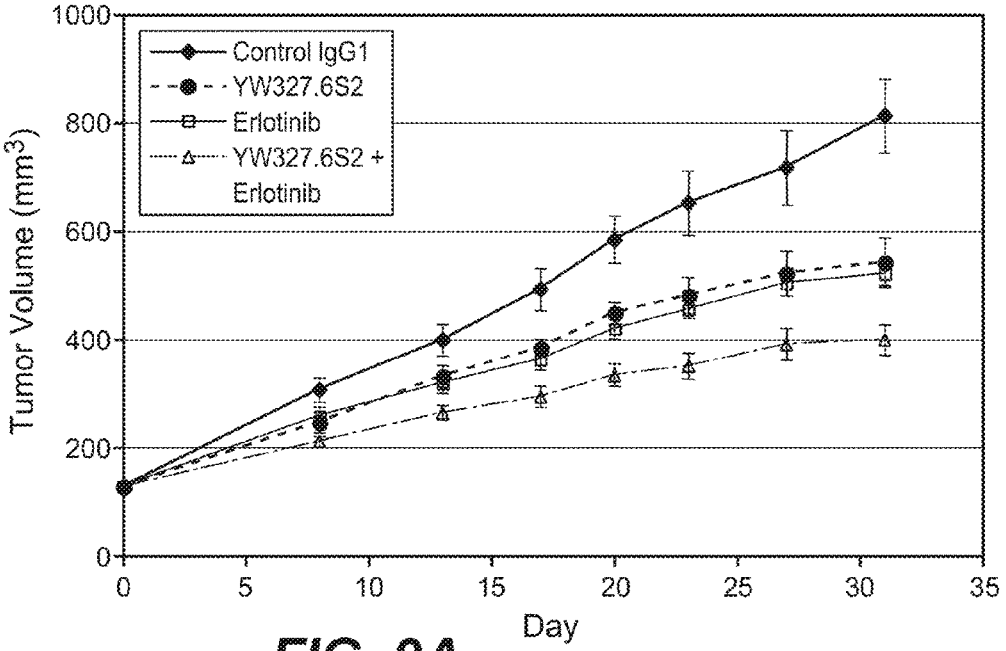
Figure 9B:
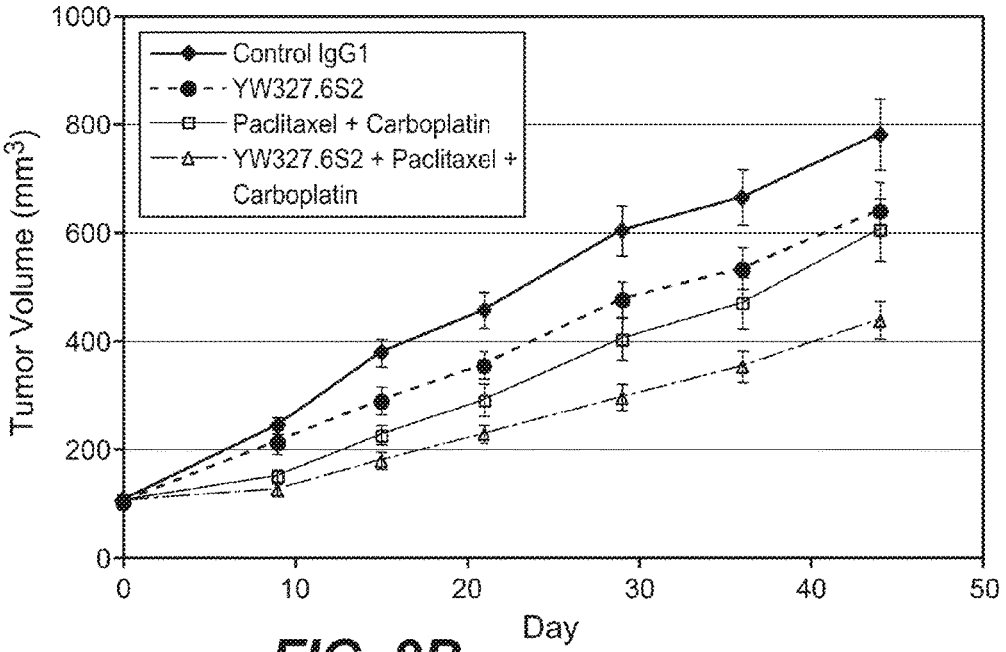

FIGS. 9A-B: YW327.6S2 enhances the anti-tumor effect of erlotinib and chemotherapy in A549 xenograft model. A. YW327.6S2 enhances the effect of erlotinib. Erlotinib was administered by oral gavage at 100 mg/kg/day. n=10 for each group. $p=1.7\times10^{-9}$ (YW327.6S2 versus control), $p=2.3\times10^{-10}$ (YW327.6S2 versus combination). B. YW327.6S2 enhances chemotherapy. Paclitaxel and carboplatin were administrated subcutaneously at 6.25 mg/kg/day for 5 days, and 100 mg/kg for a single dose at the beginning of the treatment (day 0), respectively. n=10 for each group. $p=3\times10^{-5}$ (YW327.6S2 versus control), $p=10^{-9}$ (chemotherapy versus control), $p=10^{-5}$ (combination versus chemotherapy alone).

FIGS. 10A-G: YW327.6S2 attenuates MDA-MB-231 xenograft tumor growth by modulating tumor stromal functions. A & B. YW327.6S2 but not 12A11 reduces MDA-MB-231 tumor growth and enhances the effect of anti-VEGF. mAbs were administrated IP at 20 mg/kg (YW327.6S2 and isotype control antibody), 30 mg/kg (12A11) and 2 mg/kg (anti-VEGF), twice a week, starting when the mean tumor size reached 100 $mm^3$ (day 0). Error bars represent standard error of the mean (n=10 for each group in each experiment). $p=8.5\times10^{-6}$ (YW327.6S2 versus control), $p=2.8\times10^{-8}$ (YW327.6S2 versus combination), p=0.05 (12A11 vs control), p=0.145 (anti-VEGF vs combination). C & D. YW327.6S2 down-regulates Axl expression. Mice bearing MDA-MB231 xenograft tumors (average size 500 $mm^3$) were treated with mAbs at 20 mg/kg and tumors excised at the indicated time points. Cell lysates from tumors were used in Western blot analysis for Axl expression. E. YW327.6S2 reduces the density of tumor-associated vasculature. Tumors from mice treated as above in C were excised at 0 hr and 1 week post dosing and tumor vasculature was visualized by staining with MECA32 immunohistochemistry and quantified by image analysis (expressed as microns square). Student's t test was performed for each pair ($p<0.05$ for YW327.6S2 vs control, anti-VEGF vs control, and anti-VEGF vs combination). F. Axl is highly expressed in infiltrating macrophages of primary human breast cancer. Immunohistochemistry was used to examine 79 primary tumors. 21% of these tumors express high levels of Axl in the infiltrating macrophages. Macrophages were identified by staining with anti-CD68, and expression of Axl on macrophages was determined by anti-Axl/CD68 dual IHC. Serial sections were used. G. YW327.6S2 inhibits inflammatory cytokine/chemokine secretion from tumor-associated macrophages. Mice bearing MDA-MB231 xenograft tumors (average size 500 $mm^3$) were treated with control antibody, YW327.6S2 or 12A11 at 20 mg/kg and tumors excised after I week treatment. Tumor associated macrophages were isolated by sorting for F4/80 positive cells and cultured overnight. Cytokines and chemokines secreted into the medium were measured using the Bio-Plea mouse cytokine assay kit.

Figure 11A:
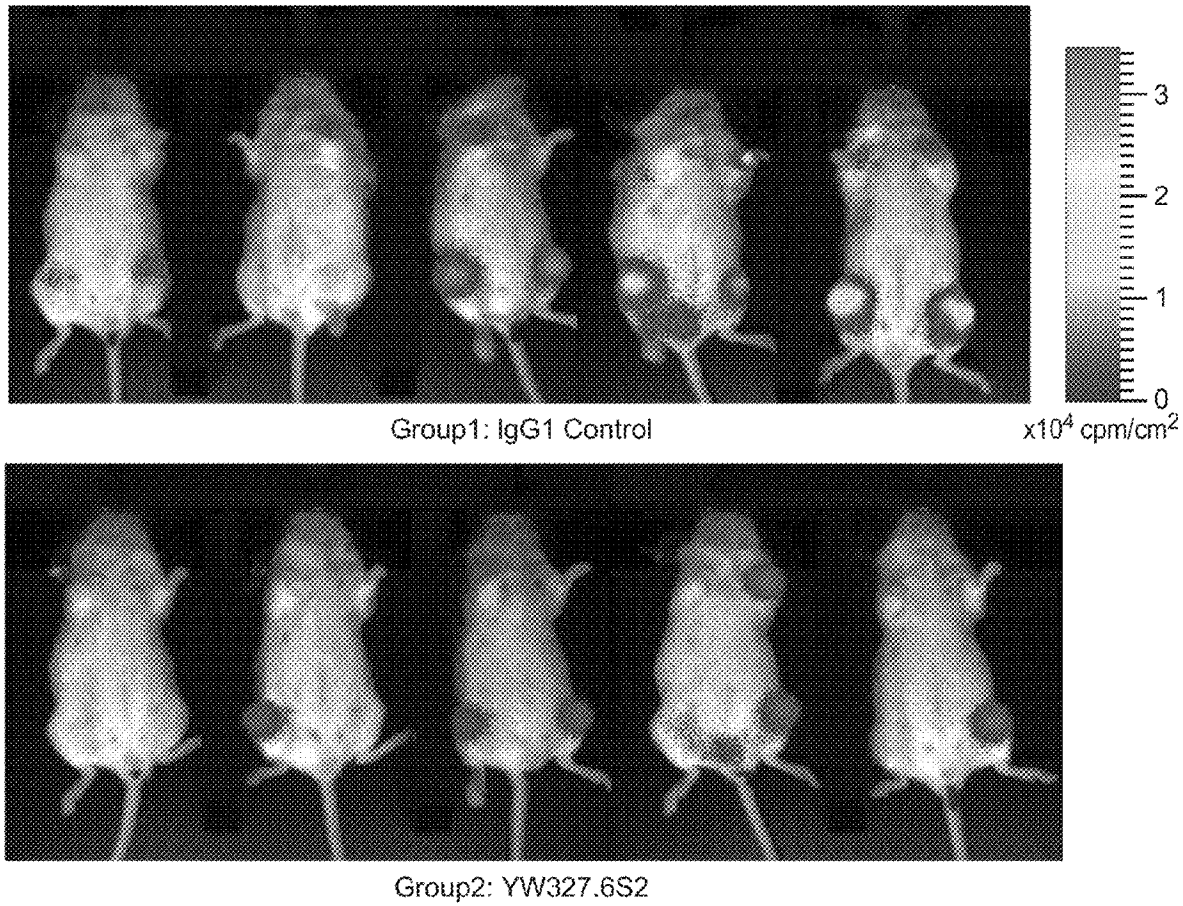
Figure 11B:
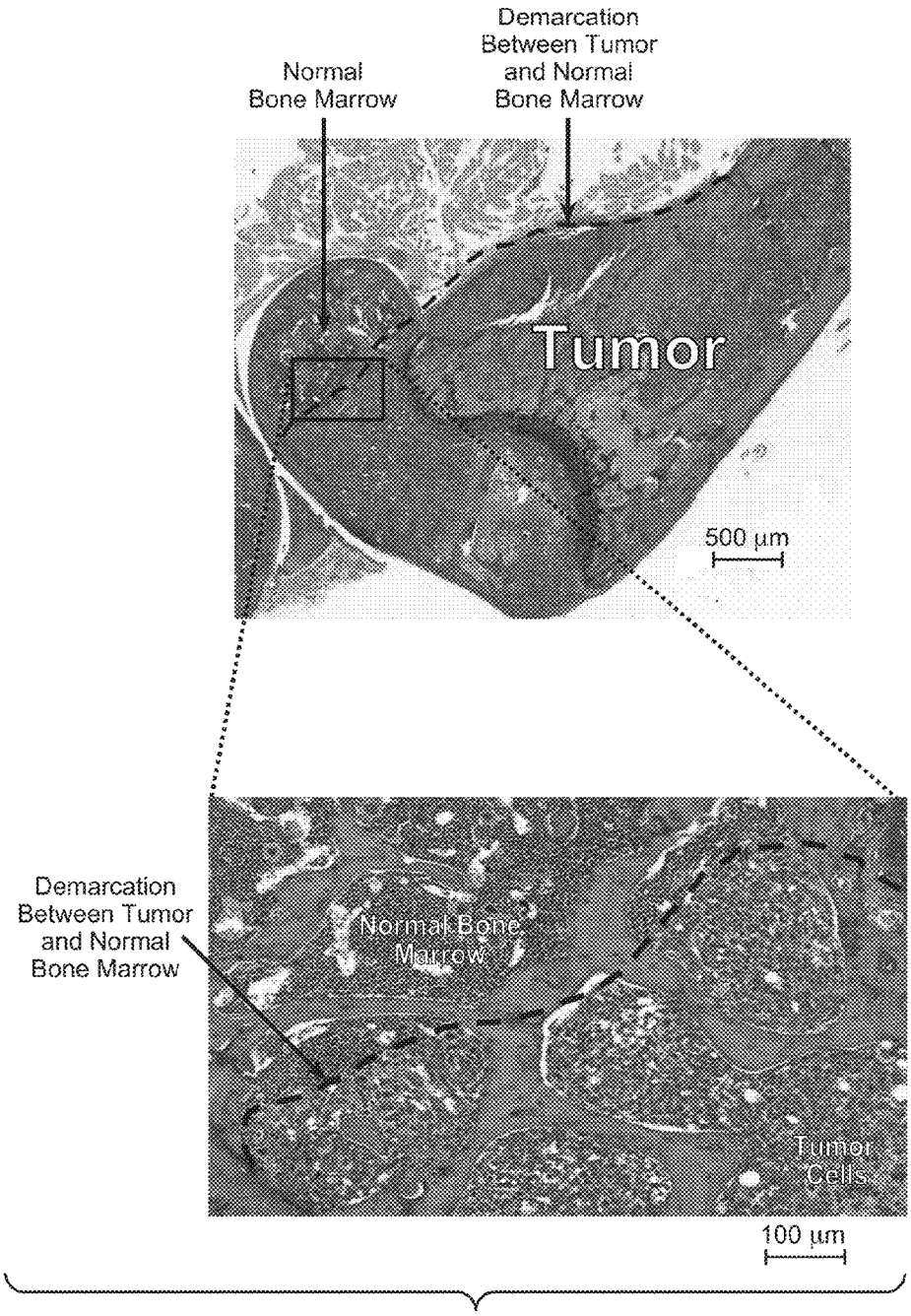

FIGS. 11A-B: YW327.6S2 reduces metastasis of MDA-MB-231 breast cancer cells to the bone. A. Bioluminescence imaging 4 weeks after tail vein injection of tumor cells. Mice were injected intraperitoneally (i.p.) with 200 μL of 25 mg/ml D-luciferin (Invitrogen) in PBS and were anesthetized during imaging using isoflurane via nose cone. Bioluminescence images were acquired on the Photon Imager (Biospace Lab, Paris, France) that has an intensified charge-coupled device camera. B. H & E staining of the tibia sections. Tissues were collected at the end of the experiments and fixed in 4% formaldehyde, sectioned and stained with H & E. The circle in the upper panel shows tumor cells invading the bone. The lower panel shows details of neoplastic cells in the bone marrow.

FIG. 12: An exemplary human Axl sequence of RefSeq NM_001699. (SEQ ID NO:165).

DETAILED DESCRIPTION OF EMBODIMENTS OF THE INVENTION

I. Definitions

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

An "angiogenic disorder" refers to any dysregulation of angiogenesis, including both non-neoplastic and neoplastic conditions. Neoplastic conditions include but are not limited those described below (see, e.g., "Cancer"). Non-neoplastic disorders include but are not limited to undesired or aberrant hypertrophy, arthritis, rheumatoid arthritis (RA), psoriasis, psoriatic plaques, sarcoidosis, atherosclerosis, atherosclerotic plaques, diabetic and other proliferative retinopathies including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, chronic inflammation, lung inflammation, acute lung injury/ARDS, sepsis, primary pulmonary hypertension, malignant pulmonary effusions, cerebral edema (e.g., associated with acute stroke/closed head injury/trauma), synovial inflammation, pannus formation in RA, myositis ossificans, hypertropic bone formation, osteoarthritis (OA), refractory ascites, polycystic ovarian disease, endometriosis, 3rd spacing of fluid diseases (pancreatitis, compartment syndrome, burns, bowel disease), uterine fibroids, premature labor, chronic inflammation such as IBD (Crohn's disease and ulcerative colitis), renal allograft rejection, inflammatory bowel disease, nephrotic syndrome, undesired or aberrant tissue mass growth (non-cancer), hemophilic joints, hypertrophic scars, inhibition of hair growth, Osler-Weber syndrome, pyogenic granuloma retrolental fibroplasias, scleroderma, trachoma, vascular adhesions, synovitis, dermatitis, preeclampsia, ascites, pericardial effusion (such as that associated with pericarditis), and pleural effusion.

An "anti-angiogenic agent" refers to a compound which blocks, or interferes with to some degree, the development of blood vessels. An anti-angiogenic agent may, for instance, be a small molecule or antibody that binds to a growth factor or growth factor receptor involved in promoting angiogenesis. In one embodiment, an anti-angiogenic agent is an antibody that binds to vascular endothelial growth factor (VEGF), such as bevacizumab (AVASTIN®).

The terms "anti-Axl antibody" and "an antibody that binds to Axl" refer to an antibody that is capable of binding Axl with sufficient affinity such that the antibody is useful as a diagnostic and/or therapeutic agent in targeting Axl. In one embodiment, the extent of binding of an anti-Axl antibody to an unrelated, non-Axl protein is less than about 10% of the binding of the antibody to Axl as measured, e.g., by a radioimmunoassay (RIA). In certain embodiments, an antibody that binds to Axl has a dissociation constant (Kd) of ≤1 μM, ≤100 nM, ≤10 nM, ≤1 nM, ≤0.1 nM, ≤0.01 nM, or ≤0.001 nM (e.g. $10^{-8}$M or less, e.g. from $10^{-8}$M to $10^{-13}$M, e.g., from $10^{-9}$M to $10^{-13}$ M). In certain embodiments, an anti-Axl antibody binds to an epitope of Axl that is conserved among Axl from different species.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, $F(ab')_2$; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "Axl," as used herein, refers to any native Axl from any vertebrate source, including mammals such as primates (e.g. humans) and rodents (e.g., mice and rats), unless otherwise indicated. The term encompasses "full-length," unprocessed Axl as well as any form of Axl that results from processing in the cell. The term also encompasses naturally occurring variants of Axl, e.g., splice variants or allelic variants. The amino acid sequence of an exemplary human Axl is shown in FIG. 12.

"Axl activation" refers to activation, or phosphorylation, of the Axl receptor. Generally, Axl activation results in signal transduction (e.g. that caused by an intracellular kinase domain of an Axl receptor phosphorylating tyrosine residues in Axl or a substrate polypeptide). Axl activation may be mediated by Axl ligand (Gas6) binding to an Axl receptor of interest. Gas6 binding to Axl may activate a kinase domain of Axl and thereby result in phosphorylation of tyrosine residues in the Axl and/or phosphorylation of tyrosine residues in additional substrate polypeptides(s).

The terms "cancer" and "cancerous" refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

The terms "cell proliferative disorder" and "proliferative disorder" refer to disorders that are associated with some degree of abnormal cell proliferation. In one embodiment, the cell proliferative disorder is cancer.

A "chemotherapeutic agent" refers to a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaI1 (see, e.g., Nicolaou et al., Angew. Chem. Intl. Ed. Engl., 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2'-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chloranbucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylornithine (DMF®); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g. celecoxib or etoricoxib), proteosome inhibitor (e.g. PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors (see definition below); tyrosine kinase inhibitors (see definition below); serine-threonine kinase inhibitors such as rapamycin (sirolimus, RAPAMUNE®); farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents as defined herein include "antihormonal agents" or "endocrine therapeutics" which act to regulate, reduce, block, or inhibit the effects of hormones that can promote the growth of cancer. They may be hormones themselves, including, but not limited to: antiestrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure antiestrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and non-steroidal aromatase inhibitors such as anastrazole (ARIMIDEX®), letrozole (FEMARA®) and aminoglutethimide, and other aromatase inhibitors include vorozole (RIVISOR®), megestrol acetate (MEGASE®), fadrozole, and 4(5)-imidazoles; lutenizing hormone-releaseing hormone agonists, including leuprolide (LUPRON® and ELIGARD®), goserelin, buserelin, and tripterelin; sex steroids, including progestines such as megestrol acetate and medroxyprogesterone acetate, estrogens such as diethylstilbestrol and premarin, and androgens/retinoids such as fluoxymesterone, all transretionic acid and fenretinide; onapristone; anti-progesterones; estrogen receptor down-regulators (ERDs); anti-androgens such as flutamide, nilutamide and bicalutamide; and pharmaceutically acceptable salts, acids or derivatives of any of the above; as well as combinations of two or more of the above.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called $\alpha$, $\delta$, $\epsilon$, $\gamma$, and $\mu$, respectively.

The term "constitutive" as used herein, as for example applied to receptor kinase activity, refers to continuous signaling activity of a receptor that is not dependent on the presence of a ligand or other activating molecules. Depending on the nature of the receptor, all of the activity may be constitutive or the activity of the receptor may be further activated by the binding of other molecules (e.g. ligands). Cellular events that lead to activation of receptors are well known among those of ordinary skill in the art. For example, activation may include oligomerization, e.g., dimerization, trimerization, etc., into higher order receptor complexes. Complexes may comprise a single species of protein, i.e., a homomeric complex. Alternatively, complexes may comprise at least two different protein species, i.e., a heteromeric complex. Complex formation may be caused by, for example, overexpression of normal or mutant forms of receptor on the surface of a cell. Complex formation may also be caused by a specific mutation or mutations in a receptor.

The term "cytostatic agent" refers to a compound or composition which arrests growth of a cell either in vitro or in vivo. Thus, a cytostatic agent may be one which significantly reduces the percentage of cells in S phase. Further examples of cytostatic agents include agents that block cell cycle progression by inducing G0/G1 arrest or M-phase arrest. The humanized anti-Her2 antibody trastuzumab (HERCEPTIN®) is an example of a cytostatic agent that induces G0/G1 arrest. Classical M-phase blockers include the vincas (vincristine and vinblastine), taxanes, and topoisomerase II inhibitors such as doxorubicin, epirubicin, daunorubicin, etoposide, and bleomycin. Certain agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in Mendelsohn and Israel, eds., The Molecular Basis of Cancer, Chapter 1, entitled "Cell cycle regulation, oncogenes, and antineoplastic drugs" by Murakami et al. (W.B. Saunders, Philadelphia, 1995), e.g., p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

The term "cytotoxic agent" as used herein refers to a substance that inhibits or prevents a cellular function and/or causes cell death or destruction. Cytotoxic agents include, but are not limited to radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, J. Mol. Biol. 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., Sequences of Proteins of Immunological Interest, 5th Ed. Public Health Service, National Institutes of Health, Bethesda, Md. (1991) .) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, Front. Biosci. 13:1619-1633 (2008).) Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

"Inhibiting cell growth or proliferation" means decreasing a cell's growth or proliferation by at least 10%, 20%, 30%, 40%, 50%, 60%, 70%, 80%, 90%, 95%, or 100%, and includes inducing cell death.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., J. Chromatogr. B 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-Axl antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "ligand-independent" as used herein, as for example applied to receptor signaling activity, refers to signaling activity that is not dependent on the presence of a ligand. A receptor having ligand-independent kinase activity will not necessarily preclude the binding of ligand to that receptor to produce additional activation of the kinase activity.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject., A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "tumor" refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive as referred to herein.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. Kuby Immunology, 6th ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150:880-887 (1993); Clarkson et al., Nature 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

A "VH subgroup III consensus framework" comprises the consensus sequence obtained from the amino acid sequences in variable heavy subgroup III of Kabat et al. In one embodiment, the VH subgroup III consensus framework amino acid sequence comprises at least a portion or all of each of the following sequences: EVQLVESGGGLVQPGGSLRLSCAAS (SEQ ID NO:122)-H1-WVRQAPGKGLEWV (SEQ ID NO:123)-H2-RFTISRDNSKNTLYLQMNSLRAEDTAVYYC (SEQ ID NO:124)-H3-WGQGTLVTVSS (SEQ ID NO:125).

A "VL subgroup I consensus framework" comprises the consensus sequence obtained from the amino acid sequences in variable light kappa subgroup I of Kabat et al. In one embodiment, the VH subgroup I consensus framework amino acid sequence comprises at least a portion or all of each of the following sequences: DIQMTQSPSSLSASVGDRVTITC (SEQ ID NO:126)-L1-WYQQKPGKAPKLLIY (SEQ ID NO:127)-L2-GVPSRFSGSGSGTDFTLTISSLQPEDFATYYC (SEQ ID NO:128)-L3-FGQGTKVEIK (SEQ ID NO:129).

II. Compositions and Methods

In one aspect, the invention is based, in part, on the identification of a variety of Axl binding agents (such as antibodies and fragments thereof). Axl presents an important and advantageous therapeutic target, and the invention provides compositions and methods based on binding of the agents to Axl. Axl binding agents of the invention, as described herein, provide important therapeutic and diagnostic agents for use in targeting pathological conditions associated with expression and/or activity of the Axl signaling pathways. In certain embodiments, antibodies that bind to Axl are provided. Antibodies of the invention are useful, e.g., for the diagnosis or treatment of cancer.

A. Exemplary Anti-Axl Antibodies

In one aspect, the invention provides isolated antibodies that bind to Axl. In certain embodiments, an anti-Axl antibody binds human Axl with an affinity of ≤550 pM, and in some embodiments, binds mouse Axl with an affinity of ≤1 nM. In some embodiments, an anti-Axl antibody binds human and mouse Axl.

In some embodiments, an anti-Axl antibody induces down-regulation of Axl receptor expression on a cell surface (e.g. a tumor cell surface). In some embodiments, cell surface Axl expression is reduced to less than 80% of Axl cell surface expression in the absence of Axl antibody treatment. In some embodiments, cell surface expression is reduced to less than 70%, less than 60%, less than 50% or less than 40% of Axl cell surface expression in the absence of Axl antibody treatment. In some embodiments, total Axl expression in a cell (e.g., a tumor cell) is reduced to less than 80% of total Axl expression in the absence of Axl antibody treatment. In some embodiments, total Axl expression is reduced to less than 70%, less than 60%, less than 50% or less than 40% of total Axl expression in the absence of Axl antibody treatment. In some embodiments, down-regulation of Axl expression occurs rapidly and lasts for at least 24 hours.

In some embodiments, an anti-Axl antibody inhibits constitutive Axl activity.

In some embodiments, an anti-Axl antibody does not significantly cross-react with Sky or Mer. In some embodiments, an anti-Axl antibody does not significantly bind to Sky or Mer and binds human and mouse Axl.

In some embodiments, an anti-Axl antibody inhibits Axl activity.

In some embodiments, an anti-Axl antibody promotes apoptosis of a cell, e.g., a tumor cell, such as a A549 tumor cell. In some embodiments, an anti-Axl antibody inhibits Axl ligand (e.g., Gas6) binding to Axl. In some embodiments, an anti-Axl antibody inhibits Axl downstream signaling. In some embodiments, an anti-Axl antibody inhibits Gas-6 dependent cell proliferation. In some embodiments, an anti-Axl antibody inhibits inflammatory cytokine expression from tumor-associated macrophages. In some embodiments, an anti-Axl antibody inhibits tumor growth and/or metastasis by modulating tumor stromal function.

In some embodiments, an anti-Axl antibody binds a polypeptide comprising, consisting essentially of or consisting of the following amino acid sequence:

(SEQ ID NO: 111)
MAWRCPRMGRVPLAWCLALCGWACMAPRGTQAEESPFVGNPGNITGARGL
TGTLRCQLQVQGEPPEVHWLRDGQILELADSTQTQVPLGEDEQDDWIVVS
QLRITSLQLSDTGQYQCLVFLGHQTFVSQPGYVG.

In some embodiments, an anti-Axl antibody binds a polypeptide comprising, consisting essentially of or consisting of the following amino acid sequence:

(SEQ ID NO: 130)
ITVLPQQPRNLHLVSRQPTELEVAWTPGLSGIYPLTHCTLQAVLSDDGMG
IQAGEPDPPEEPLTSQASVPPHQLRLGSLHPHTPYHIRVACTSSQGPSSW
THWL.

In some embodiments, the antibody binds a polypeptide comprising, consisting essentially of or consisting of amino acid numbers 1-122 of the mature human Axl amino acid sequence.

In some embodiments, the antibody binds a polypeptide comprising, consisting essentially of or consisting of amino acid numbers 221-234 of the mature human Axl amino acid sequence.

In some embodiments, an anti-Axl antibody binds an amino acid sequence having at least 70%, 80%, 90%, 95%, 98% sequence identity or similarity with the sequence (SEQ ID NO: 111)
MAWRCPRMGRVPLAWCLALCGWACMAPRGTQAEESPFVGNPGNITGARGL
TGTLRCQLQVQGEPPEVHWLRDGQILELADSTQTQVPLGEDEQDDWIVVS
QLRITSLQLSDTGQYQCLVFLGHQTFVSQPGYVG.

In some embodiments, an anti-Axl antibody binds an amino acid sequence having at least 70%, 80%, 90%, 95%, 98% sequence identity or similarity with the sequence (SEQ ID NO: 130)
ITVLPQQPRNLHLVSRQPTELEVAWTPGLSGIYPLTHCTLQAVLSDDGMG
IQAGEPDPPEEPLTSQASVPPHQLRLGSLHPHTPYHIRVACTSSQGPSSW
THWL.

In one aspect, the invention provides an anti-Axl antibody comprising at least one, two, three, four, five, or six HVRs selected from (a) HVR-H1 comprising the amino acid sequence of SEQ ID NO:1; (b) HVR-H2 comprising the amino acid sequence of SEQ ID NO:2; (c) HVR-H3 comprising the amino acid sequence of SEQ ID NO:3; (d) HVR-L1 comprising the amino acid sequence of SEQ ID NO:4; (e) HVR-L2 comprising the amino acid sequence of SEQ ID NO:5; and (f) HVR-L3 comprising the amino acid sequence of SEQ ID NO:6.

In one aspect, the invention provides an anti-Axl antibody comprising at least one, two, three, four, five, or six HVRs selected from (a) HVR-H1 comprising the amino acid sequence of SEQ ID NO:7; (b) HVR-H2 comprising the amino acid sequence of SEQ ID NO:8; (c) HVR-H3 comprising the amino acid sequence of SEQ ID NO:9; (d) HVR-L1 comprising the amino acid sequence of SEQ ID NO:10; (e) HVR-L2 comprising the amino acid sequence of SEQ ID NO:11; and (f) HVR-L3 comprising the amino acid sequence of SEQ ID NO:12.

In one aspect, the invention provides an anti-Axl antibody comprising at least one, two, three, four, five, or six HVRs selected from (a) HVR-H1 comprising the amino acid sequence of SEQ ID NO:13; (b) HVR-H2 comprising the amino acid sequence of SEQ ID NO:14; (c) HVR-H3 comprising the amino acid sequence of SEQ ID NO:15; (d) HVR-L1 comprising the amino acid sequence of SEQ ID NO:16; (e) HVR-L2 comprising the amino acid sequence of SEQ ID NO:17; and (f) HVR-L3 comprising the amino acid sequence of SEQ ID NO:18.

In one aspect, the invention provides an anti-Axl antibody comprising at least one, two, three, four, five, or six HVRs selected from (a) HVR-H1 comprising the amino acid sequence of SEQ ID NO:19; (b) HVR-H2 comprising the amino acid sequence of SEQ ID NO:20; (c) HVR-H3 comprising the amino acid sequence of SEQ ID NO:21; (d) HVR-L1 comprising the amino acid sequence of SEQ ID NO:22; (e) HVR-L2 comprising the amino acid sequence of SEQ ID NO:23; and (f) HVR-L3 comprising the amino acid sequence of SEQ ID NO:24.

In one aspect, the invention provides an anti-Axl antibody comprising at least one, two, three, four, five, or six HVRs selected from (a) HVR-H1 comprising the amino acid sequence of SEQ ID NO:25; (b) HVR-H2 comprising the amino acid sequence of SEQ ID NO:26; (c) HVR-H3 comprising the amino acid sequence of SEQ ID NO:27; (d) HVR-L1 comprising the amino acid sequence of SEQ ID NO:28; (e) HVR-L2 comprising the amino acid sequence of SEQ ID NO:29; and (f) HVR-L3 comprising the amino acid sequence of SEQ ID NO:30.

In one aspect, the invention provides an anti-Axl antibody comprising at least one, two, three, four, five, or six HVRs selected from (a) HVR-H1 comprising the amino acid sequence of SEQ ID NO:31; (b) HVR-H2 comprising the amino acid sequence of SEQ ID NO:32; (c) HVR-H3 comprising the amino acid sequence of SEQ ID NO:33; (d) HVR-L1 comprising the amino acid sequence of SEQ ID NO:34; (e) HVR-L2 comprising the amino acid sequence of SEQ ID NO:35; and (f) HVR-L3 comprising the amino acid sequence of SEQ ID NO:36.

In one aspect, the invention provides an anti-Axl antibody comprising at least one, two, three, four, five, or six HVRs selected from (a) HVR-H1 comprising the amino acid sequence of SEQ ID NO:37; (b) HVR-H2 comprising the amino acid sequence of SEQ ID NO:38; (c) HVR-H3 comprising the amino acid sequence of SEQ ID NO:39; (d) HVR-L1 comprising the amino acid sequence of SEQ ID NO:40; (e) HVR-L2 comprising the amino acid sequence of SEQ ID NO:41; and (f) HVR-L3 comprising the amino acid sequence of SEQ ID NO:42.

In one aspect, the invention provides an anti-Axl antibody comprising at least one, two, three, four, five, or six HVRs selected from (a) HVR-H1 comprising the amino acid sequence of SEQ ID NO:43; (b) HVR-H2 comprising the amino acid sequence of SEQ ID NO:44; (c) HVR-H3 comprising the amino acid sequence of SEQ ID NO:45; (d) HVR-L1 comprising the amino acid sequence of SEQ ID NO:46; (e) HVR-L2 comprising the amino acid sequence of SEQ ID NO:47; and (f) HVR-L3 comprising the amino acid sequence of SEQ ID NO:48.

In one aspect, the invention provides an anti-Axl antibody comprising at least one, two, three, four, five, or six HVRs selected from (a) HVR-H1 comprising the amino acid sequence of SEQ ID NO:49; (b) HVR-H2 comprising the amino acid sequence of SEQ ID NO:50; (c) HVR-H3 comprising the amino acid sequence of SEQ ID NO:51; (d) HVR-L1 comprising the amino acid sequence of SEQ ID NO:52; (e) HVR-L2 comprising the amino acid sequence of SEQ ID NO:53; and (f) HVR-L3 comprising the amino acid sequence of SEQ ID NO:54.

In one aspect, the invention provides an anti-Axl antibody comprising at least one, two, three, four, five, or six HVRs selected from (a) HVR-H1 comprising the amino acid sequence of SEQ ID NO:55; (b) HVR-H2 comprising the amino acid sequence of SEQ ID NO:56; (c) HVR-H3 comprising the amino acid sequence of SEQ ID NO:57; (d) HVR-L1 comprising the amino acid sequence of SEQ ID NO:58; (e) HVR-L2 comprising the amino acid sequence of SEQ ID NO:59; and (f) HVR-L3 comprising the amino acid sequence of SEQ ID NO:60.

In one aspect, the invention provides an anti-Axl antibody comprising at least one, two, three, four, five, or six HVRs selected from (a) HVR-H1 comprising the amino acid sequence of SEQ ID NO:61; (b) HVR-H2 comprising the amino acid sequence of SEQ ID NO:62; (c) HVR-H3 comprising the amino acid sequence of SEQ ID NO:63; (d) HVR-L1 comprising the amino acid sequence of SEQ ID NO:64; (e) HVR-L2 comprising the amino acid sequence of SEQ ID NO:65; and (f) HVR-L3 comprising the amino acid sequence of SEQ ID NO:66.

In one aspect, the invention provides an anti-Axl antibody comprising at least one, two, three, four, five, or six HVRs selected from (a) HVR-H1 comprising the amino acid sequence of SEQ ID NO:67; (b) HVR-H2 comprising the amino acid sequence of SEQ ID NO:68; (c) HVR-H3 comprising the amino acid sequence of SEQ ID NO:69; (d) HVR-L1 comprising the amino acid sequence of SEQ ID NO:70; (e) HVR-L2 comprising the amino acid sequence of SEQ ID NO:71; and (f) HVR-L3 comprising the amino acid sequence of SEQ ID NO:72.

In one aspect, the invention provides an anti-Axl antibody comprising at least one, two, three, four, five, or six HVRs selected from (a) HVR-H1 comprising the amino acid sequence of SEQ ID NO:73; (b) HVR-H2 comprising the amino acid sequence of SEQ ID NO:74; (c) HVR-H3 comprising the amino acid sequence of SEQ ID NO:75; (d) HVR-L1 comprising the amino acid sequence of SEQ ID NO:76; (e) HVR-L2 comprising the amino acid sequence of SEQ ID NO:77; and (f) HVR-L3 comprising the amino acid sequence of SEQ ID NO:78.

In one aspect, the invention provides an anti-Axl antibody comprising at least one, two, three, four, five, or six HVRs selected from (a) HVR-H1 comprising the amino acid sequence of SEQ ID NO:79; (b) HVR-H2 comprising the amino acid sequence of SEQ ID NO:80; (c) HVR-H3 comprising the amino acid sequence of SEQ ID NO:81; (d) HVR-L1 comprising the amino acid sequence of SEQ ID NO:82; (e) HVR-L2 comprising the amino acid sequence of SEQ ID NO:83; and (f) HVR-L3 comprising the amino acid sequence of SEQ ID NO:84.

In one aspect, the invention provides an anti-Axl antibody comprising at least one, two, three, four, five, or six HVRs selected from (a) HVR-H1 comprising the amino acid sequence of SEQ ID NO:85; (b) HVR-H2 comprising the amino acid sequence of SEQ ID NO:86; (c) HVR-H3 comprising the amino acid sequence of SEQ ID NO:87; (d) HVR-L1 comprising the amino acid sequence of SEQ ID NO:88; (e) HVR-L2 comprising the amino acid sequence of SEQ ID NO:89; and (f) HVR-L3 comprising the amino acid sequence of SEQ ID NO:90.

In one aspect, the invention provides an anti-Axl antibody comprising at least one, two, three, four, five, or six HVRs selected from (a) HVR-H1 comprising the amino acid sequence of SEQ ID NO:91; (b) HVR-H2 comprising the amino acid sequence of SEQ ID NO:92; (c) HVR-H3 comprising the amino acid sequence of SEQ ID NO:93; (d) HVR-L1 comprising the amino acid sequence of SEQ ID NO:94; (e) HVR-L2 comprising the amino acid sequence of SEQ ID NO:95; and (f) HVR-L3 comprising the amino acid sequence of SEQ ID NO:96.

In one aspect, the invention provides an anti-Axl antibody comprising at least one, two, three, four, five, or six HVRs selected from (a) HVR-H1 comprising the amino acid sequence of SEQ ID NO:97; (b) HVR-H2 comprising the amino acid sequence of SEQ ID NO:98; (c) HVR-H3 comprising the amino acid sequence of SEQ ID NO:99; (d) HVR-L1 comprising the amino acid sequence of SEQ ID NO:100; (e) HVR-L2 comprising the amino acid sequence of SEQ ID NO:101; and (0 HVR-L3 comprising the amino acid sequence of SEQ ID NO:102.

In one aspect, the invention provides an anti-Axl antibody comprising at least one, two, or all three VH HVR sequences selected from (a) HVR-H1 comprising the amino acid sequence of SEQ ID NO:1; (b) HVR-H2 comprising the amino acid sequence of SEQ ID NO:2; and (c) HVR-H3 comprising the amino acid sequence of SEQ ID NO:3.

In one aspect, the invention provides an anti-Axl antibody comprising at least one, two, or all three VH HVR sequences selected from (a) HVR-H1 comprising the amino acid sequence of SEQ ID NO:7; (b) HVR-H2 comprising the amino acid sequence of SEQ ID NO:8; and (c) HVR-H3 comprising the amino acid sequence of SEQ ID NO:9.

In one aspect, the invention provides an anti-Axl antibody comprising at least one, two, or all three VH HVR sequences selected from (a) HVR-H1 comprising the amino acid sequence of SEQ ID NO:13; (b) HVR-H2 comprising the amino acid sequence of SEQ ID NO:14; and (c) HVR-H3 comprising the amino acid sequence of SEQ ID NO:15.

In one aspect, the invention provides an anti-Axl antibody comprising at least one, two, or all three VH HVR sequences selected from (a) HVR-H1 comprising the amino acid sequence of SEQ ID NO:19; (b) HVR-H2 comprising the amino acid sequence of SEQ ID NO:20; and (c) HVR-H3 comprising the amino acid sequence of SEQ ID NO:21.

In one aspect, the invention provides an anti-Axl antibody comprising at least one, two, or all three VH HVR sequences selected from (a) HVR-H1 comprising the amino acid sequence of SEQ ID NO:25; (b) HVR-H2 comprising the amino acid sequence of SEQ ID NO:26; and (c) HVR-H3 comprising the amino acid sequence of SEQ ID NO:27.

In one aspect, the invention provides an anti-Axl antibody comprising at least one, two, or all three VH HVR sequences selected from (a) HVR-H1 comprising the amino acid sequence of SEQ ID NO:31; (b) HVR-H2 comprising the amino acid sequence of SEQ ID NO:32; and (c) HVR-H3 comprising the amino acid sequence of SEQ ID NO:33.

In one aspect, the invention provides an anti-Axl antibody comprising at least one, two, or all three VH HVR sequences selected from (a) HVR-H1 comprising the amino acid sequence of SEQ ID NO:37; (b) HVR-H2 comprising the amino acid sequence of SEQ ID NO:38; and (c) HVR-H3 comprising the amino acid sequence of SEQ ID NO:39.

In one aspect, the invention provides an anti-Axl antibody comprising at least one, two, or all three VH HVR sequences selected from (a) HVR-H1 comprising the amino acid sequence of SEQ ID NO:43; (b) HVR-H2 comprising the amino acid sequence of SEQ ID NO:44; and (c) HVR-H3 comprising the amino acid sequence of SEQ ID NO:45.

In one aspect, the invention provides an anti-Axl antibody comprising at least one, two, or all three VH HVR sequences selected from (a) HVR-H1 comprising the amino acid sequence of SEQ ID NO:49; (b) HVR-H2 comprising the amino acid sequence of SEQ ID NO:50; and (c) HVR-H3 comprising the amino acid sequence of SEQ ID NO:51.

In one aspect, the invention provides an anti-Axl antibody comprising at least one, two, or all three VH HVR sequences selected from (a) HVR-H1 comprising the amino acid sequence of SEQ ID NO:55; (b) HVR-H2 comprising the amino acid sequence of SEQ ID NO:56; and (c) HVR-H3 comprising the amino acid sequence of SEQ ID NO:57.

In one aspect, the invention provides an anti-Axl antibody comprising at least one, two, or all three VH HVR sequences selected from (a) HVR-H1 comprising the amino acid sequence of SEQ ID NO:61; (b) HVR-H2 comprising the amino acid sequence of SEQ ID NO:62; and (c) HVR-H3 comprising the amino acid sequence of SEQ ID NO:63.

In one aspect, the invention provides an anti-Axl antibody comprising at least one, two, or all three VH HVR sequences selected from (a) HVR-H1 comprising the amino acid sequence of SEQ ID NO:67; (b) HVR-H2 comprising the amino acid sequence of SEQ ID NO:68; and (c) HVR-H3 comprising the amino acid sequence of SEQ ID NO:69.

In one aspect, the invention provides an anti-Axl antibody comprising at least one, two, or all three VH HVR sequences selected from (a) HVR-H1 comprising the amino acid sequence of SEQ ID NO:73; (b) HVR-H2 comprising the amino acid sequence of SEQ ID NO:74; and (c) HVR-H3 comprising the amino acid sequence of SEQ ID NO:75.

In one aspect, the invention provides an anti-Axl antibody comprising at least one, two, or all three VH HVR sequences selected from (a) HVR-H1 comprising the amino acid sequence of SEQ ID NO:79; (b) HVR-H2 comprising the amino acid sequence of SEQ ID NO:80; and (c) HVR-H3 comprising the amino acid sequence of SEQ ID NO:81.

In one aspect, the invention provides an anti-Axl antibody comprising at least one, two, or all three VH HVR sequences selected from (a) HVR-H1 comprising the amino acid sequence of SEQ ID NO:85; (b) HVR-H2 comprising the amino acid sequence of SEQ ID NO:86; and (c) HVR-H3 comprising the amino acid sequence of SEQ ID NO:87.

In one aspect, the invention provides an anti-Axl antibody comprising at least one, two, or all three VH HVR sequences selected from (a) HVR-H1 comprising the amino acid sequence of SEQ ID NO:91; (b) HVR-H2 comprising the amino acid sequence of SEQ ID NO:92; and (c) HVR-H3 comprising the amino acid sequence of SEQ ID NO:93.

In one aspect, the invention provides an anti-Axl antibody comprising at least one, two, or all three VH HVR sequences selected from (a) HVR-H1 comprising the amino acid sequence of SEQ ID NO:97; (b) HVR-H2 comprising the amino acid sequence of SEQ ID NO:98; and (c) HVR-H3 comprising the amino acid sequence of SEQ ID NO:99.

In one embodiment, the antibody comprises HVR-H3 comprising the amino acid sequence of SEQ ID NO:3. In one embodiment, the antibody comprises HVR-H3 comprising the amino acid sequence of SEQ ID NO:9. In one embodiment, the antibody comprises HVR-H3 comprising the amino acid sequence of SEQ ID NO:15. In one embodiment, the antibody comprises HVR-H3 comprising the amino acid sequence of SEQ ID NO:21. In one embodiment, the antibody comprises HVR-H3 comprising the amino acid sequence of SEQ ID NO:27. In one embodiment, the antibody comprises HVR-H3 comprising the amino acid sequence of SEQ ID NO:33. In one embodiment, the antibody comprises HVR-H3 comprising the amino acid sequence of SEQ ID NO:39. In one embodiment, the antibody comprises HVR-H3 comprising the amino acid sequence of SEQ ID NO:45. In one embodiment, the antibody comprises HVR-H3 comprising the amino acid sequence of SEQ ID NO:51. In one embodiment, the antibody comprises HVR-H3 comprising the amino acid sequence of SEQ ID NO:57. In one embodiment, the antibody comprises HVR-H3 comprising the amino acid sequence of SEQ ID NO:63. In one embodiment, the antibody comprises HVR-H3 comprising the amino acid sequence of SEQ ID NO:69. In one embodiment, the antibody comprises HVR-H3 comprising the amino acid sequence of SEQ ID NO:75. In one embodiment, the antibody comprises HVR-H3 comprising the amino acid sequence of SEQ ID NO:81. In one embodiment, the antibody comprises HVR-H3 comprising the amino acid sequence of SEQ ID NO:87. In one embodiment, the antibody comprises HVR-H3 comprising the amino acid sequence of SEQ ID NO:93. In one embodiment, the antibody comprises HVR-H3 comprising the amino acid sequence of SEQ ID NO:99.

In another embodiment, the antibody comprises HVR-H3 comprising the amino acid sequence of SEQ ID NO:3 and HVR-L3 comprising the amino acid sequence of SEQ ID NO:6. In one embodiment, the antibody comprises HVR-H3 comprising the amino acid sequence of SEQ ID NO:9 and HVR-L3 comprising the amino acid sequence of SEQ ID NO:12. In one embodiment, the antibody comprises HVR-H3 comprising the amino acid sequence of SEQ ID NO:15 and HVR-L3 comprising the amino acid sequence of SEQ ID NO:18. In one embodiment, the antibody comprises HVR-H3 comprising the amino acid sequence of SEQ ID NO:21 and HVR-L3 comprising the amino acid sequence of SEQ ID NO:24. In one embodiment, the antibody comprises HVR-H3 comprising the amino acid sequence of SEQ ID NO:27 and HVR-L3 comprising the amino acid sequence of SEQ ID NO:30. In one embodiment, the antibody comprises HVR-H3 comprising the amino acid sequence of SEQ ID NO:33 and HVR-L3 comprising the amino acid sequence of SEQ ID NO:36. In one embodiment, the antibody comprises HVR-H3 comprising the amino acid sequence of SEQ ID NO:39 and HVR-L3 comprising the amino acid sequence of SEQ ID NO:42. In one embodiment, the antibody comprises HVR-H3 comprising the amino acid sequence of SEQ ID NO:45 and HVR-L3 comprising the amino acid sequence of SEQ ID NO:48. In one embodiment, the antibody comprises HVR-H3 comprising the amino acid sequence of SEQ ID NO:51 and HVR-L3 comprising the amino acid sequence of SEQ ID NO:54. In one embodiment, the antibody comprises HVR-H3 comprising the amino acid sequence of SEQ ID NO:57 and HVR-L3 comprising the amino acid sequence of SEQ ID NO:60. In one embodiment, the antibody comprises HVR-H3 comprising the amino acid sequence of SEQ ID NO:63 and HVR-L3 comprising the amino acid sequence of SEQ ID NO:66. In one embodiment, the antibody comprises HVR-H3 comprising the amino acid sequence of SEQ ID NO:69 and HVR-L3 comprising the amino acid sequence of SEQ ID NO:72. In one embodiment, the antibody comprises HVR-H3 comprising the amino acid sequence of SEQ ID NO:75 and HVR-L3 comprising the amino acid sequence of SEQ ID NO:78. In one embodiment, the antibody comprises HVR-H3 comprising the amino acid sequence of SEQ ID NO:81 and HVR-L3 comprising the amino acid sequence of SEQ ID NO:84. In one embodiment, the antibody comprises HVR-H3 comprising the amino acid sequence of SEQ ID NO:87 and HVR-L3 comprising the amino acid sequence of SEQ ID NO:90. In one embodiment, the antibody comprises HVR-H3 comprising the amino acid sequence of SEQ ID NO:93 and HVR-L3 comprising the amino acid sequence of SEQ ID NO:96. In one embodiment, the antibody comprises HVR-H3 comprising the amino acid sequence of SEQ ID NO:99 and HVR-L3 comprising the amino acid sequence of SEQ ID NO:102.

In a further embodiment, the antibody comprises HVR-H3 comprising the amino acid sequence of SEQ ID NO:3, HVR-L3 comprising the amino acid sequence of SEQ ID NO:6 and HVR-H2 comprising the amino acid sequence of SEQ ID NO:2. In one embodiment, the antibody comprises HVR-H3 comprising the amino acid sequence of SEQ ID NO:9, HVR-L3 comprising the amino acid sequence of SEQ ID NO:12 and HVR-H2 comprising the amino acid sequence of SEQ ID NO:8. In one embodiment, the antibody comprises HVR-H3 comprising the amino acid sequence of SEQ ID NO:15, HVR-L3 comprising the amino acid sequence of SEQ ID NO:18 and HVR-H2 comprising the amino acid sequence of SEQ ID NO:14. In one embodiment, the antibody comprises HVR-H3 comprising the amino acid sequence of SEQ ID NO:21, HVR-L3 comprising the amino acid sequence of SEQ ID NO:24 and HVR-H2 comprising the amino acid sequence of SEQ ID NO:20. In one embodiment, the antibody comprises HVR-H3 comprising the amino acid sequence of SEQ ID NO:27, HVR-L3 comprising the amino acid sequence of SEQ ID NO:30 and HVR-H2 comprising the amino acid sequence of SEQ ID NO:26. In one embodiment, the antibody comprises HVR-H3 comprising the amino acid sequence of SEQ ID NO:33, HVR-L3 comprising the amino acid sequence of SEQ ID NO:36 and HVR-H2 comprising the amino acid sequence of SEQ ID NO:32. In one embodiment, the antibody comprises HVR-H3 comprising the amino acid sequence of SEQ ID NO:39, HVR-L3 comprising the amino acid sequence of SEQ ID NO:42 and HVR-H2 comprising the amino acid sequence of SEQ ID NO:38. In one embodiment, the antibody comprises HVR-H3 comprising the amino acid sequence of SEQ ID NO:45, HVR-L3 comprising the amino acid sequence of SEQ ID NO:48 and HVR-H2 comprising the amino acid sequence of SEQ ID NO:44. In one embodiment, the antibody comprises HVR-H3 comprising the amino acid sequence of SEQ ID NO:51, HVR-L3 comprising the amino acid sequence of SEQ ID NO:54 and HVR-H2 comprising the amino acid sequence of SEQ ID NO:50. In one embodiment, the antibody comprises HVR-H3 comprising the amino acid sequence of SEQ ID NO:57, HVR-L3 comprising the amino acid sequence of SEQ ID NO:60 and HVR-H2 comprising the amino acid sequence of SEQ ID NO:56. In one embodiment, the antibody comprises HVR-H3 comprising the amino acid sequence of SEQ ID NO:63, HVR-L3 comprising the amino acid sequence of SEQ ID NO:66 and HVR-H2 comprising the amino acid sequence of SEQ ID NO:62. In one embodiment, the antibody comprises HVR-H3 comprising the amino acid sequence of SEQ ID NO:69, HVR-L3 comprising the amino acid sequence of SEQ ID NO:72 and HVR-H2 comprising the amino acid sequence of SEQ ID NO:68. In one embodiment, the antibody comprises HVR-H3 comprising the amino acid sequence of SEQ ID NO:75, HVR-L3 comprising the amino acid sequence of SEQ ID NO:78 and HVR-H2 comprising the amino acid sequence of SEQ ID NO:74. In one embodiment, the antibody comprises HVR-H3 comprising the amino acid sequence of SEQ ID NO:81, HVR-L3 comprising the amino acid sequence of SEQ ID NO:84 and HVR-H2 comprising the amino acid sequence of SEQ ID NO:80. In one embodiment, the antibody comprises HVR-H3 comprising the amino acid sequence of SEQ ID NO:87, HVR-L3 comprising the amino acid sequence of SEQ ID NO:90 and HVR-H2 comprising the amino acid sequence of SEQ ID NO:86. In one embodiment, the antibody comprises HVR-H3 comprising the amino acid sequence of SEQ ID NO:93, HVR-L3 comprising the amino acid sequence of SEQ ID NO:96 and HVR-H2 comprising the amino acid sequence of SEQ ID NO:92. In one embodiment, the antibody comprises HVR-H3 comprising the amino acid sequence of SEQ ID NO:99, HVR-L3 comprising the amino acid sequence of SEQ ID NO:102 and HVR-H2 comprising the amino acid sequence of SEQ ID NO:98.

In a further embodiment, the antibody comprises (a) HVR-H1 comprising the amino acid sequence of SEQ ID NO:1; (b) HVR-H2 comprising the amino acid sequence of SEQ ID NO:2; and (c) HVR-H3 comprising the amino acid sequence of SEQ ID NO:3. In a further embodiment, the antibody comprises (a) HVR-H1 comprising the amino acid sequence of SEQ ID NO:7; (b) HVR-H2 comprising the amino acid sequence of SEQ ID NO:8; and (c) HVR-H3 comprising the amino acid sequence of SEQ ID NO:9. In a further embodiment, the antibody comprises (a) HVR-H1 comprising the amino acid sequence of SEQ ID NO:13; (b) HVR-H2 comprising the amino acid sequence of SEQ ID NO:14; and (c) HVR-H3 comprising the amino acid sequence of SEQ ID NO:15. In a further embodiment, the antibody comprises (a) HVR-H1 comprising the amino acid sequence of SEQ ID NO:19; (b) HVR-H2 comprising the amino acid sequence of SEQ ID NO:20; and (c) HVR-H3 comprising the amino acid sequence of SEQ ID NO:21. In a further embodiment, the antibody comprises (a) HVR-H1 comprising the amino acid sequence of SEQ ID NO:25; (b) HVR-H2 comprising the amino acid sequence of SEQ ID NO:26; and (c) HVR-H3 comprising the amino acid sequence of SEQ ID NO:27. In a further embodiment, the antibody comprises (a) HVR-H1 comprising the amino acid sequence of SEQ ID NO:31; (b) HVR-H2 comprising the amino acid sequence of SEQ ID NO:32; and (c) HVR-H3 comprising the amino acid sequence of SEQ ID NO:33. In a further embodiment, the antibody comprises (a) HVR-H1 comprising the amino acid sequence of SEQ ID NO:37; (b) HVR-H2 comprising the amino acid sequence of SEQ ID NO:38; and (c) HVR-H3 comprising the amino acid sequence of SEQ ID NO:39. In a further embodiment, the antibody comprises (a) HVR-H1 comprising the amino acid sequence of SEQ ID NO:43; (b) HVR-H2 comprising the amino acid sequence of SEQ ID NO:44; and (c) HVR-H3 comprising the amino acid sequence of SEQ ID NO:45. In a further embodiment, the antibody comprises (a) HVR-H1 comprising the amino acid sequence of SEQ ID NO:49; (b) HVR-H2 comprising the amino acid sequence of SEQ ID NO:50; and (c) HVR-H3 comprising the amino acid sequence of SEQ ID NO:51. In a further embodiment, the antibody comprises (a) HVR-H1 comprising the amino acid sequence of SEQ ID NO:55; (b) HVR-H2 comprising the amino acid sequence of SEQ ID NO:56; and (c) HVR-H3 comprising the amino acid sequence of SEQ ID NO:57. In a further embodiment, the antibody comprises (a) HVR-H1 comprising the amino acid sequence of SEQ ID NO:61; (b) HVR-H2 comprising the amino acid sequence of SEQ ID NO:62; and (c) HVR-H3 comprising the amino acid sequence of SEQ ID NO:63. In a further embodiment, the antibody comprises (a) HVR-H1 comprising the amino acid sequence of SEQ ID NO:67; (b) HVR-H2 comprising the amino acid sequence of SEQ ID NO:68; and (c) HVR-H3 comprising the amino acid sequence of SEQ ID NO:69. In a further embodiment, the antibody comprises (a) HVR-H1 comprising the amino acid sequence of SEQ ID NO:73; (b) HVR-H2 comprising the amino acid sequence of SEQ ID NO:74; and (c) HVR-H3 comprising the amino acid sequence of SEQ ID NO:75. In a further embodiment, the antibody comprises (a) HVR-H1 comprising the amino acid sequence of SEQ ID NO:79; (b) HVR-H2 comprising the amino acid sequence of SEQ ID NO:80; and (c) HVR-H3 comprising the amino acid sequence of SEQ ID NO:81. In a further embodiment, the antibody comprises (a) HVR-H1 comprising the amino acid sequence of SEQ ID NO:85; (b) HVR-H2 comprising the amino acid sequence of SEQ ID NO:86; and (c) HVR-H3 comprising the amino acid sequence of SEQ ID NO:87. In a further embodiment, the antibody comprises (a) HVR-H1 comprising the amino acid sequence of SEQ ID NO:91; (b) HVR-H2 comprising the amino acid sequence of SEQ ID NO:92; and (c) HVR-H3 comprising the amino acid sequence of SEQ ID NO:93. In a further embodiment, the antibody comprises (a) HVR-H1 comprising the amino acid sequence of SEQ ID NO:97; (b) HVR-H2 comprising the amino acid sequence of SEQ ID NO:98; and (c) HVR-H3 comprising the amino acid sequence of SEQ ID NO:99.

In another aspect, the invention provides an antibody comprising at least one, at least two, or all three VL HVR sequences selected from (a) HVR-L1 comprising the amino acid sequence of SEQ ID NO:4; (b) HVR-L2 comprising the amino acid sequence of SEQ ID NO:5; and (c) HVR-L3 comprising the amino acid sequence of SEQ ID NO:6.

In another aspect, the invention provides an antibody comprising at least one, at least two, or all three VL HVR sequences selected from (a) HVR-L1 comprising the amino acid sequence of SEQ ID NO:10; (b) HVR-L2 comprising the amino acid sequence of SEQ ID NO:11; and (c) HVR-L3 comprising the amino acid sequence of SEQ ID NO:12.

In another aspect, the invention provides an antibody comprising at least one, at least two, or all three VL HVR sequences selected from (a) HVR-L1 comprising the amino acid sequence of SEQ ID NO:16; (b) HVR-L2 comprising the amino acid sequence of SEQ ID NO:17; and (c) HVR-L3 comprising the amino acid sequence of SEQ ID NO:18.

In another aspect, the invention provides an antibody comprising at least one, at least two, or all three VL HVR sequences selected from (a) HVR-L1 comprising the amino acid sequence of SEQ ID NO:22; (b) HVR-L2 comprising the amino acid sequence of SEQ ID NO:23; and (c) HVR-L3 comprising the amino acid sequence of SEQ ID NO:24.

In another aspect, the invention provides an antibody comprising at least one, at least two, or all three VL HVR sequences selected from (a) HVR-L1 comprising the amino acid sequence of SEQ ID NO:28; (b) HVR-L2 comprising the amino acid sequence of SEQ ID NO:29; and (c) HVR-L3 comprising the amino acid sequence of SEQ ID NO:30.

In another aspect, the invention provides an antibody comprising at least one, at least two, or all three VL HVR sequences selected from (a) HVR-L1 comprising the amino acid sequence of SEQ ID NO:34; (b) HVR-L2 comprising the amino acid sequence of SEQ ID NO:35; and (c) HVR-L3 comprising the amino acid sequence of SEQ ID NO:36.

In another aspect, the invention provides an antibody comprising at least one, at least two, or all three VL HVR sequences selected from (a) HVR-L1 comprising the amino acid sequence of SEQ ID NO:40; (b) HVR-L2 comprising the amino acid sequence of SEQ ID NO:41; and (c) HVR-L3 comprising the amino acid sequence of SEQ ID NO:42.

In another aspect, the invention provides an antibody comprising at least one, at least two, or all three VL HVR sequences selected from (a) HVR-L1 comprising the amino acid sequence of SEQ ID NO:46; (b) HVR-L2 comprising the amino acid sequence of SEQ ID NO:47; and (c) HVR-L3 comprising the amino acid sequence of SEQ ID NO:48.

In another aspect, the invention provides an antibody comprising at least one, at least two, or all three VL HVR sequences selected from (a) HVR-L1 comprising the amino acid sequence of SEQ ID NO:52; (b) HVR-L2 comprising the amino acid sequence of SEQ ID NO:53; and (c) HVR-L3 comprising the amino acid sequence of SEQ ID NO:54.

In another aspect, the invention provides an antibody comprising at least one, at least two, or all three VL HVR sequences selected from (a) HVR-L1 comprising the amino acid sequence of SEQ ID NO:58; (b) HVR-L2 comprising the amino acid sequence of SEQ ID NO:59; and (c) HVR-L3 comprising the amino acid sequence of SEQ ID NO:60.

In another aspect, the invention provides an antibody comprising at least one, at least two, or all three VL HVR sequences selected from (a) HVR-L1 comprising the amino acid sequence of SEQ ID NO:64; (b) HVR-L2 comprising the amino acid sequence of SEQ ID NO:65; and (c) HVR-L3 comprising the amino acid sequence of SEQ ID NO:66.

In another aspect, the invention provides an antibody comprising at least one, at least two, or all three VL HVR sequences selected from (a) HVR-L1 comprising the amino acid sequence of SEQ ID NO:70; (b) HVR-L2 comprising the amino acid sequence of SEQ ID NO:71; and (c) HVR-L3 comprising the amino acid sequence of SEQ ID NO:72.

In another aspect, the invention provides an antibody comprising at least one, at least two, or all three VL HVR sequences selected from (a) HVR-L1 comprising the amino acid sequence of SEQ ID NO:76; (b) HVR-L2 comprising the amino acid sequence of SEQ ID NO:77; and (c) HVR-L3 comprising the amino acid sequence of SEQ ID NO:78.

In another aspect, the invention provides an antibody comprising at least one, at least two, or all three VL HVR sequences selected from (a) HVR-L1 comprising the amino acid sequence of SEQ ID NO:82; (b) HVR-L2 comprising the amino acid sequence of SEQ ID NO:83; and (c) HVR-L3 comprising the amino acid sequence of SEQ ID NO:84.

In another aspect, the invention provides an antibody comprising at least one, at least two, or all three VL HVR sequences selected from (a) HVR-L1 comprising the amino acid sequence of SEQ ID NO:88; (b) HVR-L2 comprising the amino acid sequence of SEQ ID NO:89; and (c) HVR-L3 comprising the amino acid sequence of SEQ ID NO:90.

In another aspect, the invention provides an antibody comprising at least one, at least two, or all three VL HVR sequences selected from (a) HVR-L1 comprising the amino acid sequence of SEQ ID NO:94; (b) HVR-L2 comprising the amino acid sequence of SEQ ID NO:95; and (c) HVR-L3 comprising the amino acid sequence of SEQ ID NO:96.

In another aspect, the invention provides an antibody comprising at least one, at least two, or all three VL HVR sequences selected from (a) HVR-L1 comprising the amino acid sequence of SEQ ID NO:100; (b) HVR-L2 comprising the amino acid sequence of SEQ ID NO:101; and (c) HVR-L3 comprising the amino acid sequence of SEQ ID NO:102.

In one embodiment, the antibody comprises (a) HVR-L1 comprising the amino acid sequence of SEQ ID NO:4; (b) HVR-L2 comprising the amino acid sequence of SEQ ID NO:5; and (c) HVR-L3 comprising the amino acid sequence of SEQ ID NO:6. In one embodiment, the antibody comprises (a) HVR-L1 comprising the amino acid sequence of SEQ ID NO:10; (b) HVR-L2 comprising the amino acid sequence of SEQ ID NO:11; and (c) HVR-L3 comprising the amino acid sequence of SEQ ID NO:12. In one embodiment, the antibody comprises (a) HVR-L1 comprising the amino acid sequence of SEQ ID NO:16; (b) HVR-L2 comprising the amino acid sequence of SEQ ID NO:17; and (c) HVR-L3 comprising the amino acid sequence of SEQ ID NO:18. In one embodiment, the antibody comprises (a) HVR-L1 comprising the amino acid sequence of SEQ ID NO:22; (b) HVR-L2 comprising the amino acid sequence of SEQ ID NO:23; and (c) HVR-L3 comprising the amino acid sequence of SEQ ID NO:24. In one embodiment, the antibody comprises (a) HVR-L1 comprising the amino acid sequence of SEQ ID NO:28; (b) HVR-L2 comprising the amino acid sequence of SEQ ID NO:29; and (c) HVR-L3 comprising the amino acid sequence of SEQ ID NO:30. In one embodiment, the antibody comprises (a) HVR-L1 comprising the amino acid sequence of SEQ ID NO:34; (b) HVR-L2 comprising the amino acid sequence of SEQ ID NO:35; and (c) HVR-L3 comprising the amino acid sequence of SEQ ID NO:36. In one embodiment, the antibody comprises (a) HVR-L1 comprising the amino acid sequence of SEQ ID NO:40; (b) HVR-L2 comprising the amino acid sequence of SEQ ID NO:41; and (c) HVR-L3 comprising the amino acid sequence of SEQ ID NO:42. In one embodiment, the antibody comprises (a) HVR-L1 comprising the amino acid sequence of SEQ ID NO:46; (b) HVR-L2 comprising the amino acid sequence of SEQ ID NO:47; and (c) HVR-L3 comprising the amino acid sequence of SEQ ID NO:48. In one embodiment, the antibody comprises (a) HVR-L1 comprising the amino acid sequence of SEQ ID NO:52; (b) HVR-L2 comprising the amino acid sequence of SEQ ID NO:53; and (c) HVR-L3 comprising the amino acid sequence of SEQ ID NO:54. In one embodiment, the antibody comprises (a) HVR-L1 comprising the amino acid sequence of SEQ ID NO:58; (b) HVR-L2 comprising the amino acid sequence of SEQ ID NO:59; and (c) HVR-L3 comprising the amino acid sequence of SEQ ID NO:60. In one embodiment, the antibody comprises (a) HVR-L1 comprising the amino acid sequence of SEQ ID NO:64; (b) HVR-L2 comprising the amino acid sequence of SEQ ID NO:65; and (c) HVR-L3 comprising the amino acid sequence of SEQ ID NO:66. In one embodiment, the antibody comprises (a) HVR-L1 comprising the amino acid sequence of SEQ ID NO:70; (b) HVR-L2 comprising the amino acid sequence of SEQ ID NO:71; and (c) HVR-L3 comprising the amino acid sequence of SEQ ID NO:72. In one embodiment, the antibody comprises (a) HVR-L1 comprising the amino acid sequence of SEQ ID NO:76; (b) HVR-L2 comprising the amino acid sequence of SEQ ID NO:77; and (c) HVR-L3 comprising the amino acid sequence of SEQ ID NO:78. In one embodiment, the antibody comprises (a) HVR-L1 comprising the amino acid sequence of SEQ ID NO:82; (b) HVR-L2 comprising the amino acid sequence of SEQ ID NO:83; and (c) HVR-L3 comprising the amino acid sequence of SEQ ID NO:84. In one embodiment, the antibody comprises (a) HVR-L1 comprising the amino acid sequence of SEQ ID NO:88; (b) HVR-L2 comprising the amino acid sequence of SEQ ID NO:89; and (c) HVR-L3 comprising the amino acid sequence of SEQ ID NO:90. In one embodiment, the antibody comprises (a) HVR-L1 comprising the amino acid sequence of SEQ ID NO:94; (b) HVR-L2 comprising the amino acid sequence of SEQ ID NO:95; and (c) HVR-L3 comprising the amino acid sequence of SEQ ID NO:96. In one embodiment, the antibody comprises (a) HVR-L1 comprising the amino acid sequence of SEQ ID NO:100; (b) HVR-L2 comprising the amino acid sequence of SEQ ID NO:101; and (c) HVR-L3 comprising the amino acid sequence of SEQ ID NO:102.

In another aspect, an antibody of the invention comprises (a) a VH domain comprising at least one, at least two, or all three VH HVR sequences selected from (i) HVR-H1 comprising the amino acid sequence of SEQ ID NO:1, (ii) HVR-H2 comprising the amino acid sequence of SEQ ID NO:2, and (iii) HVR-H3 comprising an amino acid sequence selected from SEQ ID NO:3; and (b) a VL domain comprising at least one, at least two, or all three VL HVR sequences selected from (i) HVR-L1 comprising the amino acid sequence of SEQ ID NO:4, (ii) HVR-L2 comprising the amino acid sequence of SEQ ID NO:5, and (c) HVR-L3 comprising the amino acid sequence of SEQ ID NO:6.

In another aspect, an antibody of the invention comprises (a) a VH domain comprising at least one, at least two, or all three VH HVR sequences selected from (i) HVR-H1 comprising the amino acid sequence of SEQ ID NO:7, (ii) HVR-H2 comprising the amino acid sequence of SEQ ID NO:8, and (iii) HVR-H3 comprising an amino acid sequence selected from SEQ ID NO:9; and (b) a VL domain comprising at least one, at least two, or all three VL HVR sequences selected from (i) HVR-L1 comprising the amino acid sequence of SEQ ID NO:10, (ii) HVR-L2 comprising the amino acid sequence of SEQ ID NO:11, and (c) HVR-L3 comprising the amino acid sequence of SEQ ID NO:12.

In another aspect, an antibody of the invention comprises (a) a VH domain comprising at least one, at least two, or all three VH HVR sequences selected from (i) HVR-H1 comprising the amino acid sequence of SEQ ID NO:13, (ii) HVR-H2 comprising the amino acid sequence of SEQ ID NO:14, and (iii) HVR-H3 comprising an amino acid sequence selected from SEQ ID NO:15; and (b) a VL domain comprising at least one, at least two, or all three VL HVR sequences selected from (i) HVR-L1 comprising the amino acid sequence of SEQ ID NO:16, (ii) HVR-L2 comprising the amino acid sequence of SEQ ID NO:17, and (c) HVR-L3 comprising the amino acid sequence of SEQ ID NO:18.

In another aspect, an antibody of the invention comprises (a) a VH domain comprising at least one, at least two, or all three VH HVR sequences selected from (i) HVR-H1 comprising the amino acid sequence of SEQ ID NO:19, (ii) HVR-H2 comprising the amino acid sequence of SEQ ID NO:20, and (iii) HVR-H3 comprising an amino acid sequence selected from SEQ ID NO:21; and (b) a VL domain comprising at least one, at least two, or all three VL HVR sequences selected from (i) HVR-L1 comprising the amino acid sequence of SEQ ID NO:22, (ii) HVR-L2 comprising the amino acid sequence of SEQ ID NO:23, and (c) HVR-L3 comprising the amino acid sequence of SEQ ID NO:24.

In another aspect, an antibody of the invention comprises (a) a VH domain comprising at least one, at least two, or all three VH HVR sequences selected from (i) HVR-H1 comprising the amino acid sequence of SEQ ID NO:25, (ii) HVR-H2 comprising the amino acid sequence of SEQ ID NO:26, and (iii) HVR-H3 comprising an amino acid sequence selected from SEQ ID NO:27; and (b) a VL domain comprising at least one, at least two, or all three VL HVR sequences selected from (i) HVR-L1 comprising the amino acid sequence of SEQ ID NO:28, (ii) HVR-L2 comprising the amino acid sequence of SEQ ID NO:29, and (c) HVR-L3 comprising the amino acid sequence of SEQ ID NO:30.

In another aspect, an antibody of the invention comprises (a) a VH domain comprising at least one, at least two, or all three VH HVR sequences selected from (i) HVR-H1 comprising the amino acid sequence of SEQ ID NO:31, (ii) HVR-H2 comprising the amino acid sequence of SEQ ID NO:32, and (iii) HVR-H3 comprising an amino acid sequence selected from SEQ ID NO:33; and (b) a VL domain comprising at least one, at least two, or all three VL HVR sequences selected from (i) HVR-L1 comprising the amino acid sequence of SEQ ID NO:34, (ii) HVR-L2 comprising the amino acid sequence of SEQ ID NO:35, and (c) HVR-L3 comprising the amino acid sequence of SEQ ID NO:36.

In another aspect, an antibody of the invention comprises (a) a VH domain comprising at least one, at least two, or all three VH HVR sequences selected from (i) HVR-H1 comprising the amino acid sequence of SEQ ID NO:37, (ii) HVR-H2 comprising the amino acid sequence of SEQ ID NO:38, and (iii) HVR-H3 comprising an amino acid sequence selected from SEQ ID NO:39; and (b) a VL domain comprising at least one, at least two, or all three VL HVR sequences selected from (i) HVR-L1 comprising the amino acid sequence of SEQ ID NO:40, (ii) HVR-L2 comprising the amino acid sequence of SEQ ID NO:41, and (c) HVR-L3 comprising the amino acid sequence of SEQ ID NO:42.

In another aspect, an antibody of the invention comprises (a) a VH domain comprising at least one, at least two, or all three VH HVR sequences selected from (i) HVR-H1 comprising the amino acid sequence of SEQ ID NO:43, (ii) HVR-H2 comprising the amino acid sequence of SEQ ID NO:44, and (iii) HVR-H3 comprising an amino acid sequence selected from SEQ ID NO:45; and (b) a VL domain comprising at least one, at least two, or all three VL HVR sequences selected from (i) HVR-L1 comprising the amino acid sequence of SEQ ID NO:46, (ii) HVR-L2 comprising the amino acid sequence of SEQ ID NO:47, and (c) HVR-L3 comprising the amino acid sequence of SEQ ID NO:48.

In another aspect, an antibody of the invention comprises (a) a VH domain comprising at least one, at least two, or all three VH HVR sequences selected from (i) HVR-H1 comprising the amino acid sequence of SEQ ID NO:49, (ii) HVR-H2 comprising the amino acid sequence of SEQ ID NO:50, and (iii) HVR-H3 comprising an amino acid sequence selected from SEQ ID NO:51; and (b) a VL domain comprising at least one, at least two, or all three VL HVR sequences selected from (i) HVR-L1 comprising the amino acid sequence of SEQ ID NO:52, (ii) HVR-L2 comprising the amino acid sequence of SEQ ID NO:53, and (c) HVR-L3 comprising the amino acid sequence of SEQ ID NO:54.

In another aspect, an antibody of the invention comprises (a) a VH domain comprising at least one, at least two, or all three VH HVR sequences selected from (i) HVR-H1 comprising the amino acid sequence of SEQ ID NO:55, (ii) HVR-H2 comprising the amino acid sequence of SEQ ID NO:56, and (iii) HVR-H3 comprising an amino acid sequence selected from SEQ ID NO:57; and (b) a VL domain comprising at least one, at least two, or all three VL HVR sequences selected from (i) HVR-L1 comprising the amino acid sequence of SEQ ID NO:58, (ii) HVR-L2 comprising the amino acid sequence of SEQ ID NO:59, and (c) HVR-L3 comprising the amino acid sequence of SEQ ID NO:60.

In another aspect, an antibody of the invention comprises (a) a VH domain comprising at least one, at least two, or all three VH HVR sequences selected from (i) HVR-H1 comprising the amino acid sequence of SEQ ID NO:61, (ii) HVR-H2 comprising the amino acid sequence of SEQ ID NO:62, and (iii) HVR-H3 comprising an amino acid sequence selected from SEQ ID NO:63; and (b) a VL domain comprising at least one, at least two, or all three VL HVR sequences selected from (i) HVR-L1 comprising the amino acid sequence of SEQ ID NO:64, (ii) HVR-L2 comprising the amino acid sequence of SEQ ID NO:65, and (c) HVR-L3 comprising the amino acid sequence of SEQ ID NO:66.

In another aspect, an antibody of the invention comprises (a) a VH domain comprising at least one, at least two, or all three VH HVR sequences selected from (i) HVR-H1 comprising the amino acid sequence of SEQ ID NO:67, (ii) HVR-H2 comprising the amino acid sequence of SEQ ID NO:68, and (iii) HVR-H3 comprising an amino acid sequence selected from SEQ ID NO:69; and (b) a VL domain comprising at least one, at least two, or all three VL HVR sequences selected from (i) HVR-L1 comprising the amino acid sequence of SEQ ID NO:70, (ii) HVR-L2 comprising the amino acid sequence of SEQ ID NO:71, and (c) HVR-L3 comprising the amino acid sequence of SEQ ID NO:72.

In another aspect, an antibody of the invention comprises (a) a VH domain comprising at least one, at least two, or all three VH HVR sequences selected from (i) HVR-H1 comprising the amino acid sequence of SEQ ID NO:73, (ii) HVR-H2 comprising the amino acid sequence of SEQ ID NO:74, and (iii) HVR-H3 comprising an amino acid sequence selected from SEQ ID NO:75; and (b) a VL domain comprising at least one, at least two, or all three VL HVR sequences selected from (i) HVR-L1 comprising the amino acid sequence of SEQ ID NO:76, (ii) HVR-L2 comprising the amino acid sequence of SEQ ID NO:77, and (c) HVR-L3 comprising the amino acid sequence of SEQ ID NO:78.

In another aspect, an antibody of the invention comprises (a) a VH domain comprising at least one, at least two, or all three VH HVR sequences selected from (i) HVR-H1 comprising the amino acid sequence of SEQ ID NO:79, (ii) HVR-H2 comprising the amino acid sequence of SEQ ID NO:80, and (iii) HVR-H3 comprising an amino acid sequence selected from SEQ ID NO:81; and (b) a VL domain comprising at least one, at least two, or all three VL HVR sequences selected from (i) HVR-L1 comprising the amino acid sequence of SEQ ID NO:82, (ii) HVR-L2 comprising the amino acid sequence of SEQ ID NO:83, and (c) HVR-L3 comprising the amino acid sequence of SEQ ID NO:84.

In another aspect, an antibody of the invention comprises (a) a VH domain comprising at least one, at least two, or all three VH HVR sequences selected from (i) HVR-H1 comprising the amino acid sequence of SEQ ID NO:85, (ii) HVR-H2 comprising the amino acid sequence of SEQ ID NO:86, and (iii) HVR-H3 comprising an amino acid sequence selected from SEQ ID NO:87; and (b) a VL domain comprising at least one, at least two, or all three VL HVR sequences selected from (i) HVR-L1 comprising the amino acid sequence of SEQ ID NO:88, (ii) HVR-L2 comprising the amino acid sequence of SEQ ID NO:89, and (c) HVR-L3 comprising the amino acid sequence of SEQ ID NO:90.

In another aspect, an antibody of the invention comprises (a) a VH domain comprising at least one, at least two, or all three VH HVR sequences selected from (i) HVR-H1 comprising the amino acid sequence of SEQ ID NO:91, (ii) HVR-H2 comprising the amino acid sequence of SEQ ID NO:92, and (iii) HVR-H3 comprising an amino acid sequence selected from SEQ ID NO:93; and (b) a VL domain comprising at least one, at least two, or all three VL HVR sequences selected from (i) HVR-L1 comprising the amino acid sequence of SEQ ID NO:94, (ii) HVR-L2 comprising the amino acid sequence of SEQ ID NO:95, and (c) HVR-L3 comprising the amino acid sequence of SEQ ID NO:96.

In another aspect, an antibody of the invention comprises (a) a VH domain comprising at least one, at least two, or all three VH HVR sequences selected from (i) HVR-H1 comprising the amino acid sequence of SEQ ID NO:97, (ii) HVR-H2 comprising the amino acid sequence of SEQ ID NO:98, and (iii) HVR-H3 comprising an amino acid sequence selected from SEQ ID NO:99; and (b) a VL domain comprising at least one, at least two, or all three VL HVR sequences selected from (i) HVR-L1 comprising the amino acid sequence of SEQ ID NO:100, (ii) HVR-L2 comprising the amino acid sequence of SEQ ID NO:101, and (c) HVR-L3 comprising the amino acid sequence of SEQ ID NO:102.

In another aspect, the invention provides an antibody comprising (a) HVR-H1 comprising the amino acid sequence of SEQ ID NO:1; (b) HVR-H2 comprising the amino acid sequence of SEQ ID NO:2; (c) HVR-H3 comprising the amino acid sequence of SEQ ID NO:3; (d) HVR-L1 comprising the amino acid sequence of SEQ ID NO:4; (e) HVR-L2 comprising the amino acid sequence of SEQ ID NO:5; and (f) HVR-L3 comprising the amino acid sequence of SEQ ID NO:6.

In another aspect, the invention provides an antibody comprising (a) HVR-H1 comprising the amino acid sequence of SEQ ID NO:7; (b) HVR-H2 comprising the amino acid sequence of SEQ ID NO:8; (c) HVR-H3 comprising the amino acid sequence of SEQ ID NO:9; (d) HVR-L1 comprising the amino acid sequence of SEQ ID NO:10; (e) HVR-L2 comprising the amino acid sequence of SEQ ID NO:11; and (f) HVR-L3 comprising the amino acid sequence of SEQ ID NO:12.

In another aspect, the invention provides an antibody comprising (a) HVR-H1 comprising the amino acid sequence of SEQ ID NO:13; (b) HVR-H2 comprising the amino acid sequence of SEQ ID NO:14; (c) HVR-H3 comprising the amino acid sequence of SEQ ID NO:15; (d) HVR-L1 comprising the amino acid sequence of SEQ ID NO:16; (e) HVR-L2 comprising the amino acid sequence of SEQ ID NO:17; and (f) HVR-L3 comprising the amino acid sequence of SEQ ID NO:18.

In another aspect, the invention provides an antibody comprising (a) HVR-H1 comprising the amino acid sequence of SEQ ID NO:19; (b) HVR-H2 comprising the amino acid sequence of SEQ ID NO:20; (c) HVR-H3 comprising the amino acid sequence of SEQ ID NO:21; (d) HVR-L1 comprising the amino acid sequence of SEQ ID NO:22; (e) HVR-L2 comprising the amino acid sequence of SEQ ID NO:23; and (f) HVR-L3 comprising the amino acid sequence of SEQ ID NO:24.

In another aspect, the invention provides an antibody comprising (a) HVR-H1 comprising the amino acid sequence of SEQ ID NO:25; (b) HVR-H2 comprising the amino acid sequence of SEQ ID NO:26; (c) HVR-H3 comprising the amino acid sequence of SEQ ID NO:27; (d) HVR-L1 comprising the amino acid sequence of SEQ ID NO:28; (e) HVR-L2 comprising the amino acid sequence of SEQ ID NO:29; and (f) HVR-L3 comprising the amino acid sequence of SEQ ID NO:30.

In another aspect, the invention provides an antibody comprising (a) HVR-H1 comprising the amino acid sequence of SEQ ID NO:31; (b) HVR-H2 comprising the amino acid sequence of SEQ ID NO:32; (c) HVR-H3 comprising the amino acid sequence of SEQ ID NO:33; (d) HVR-L1 comprising the amino acid sequence of SEQ ID NO:34; (e) HVR-L2 comprising the amino acid sequence of SEQ ID NO:35; and (f) HVR-L3 comprising the amino acid sequence of SEQ ID NO:36.

In another aspect, the invention provides an antibody comprising (a) HVR-H1 comprising the amino acid sequence of SEQ ID NO:37; (b) HVR-H2 comprising the amino acid sequence of SEQ ID NO:38; (c) HVR-H3 comprising the amino acid sequence of SEQ ID NO:39; (d) HVR-L1 comprising the amino acid sequence of SEQ ID NO:40; (e) HVR-L2 comprising the amino acid sequence of SEQ ID NO:41; and (f) HVR-L3 comprising the amino acid sequence of SEQ ID NO:42.

In another aspect, the invention provides an antibody comprising (a) HVR-H1 comprising the amino acid sequence of SEQ ID NO:43; (b) HVR-H2 comprising the amino acid sequence of SEQ ID NO:44; (c) HVR-H3 comprising the amino acid sequence of SEQ ID NO:45; (d) HVR-L1 comprising the amino acid sequence of SEQ ID NO:46; (e) HVR-L2 comprising the amino acid sequence of SEQ ID NO:47; and (f) HVR-L3 comprising the amino acid sequence of SEQ ID NO:48.

In another aspect, the invention provides an antibody comprising (a) HVR-H1 comprising the amino acid sequence of SEQ ID NO:49; (b) HVR-H2 comprising the amino acid sequence of SEQ ID NO:50; (c) HVR-H3 comprising the amino acid sequence of SEQ ID NO:51; (d) HVR-L1 comprising the amino acid sequence of SEQ ID NO:52; (e) HVR-L2 comprising the amino acid sequence of SEQ ID NO:53; and (f) HVR-L3 comprising the amino acid sequence of SEQ ID NO:54.

In another aspect, the invention provides an antibody comprising (a) HVR-H1 comprising the amino acid sequence of SEQ ID NO:55; (b) HVR-H2 comprising the amino acid sequence of SEQ ID NO:56; (c) HVR-H3 comprising the amino acid sequence of SEQ ID NO:57; (d) HVR-L1 comprising the amino acid sequence of SEQ ID NO:58; (e) HVR-L2 comprising the amino acid sequence of SEQ ID NO:59; and (f) HVR-L3 comprising the amino acid sequence of SEQ ID NO:60.

In another aspect, the invention provides an antibody comprising (a) HVR-H1 comprising the amino acid sequence of SEQ ID NO:61; (b) HVR-H2 comprising the amino acid sequence of SEQ ID NO:62; (c) HVR-H3 comprising the amino acid sequence of SEQ ID NO:63; (d) HVR-L1 comprising the amino acid sequence of SEQ ID NO:64; (e) HVR-L2 comprising the amino acid sequence of SEQ ID NO:65; and (f) HVR-L3 comprising the amino acid sequence of SEQ ID NO:66.

In another aspect, the invention provides an antibody comprising (a) HVR-H1 comprising the amino acid sequence of SEQ ID NO:67; (b) HVR-H2 comprising the amino acid sequence of SEQ ID NO:68; (c) HVR-H3 comprising the amino acid sequence of SEQ ID NO:69; (d) HVR-L1 comprising the amino acid sequence of SEQ ID NO:70; (e) HVR-L2 comprising the amino acid sequence of SEQ ID NO:71; and (f) HVR-L3 comprising the amino acid sequence of SEQ ID NO:72.

In another aspect, the invention provides an antibody comprising (a) HVR-H1 comprising the amino acid sequence of SEQ ID NO:73; (b) HVR-H2 comprising the amino acid sequence of SEQ ID NO:74; (c) HVR-H3 comprising the amino acid sequence of SEQ ID NO:75; (d) HVR-L1 comprising the amino acid sequence of SEQ ID NO:76; (e) HVR-L2 comprising the amino acid sequence of SEQ ID NO:77; and (f) HVR-L3 comprising the amino acid sequence of SEQ ID NO:78.

In another aspect, the invention provides an antibody comprising (a) HVR-H1 comprising the amino acid sequence of SEQ ID NO:79; (b) HVR-H2 comprising the amino acid sequence of SEQ ID NO:80; (c) HVR-H3 comprising the amino acid sequence of SEQ ID NO:81; (d) HVR-L1 comprising the amino acid sequence of SEQ ID NO:82; (e) HVR-L2 comprising the amino acid sequence of SEQ ID NO:83; and (f) HVR-L3 comprising the amino acid sequence of SEQ ID NO:84.

In another aspect, the invention provides an antibody comprising (a) HVR-H1 comprising the amino acid sequence of SEQ ID NO:85; (b) HVR-H2 comprising the amino acid sequence of SEQ ID NO:86; (c) HVR-H3 comprising the amino acid sequence of SEQ ID NO:87; (d) HVR-L1 comprising the amino acid sequence of SEQ ID NO:88; (e) HVR-L2 comprising the amino acid sequence of SEQ ID NO:89; and (f) HVR-L3 comprising the amino acid sequence of SEQ ID NO:90.

In another aspect, the invention provides an antibody comprising (a) HVR-H1 comprising the amino acid sequence of SEQ ID NO:91; (b) HVR-H2 comprising the amino acid sequence of SEQ ID NO:92; (c) HVR-H3 comprising the amino acid sequence of SEQ ID NO:93; (d) HVR-L1 comprising the amino acid sequence of SEQ ID NO:94; (e) HVR-L2 comprising the amino acid sequence of SEQ ID NO:95; and (f) HVR-L3 comprising the amino acid sequence of SEQ ID NO:96.

In another aspect, the invention provides an antibody comprising (a) HVR-H1 comprising the amino acid sequence of SEQ ID NO:97; (b) HVR-H2 comprising the amino acid sequence of SEQ ID NO:98; (c) HVR-H3 comprising the amino acid sequence of SEQ ID NO:99; (d) HVR-L1 comprising the amino acid sequence of SEQ ID NO:100; (e) HVR-L2 comprising the amino acid sequence of SEQ ID NO:101; and (f) HVR-L3 comprising the amino acid sequence of SEQ ID NO:102.

In certain embodiments, any one or more amino acids of an anti-Axl antibody as provided above are substituted or absent at the following HVR positions:

in HVR-H1 (SEQ ID NO:7): positions 2, 3, 4, 5, 6, 7, 8, 9, and 10;

in HVR-H2 (SEQ ID NO:8): positions 1, 2, 4, 6, 7, 8, 9, and 10;

in HVR-H3 (SEQ ID NO:9): positions 3, 4, 5, 6, 7, 8, 9, 10, 11, 12, 13, 14, or 15;

in HVR-L1 (SEQ ID NO:10): positions 5, 6, 7, 8, 9, and 10;

in HVR-L2 (SEQ ID NO:11): positions 1, 4, and 6;

in HVR-L3 (SEQ ID NO:12): positions 3, 4, 5, 6, 7, and 8.

In certain embodiments, the substitutions are conservative substitutions, as provided herein. In certain embodiments, any one or more of the following substitutions may be made in any combination:

in HVR-H1 (SEQ ID NO:7): S28T; L29F or V: S30T or R; G31S; S32H, T or I; W33G; I34L;

in HVR-H2 (SEQ ID NO:8): G49A; W50G; N52S, A, or P; Y53A or V; R54G or S; G55S or R; Y56S or H; A57T or P;

in HVR-H3 (SEQ ID NO:9): E95W; Y96R; S97N or P; G98D or L; W99S; G100R, A, or S; G100aS; S100b absent; S100cY or absent; V100dI or absent; G100e or absent; Y100f or absent, A100gE or absent;

in HVR-L1 (SEQ ID NO:10): D28I or S; V29I; S30G or R; T31I, N or R; A32S; V33L;

in HVR-L2 (SEQ ID NO:11): S50A or V; F53N or S; Y55A;

in HVR-L3 (SEQ ID NO:12): S91A; Y92K or N; T93S, Y, M, R, or A; T94N, F, or S; P95R; P96Y, S, or L.

In certain embodiments, any one or more of the following substitutions may be made in any combination:

in HVR-H1 (SEQ ID NO:7): S28T; L29F or V: S30T; G31S; S32H, T or I;

in HVR-H2 (SEQ ID NO:8): N52S, or A; R54G or S; G55R; Y56S, or H; A57T or P;

in HVR-H3 (SEQ ID NO:9): S97N or P; G98D; G100 S;

in HVR-L3 (SEQ ID NO:12): T93S, or Y; T94N, F, or S.

All possible combinations of the above substitutions are encompassed by the consensus sequences:

HVR-H1 (SEQ ID NO:112): $GFX_1X_2X_3X_4X_5X_6X_7H$, wherein $X_1$ is S or T; $X_2$ is L, F or V; $X_3$ is S, T, or R; $X_4$ is G or S; $X_5$ is S, H, T or I; $X_6$ is W or G; $X_7$ is I or L;

in HVR-H2 (SEQ ID NO:113): $X_1X_2IX_3PX_4X_5X_6X_7X_8YYADSVKG$, wherein $X_1$ is G or A; $X_2$ is W or G; $X_3$ is N, S, A or P; $X_4$ is Y, A or V; $X_5$ is R, G, or S; $X_6$ is G R or S; $X_7$ is Y, S, H or Y; $X_8$ is A, T, or P; and/or (SEQ ID NO:166): $X_1X_2IX_3PX_4X_5X_6X_7X_8X_9X_{10}YYADSVKG$, wherein $X_1$ is G or A; $X_2$ is W or G; $X_3$ is N, S, A or P; $X_4$ is Y, A or V; $X_5$ is R, G, or S; $X_6$ is G R or S; $X_7$ is Y, S, H or Y; $X_8$ is A, T, or P; $X_9$ is any amino acid or absent; $X_{10}$ is any amino acid or absent;

in HVR-H3 (SEQ ID NO:114): $ARX_1X_2X_3X_4X_5X_6X_7X_8X_9X_{10}X_{11}X_{12}X_{13}MDY$, wherein $X_1$ is E or W; $X_2$ is Y or R; $X_3$ is S, N or P; $X_4$ is G, D, or L; $X_5$ is W or S; $X_6$ is G, R, A, or S; $X_7$ is G or S; $X_8$ is S or absent; $X_9$ is S, Y or absent; $X_{10}$ is V, I or absent; $X_{11}$ is G or absent; $X_{12}$ is Y or absent; $X_{13}$ is A, E or absent;

in HVR-L1 (SEQ ID NO:115): $RASQX_1X_2X_3X_4X_5X_6A$, wherein $X_1$ is D, I or S; $X_2$ is V or I; $X_3$ is S, G or R; $X_4$ is T, I, N or R; $X_5$ is A or S; $X_6$ is V or L;

in HVR-L2 (SEQ ID NO:116): $X_1ASX_2LX_3S$, wherein $X_1$ is S, A, or V; $X_2$ is F, N or S; $X_3$ is Y or A;

in HVR-L3 (SEQ ID NO:117): $QQX_1X_2X_3X_4X_5X_6T$, wherein $X_1$ is S or A; $X_2$ is Y, K or N; $X_3$ is T, S, Y, M, R or A; $X_4$ is T, N, S, or F; $X_5$ is P or R; $X_6$ is P, Y, S or L.

In some embodiments, the following consensus sequences are provided:

in HVR-H1 (SEQ ID NO:118): $GFX_1X_2X_3GX_4WIH$, wherein $X_1$ is T or S, $X_2$ is F or L, $X_3$ is T or 5, $X_4$ is H, S or T;

in HVR-H2 (SEQ ID NO:119): $GWIX_1PYX_2X_3X_4X_5YYADSVKG$, wherein $X_1$ is S, N or A; $X_2$ is G, R or S; $X_3$ is G or R; $X_4$ is S, Y or H; $X_5$ is T, A or P;

in HVR-H3 (SEQ ID NO:120): $AREYX_1X_2WX_3X_4SX_5X_6GYX_7MDY$, wherein $X_1$ is S, N or P; $X_2$ is G or D; $X_3$ is G, R, or A; $X_4$ is G or S; $X_5$ is S or Y; $X_6$ is V or I; $X_7$ is A or E;

in HVR-L3 (SEQ ID NO:121): $QQSYX_1X_2X_3X_4T$, wherein $X_1$ is T, S or Y; $X_2$ is T, N, S or F; $X_3$ is P or R; $X_4$ is P, Y or S.

In another aspect, an anti-Axl antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:103, 105, 107 or 109. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-Axl antibody comprising that sequence retains the ability to bind to Axl. In certain embodiments, a total of 1 to 10 amino acids have been substituted, inserted and/or deleted in SEQ ID NO:103, 105, 107 or 109. In certain embodiments, substitutions, insertions, or deletions occur in regions outside the HVRs (i.e., in the FRs). Optionally, the anti-Axl antibody comprises the VH sequence in SEQ ID NO:103, 105, 107 or 109, including post-translational modifications of that sequence. In a particular embodiment, the VH comprises one, two or three HVRs selected from: (a) HVR-H1 comprising the amino acid sequence of SEQ ID NO:1, 7, 13, 19, 25, 31, 37, 43, 49, 55, 61, 67, 73, 79, 85, 91, or 97, (b) HVR-H2 comprising the amino acid sequence of SEQ ID NO:2, 8, 14, 20, 26, 32, 38, 44, 50, 56, 62, 68, 74, 80, 86, 92, or 98, and (c) HVR-H3 comprising the amino acid sequence of SEQ ID NO:3, 9, 15, 21, 27, 33, 39, 45, 51, 57, 63, 69, 75, 81, 87, 93 or 99. In a particular embodiment, the VH comprises one, two or three HVRs selected from: (a) HVR-H1 comprising the amino acid sequence of SEQ ID NO:7, (b) HVR-H2 comprising the amino acid sequence of SEQ ID NO:8, and (c) HVR-H3 comprising the amino acid sequence of SEQ ID NO:9.

In another aspect, an anti-Axl antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:104, 106, 108 or 110. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-Axl antibody comprising that sequence retains the ability to bind to PRO. In certain embodiments, a total of 1 to 10 amino acids have been substituted, inserted and/or deleted in SEQ ID NO:104, 106, 108 or 110. In certain embodiments, the substitutions, insertions, or deletions occur in regions outside the HVRs (i.e., in the FRs). Optionally, the anti-Axl antibody comprises the VL sequence in SEQ ID NO:104, 106, 108 or 110, including post-translational modifications of that sequence. In a particular embodiment, the VL comprises one, two or three HVRs selected from (a) HVR-L1 comprising the amino acid sequence of SEQ ID NO:4, 10, 16, 22, 28, 34, 40, 46, 52, 58, 64, 70, 76, 82, 88, 94, or 100; (b) HVR-L2 comprising the amino acid sequence of SEQ ID NO:5, 11, 17, 23, 29, 35, 41, 47, 53, 59, 65, 77, 83, 89, 95, or 101; and (c) HVR-L3 comprising the amino acid sequence of SEQ ID NO:6, 12, 18, 24, 30, 36, 42, 48, 54, 60, 66, 72, 78, 84, 90, 96 or 102. In a particular embodiment, the VL comprises one, two or three HVRs selected from (a) HVR-L1 comprising the amino acid sequence of SEQ ID NO:10; (b) HVR-L2 comprising the amino acid sequence of SEQ ID NO:11; and (c) HVR-L3 comprising the amino acid sequence of SEQ ID NO:12.

In another aspect, an anti-Axl antibody is provided, wherein the antibody comprises a VH as in any of the embodiments provided above. In some embodiments, the antibody further comprises a VL. In one embodiments, the antibody comprises the VH sequence in SEQ ID NO:103. In one embodiments, the antibody comprises the VH sequence in SEQ ID NO:105. In one embodiments, the antibody comprises the VH sequence in SEQ ID NO:107. In one embodiments, the antibody comprises the VH sequence in SEQ ID NO:109.

In another aspect, an anti-Axl antibody is provided, wherein the antibody comprises a VL as in any of the embodiments provided above. In some embodiments, the antibody further comprises a VH. In one embodiments, the antibody comprises the VL sequence in SEQ ID NO:104. In one embodiments, the antibody comprises the VL sequence in SEQ ID NO:106. In one embodiments, the antibody comprises the VL sequence in SEQ ID NO:108. In one embodiments, the antibody comprises the VL sequence in SEQ ID NO:110.

In another aspect, an anti-Axl antibody is provided, wherein the antibody comprises a VH as in any of the embodiments provided above, and a VL as in any of the embodiments provided above. In one embodiment, the antibody comprises the VH and VL sequences in SEQ ID NO:103 and SEQ ID NO:104, respectively, including post-translational modifications of those sequences. In one embodiment, the antibody comprises the VH and VL sequences in SEQ ID NO:105 and SEQ ID NO:106, respectively, including post-translational modifications of those sequences. In one embodiment, the antibody comprises the VH and VL sequences in SEQ ID NO:107 and SEQ ID NO:108, respectively, including post-translational modifications of those sequences. In one embodiment, the antibody comprises the VH and VL sequences in SEQ ID NO:109 and SEQ ID NO:110, respectively, including post-translational modifications of those sequences.

The antibodies of the invention can comprise any suitable framework variable domain sequence, provided binding activity to Axl is substantially retained. For example, in some embodiments, antibodies of the invention comprise a human subgroup III heavy chain framework consensus sequence. In one embodiment of these antibodies, the framework consensus sequence comprises a substitution at position 71, 73, and/or 78. In some embodiments of these antibodies, position 71 is A, 73 is T and/or 78 is A. In one embodiment, these antibodies comprise heavy chain variable domain framework sequences of huMAb4D5-8 (HERCEPTIN®, Genentech, Inc., South San Francisco, Calif., USA) (also referred to in U.S. Pat. Nos. 6,407,213 & 5,821,337, and Lee et al., J. Mol. Biol. (2004), 340(5):1073-1093). In one embodiment, these antibodies further comprise a human id light chain framework consensus sequence. In a particular embodiment, these antibodies comprise light chain HVR sequences of huMAb4D5-8 as described in U.S. Pat. Nos. 6,407,213 & 5,821,337.) In one embodiment, these antibodies comprise light chain variable domain sequences of huMAb4D5-8 (HERCEPTIN®, Genentech, Inc., South San Francisco, Calif., USA) (also referred to in U.S. Pat. Nos. 6,407,213 & 5,821,337, and Lee et al., J. Mol. Biol. (2004), 340(5):1073-1093). In one embodiment, an anti-Axl antibody comprises HVRs as in any of the above embodiments, and further comprises a VH and/or VL comprising a FR1, FR2, FR3 or FR4 sequence shown in FIG. 2, 3A-B, 4, 5 or 6.

In a further aspect, the invention provides an antibody that binds to the same epitope as an anti-Axl antibody provided herein. For example, in certain embodiments, an antibody is provided that binds to the same epitope as an anti-Axl antibody comprising a VH sequence of SEQ ID NO:103 and a VL sequence of SEQ ID NO:104. In certain embodiments, an antibody is provided that binds to the same epitope as an anti-Axl antibody comprising a VH sequence of SEQ ID NO:107 and a VL sequence of SEQ ID NO108. In certain embodiments, an antibody is provided that binds to an epitope within a fragment of Axl consisting of amino acids MAWRCPRMGRVPLAWCLALCGWAC-MAPRGTQAEESPFVGNPGNITGARGLTGTLRCQ LQVQGEPPEVHWLRDGQILELADSTQTQVPLGED-EQDDWIVVSQLRITSLQLSDTGQYQC LVFLGHQT-FVSQPGYVG (SEQ ID NO:111). In certain embodiments, an antibody is provided that binds to an epitope within a fragment of Axl consisting of amino acids ITVLPQQPRN-LHLVSRQPTELEVAWTPGLSGIYPLTHCTLQAVLSD-DGMGIQAGEPDPPEE PLTSQASVPPHQLRLGSLH-PHTPYHIRVACTSSQGPSSWTHWL (SEQ ID NO:130).

In a further aspect, the invention provides an antibody that competes for binding to human Axl with an anti-Axl antibody comprising a VH sequence of SEQ ID NO:103 and a VL sequence of SEQ ID NO:104. In certain embodiments, an antibody is provided that competes for binding to human Axl with an anti-Axl antibody comprising a VH sequence of SEQ ID NO:107 and a VL sequence of SEQ ID NO:108.

In a further aspect of the invention, an anti-Axl antibody according to any of the above embodiments is a monoclonal antibody, including a chimeric, humanized or human antibody. In one embodiment, an anti-Axl antibody is an antibody fragment, e.g., a Fv, Fab, Fab', scFv, diabody, or $F(ab')_2$ fragment. In another embodiment, the antibody is a full length antibody, e.g., an intact IgG antibody or other antibody class or isotype as defined herein.

In a further aspect, an anti-Axl antibody according to any of the above embodiments may incorporate any of the features, singly or in combination, as described in Sections 1-7 below:

1. Antibody Affinity

In certain embodiments, an antibody provided herein has a dissociation constant (Kd) of ≤1 μM, ≤100 nM, ≤10 nM, ≤1 nM, ≤0.1 nM, ≤0.01 nM, or ≤0.001 nM (e.g. $10^{-8}$M or less, e.g. from $10^{-8}$M to $10^{-13}$M, e.g., from $10^{-9}$M to $10^{-13}$ M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., J. Mol. Biol. 293:865-881 (1999)). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., Cancer Res. 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 μl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 μl/minute to achieve approximately 10 response units (RU) of coupled protein. Following the injection of antigen, 1 M ethanolamine is injected to block unreacted groups. For kinetics measurements, twofold serial dilutions of Fab (0.78 nM to 500 nM) are injected in PBS with 0.05% polysorbate 20 (TWEEN-20™) surfactant (PBST) at 25° C. at a flow rate of approximately 25 μl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., J. Mol. Biol. 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. Nat. Med. 9:129-134 (2003). For a review of scFv fragments, see, e.g., Pluckthün, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., Nat. Med. 9:129-134 (2003); and Hollinger et al., Proc. Natl. Acad. Sci. USA 90: 6444-6448 (1993). Triabodies and tetrabodies are also described in Hudson et al., Nat. Med. 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. E. coli or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., Proc. Natl. Acad. Sci. USA, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing SDR (a-CDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Human framework regions that may be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. Proc. Natl. Acad. Sci. USA, 89:4285

(1992); and Presta et al. J. Immunol., 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., J. Biol. Chem. 272:10678-10684 (1997) and Rosok et al., J. Biol. Chem. 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, Curr. Opin. Pharmacol. 5: 368-74 (2001) and Lonberg, Curr. Opin. Immunol. 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., U.S. Pat. Nos. 6,075,181 and 6,150,584 describing XENOMOUSE™ technology; U.S. Pat. No. 5,770,429 describing HuMab® technology; U.S. Pat. No. 7,041,870 describing K-M MOUSE® technology, and U.S. Patent Application Publication No. US 2007/0061900, describing VelocimMouse® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor J. Immunol., 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991).) Human antibodies generated via human B-cell hybridoma technology are also described in Li et al., Proc. Natl. Acad. Sci. USA, 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, Histology & Histopathology, 20(3):927-937 (2005) and Vollmers and Brandlein, Methods & Findings in Exp. & Clin. Pharmacology, 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in Methods in Molecular Biology 178: 1-37 (O'Brien et al., ed., Human Press, Totowa, N.J., 2001) and further described, e.g., in the McCafferty et al., Nature 348:552-554; Clackson et al., Nature 352: 624-628 (1991); Marks et al., J. Mol. Biol. 222: 581-597 (1992); Marks and Bradbury, in Methods in Molecular Biology 248:161-175 (Lo, ed., Human Press, Totowa, N.J., 2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., Ann. Rev. Immunol., 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., EMBO J, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, J. Mol. Biol., 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for Axl and the other is for any other antigen. In certain embodiments, bispecific antibodies may bind to two different epitopes of Axl. Bispecific antibodies may also be used to localize cytotoxic agents to cells which express Axl. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, Nature 305: 537 (1983)), WO 93/08829, and Traunecker et al., EMBO J. 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., Science 229: 81 (1985)); using leucine zippers to produce bi-specific antibodies (see, e.g., Kostelny et al., J. Immunol., 148(5):1547-1553 (1992)); using "diabody" technology for making bispecific antibody fragments (see, e.g., Hollinger et al., Proc. Natl. Acad. Sci. USA, 90:6444-6448 (1993)); and using single-chain Fv (sFv) dimers (see, e.g. Gruber et al., J. Immunol. 152:5368 (1994)); and preparing trispecific antibodies as described, e.g., in Tutt et al. J. Immunol. 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to Axl as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "conservative substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, Methods Mol. Biol. 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in Methods in Molecular Biology 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) Science, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. TIBTECH 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. J. Mol. Biol. 336:1239-1249 (2004); Yamane-Ohnuki et al. Biotech. Bioeng. 87: 614 (2004). Examples of cell lines capable of producing defucosylated antibodies include Lec13 CHO cells deficient in protein fucosylation (Ripka et al. Arch. Biochem. Biophys. 249: 533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. Biotech. Bioeng. 87: 614 (2004); Kanda, Y. et al., Biotechnol. Bioeng., 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol 9:457-492 (1991). Non-limiting examples of in vitro assays to assess ADCC activity of a molecule of interest is described in U.S. Pat. No. 5,500,362 (see, e.g. Hellstrom, I. et al. Proc. Nat'l Acad. Sci. USA 83:7059-7063 (1986)) and Hellstrom, I et al., Proc. Nat'l Acad. Sci. USA 82:1499-1502 (1985); U.S. Pat. No. 5,821,337 (see Bruggemann, M. et al., J. Exp. Med. 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. Proc. Nat'l Acad. Sci. USA 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., J. Immunol. Methods 202:163 (1996); Cragg, M. S. et al., Blood 101:1045-1052 (2003); and Cragg, M. S, and M. J. Glennie, Blood 103:2738-2743 (2004)). FcRn binding and in vivo clearance/half life determinations can also be performed using methods known in the art (see, e.g., Petkova, S. B. et al., Int'l. Immunol. 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., J. Biol. Chem. 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. J. Immunol. 164: 4178-4184 (2000).

Antibodies with increased half lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, Nature 322:738-40 (1988); U.S. Pat. No. 5,648,260; U.S. Pat. No. 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and 5400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., Proc. Natl. Acad. Sci. USA 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an anti-Axl antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-Axl antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-Axl antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, N.J., 2003), pp. 245-254, describing expression of antibody fragments in E. coli.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, Nat. Biotech. 22:1409-1414 (2004), and Li et al., Nat. Biotech. 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR$^-$ CHO cells (Urlaub et al., Proc. Natl. Acad. Sci. USA 77:4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J.), pp. 255-268 (2003).

C. Assays

Anti-Axl antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, Western blot, etc.

In another aspect, competition assays may be used to identify an antibody that competes with one or more of antibodies 327.6, 327.6.S2, 327.6.511, 327.6.550, 327.6.S52, 327.6.S65, 327.42, 327.42.S8, 327.42.S31, 327.42.S13, 327.42.S43, 327.42.S52, 327.42.S63, 327.42.S73, 327.42.H2, 327.42.H4, and/or 327.42.H20 for binding to Axl. In certain embodiments, such a competing antibody binds to the same epitope (e.g., a linear or a conformational epitope) that is bound by 327.6, 327.6.S2, 327.6.S11, 327.6.550, 327.6.S52, 327.6.S65, 327.42, 327.42.S8, 327.42.S31, 327.42.S13, 327.42.S43, 327.42.S52, 327.42.S63, 327.42.S73, 327.42.H2, 327.42.H4, and/or 327.42.H20. Detailed exemplary methods for mapping an epitope to which an antibody binds are provided in Morris (1996) "Epitope Mapping Protocols," in Methods in Molecular Biology vol. 66 (Humana Press, Totowa, N.J.).

In an exemplary competition assay, immobilized Axl is incubated in a solution comprising a first labeled antibody that binds to Axl (e.g., 327.6, 327.6.S2, 327.6.511, 327.6.550, 327.6.S52, 327.6.S65, 327.42, 327.42.S8, 327.42.S31, 327.42.S13, 327.42.S43, 327.42.S52, 327.42.S63, 327.42.S73, 327.42.H2, 327.42.H4, and/or 327.42.H20) and a second unlabeled antibody that is being tested for its ability to compete with the first antibody for binding to Axl. The second antibody may be present in a hybridoma supernatant. As a control, immobilized Axl is incubated in a solution comprising the first labeled antibody but not the second unlabeled antibody. After incubation under conditions permissive for binding of the first antibody to Axl, excess unbound antibody is removed, and the amount of label associated with immobilized Axl is measured. If the amount of label associated with immobilized Axl is substantially reduced in the test sample relative to the control sample, then that indicates that the second antibody is competing with the first antibody for binding to Axl. See Harlow and Lane (1988) Antibodies: A Laboratory Manual ch. 14 (Cold Spring Harbor Laboratory, Cold Spring Harbor, N.Y.).

2. Activity Assays

In one aspect, assays are provided for identifying anti-Axl antibodies thereof having biological activity. Biological activity may include, e.g., inhibition of Gas6 binding to Axl, inhibition of Axl activation, inhibition of Axl downstream molecular signaling, inhibition of Axl expression (e.g., Axl cell surface expression or total Axl expression in a cell, such as a tumor cell), inhibition of inflammatory cytokine secretion, promotion of apoptosis (e.g., by inhibiting Gas6-mediated inhibition of apoptosis), inhibition of intratumoral vasculature, inhibition of tumor stromal Axl activity and/or expression and/or inhibition of metastasis. Antibodies having such biological activity in vivo and/or in vitro are also provided.

In certain embodiments, an antibody of the invention is tested for such biological activity. In certain embodiments, an antibody is tested for its ability to promote apoptosis in vitro (e.g., apoptosis of a tumor cell). Exemplary methods for determining cell growth and/or proliferation and/or apoptosis include, for example, BrdU incorporation assay, MTT, [3H]-thymidine incorporation (e.g., TopCount assay (PerkinElmer)), cell viability assays (e.g., CellTiter-Glo (Promega)), DNA fragmentation assays, caspase activation assays, tryptan blue exclusion, chromatin morphology assays and the like.

In certain embodiments, an antibody is tested for inhibition of Axl expression, e.g., using methods described and exemplified herein. In one embodiment, anti-Axl antibody is incubated with suitable test cells, e.g., NSCLC cells A549 and after a suitable period of time, cell lysates are harvested and examined for total Axl levels. FACS analysis may also be used to examine surface Axl receptor levels following incubation with candidate anti-Axl antibodies. In one embodiment, a tumor sample is examined for Axl expression following treatment with anti-Axl antibody.

In certain embodiments, an antibody of the invention is tested for its ability to inhibit inflammatory cytokine section, e.g., as described exemplified herein.

In certain embodiments, an antibody of the invention is tested for its ability to reduce intratumoral vasculature and/or inhibit tumor stromal Axl activity and/or expression, e.g., as exemplified herein. In some embodiments, tumor stromal Axl activity is metastasis or development of intratumor vasculature.

In certain embodiments, an antibody of the invention is tested for its ability to inhibit cell growth or proliferation in vitro. Assays for inhibition of cell growth or proliferation are well known in the art. Certain assays for cell proliferation, exemplified by the "cell killing" assays described herein, measure cell viability. One such assay is the CellTiter-Glo™ Luminescent Cell Viability Assay, which is commercially available from Promega (Madison, Wis.). That assay determines the number of viable cells in culture based on quantitation of ATP present, which is an indication of metabolically active cells. See Crouch et al (1993) J. Immunol. Meth. 160:81-88, U.S. Pat. No. 6,602,677. The assay may be conducted in 96- or 384-well format, making it amenable to automated high-throughput screening (HTS). See Cree et al (1995) AntiCancer Drugs 6:398-404. The assay procedure involves adding a single reagent (CellTiter-Glo® Reagent) directly to cultured cells. This results in cell lysis and generation of a luminescent signal produced by a luciferase reaction. The luminescent signal is proportional to the amount of ATP present, which is directly proportional to the number of viable cells present in culture. Data can be recorded by luminometer or CCD camera imaging device. The luminescence output is expressed as relative light units (RLU).

Another assay for cell proliferation is the "MTT" assay, a colorimetric assay that measures the oxidation of 3-(4,5-dimethylthiazol-2-yl)-2,5-diphenyltetrazolium bromide to formazan by mitochondrial reductase. Like the CellTiter-Glo™ assay, this assay indicates the number of metabolically active cells present in a cell culture. See, e.g., Mosmann (1983) J. Immunol. Meth. 65:55-63, and Zhang et al. (2005) Cancer Res. 65:3877-3882.

Cells for use in any of the above in vitro assays include cells or cell lines that naturally express Axl or that have been engineered to express Axl. Such cells include tumor cells that overexpress Axl relative to normal cells of the same tissue origin. Such cells also include cell lines (including tumor cell lines) that express Axl and cell lines that do not normally express Axl but have been transfected with nucleic acid encoding Axl. Exemplary cell lines provided herein for use in any of the above in vitro assays include NSCLC cell line A549, NSCLC cell line H1299, and breast cancer cell line MDA-MB231.

In one aspect, an anti-Axl antibody thereof is tested for its ability to inhibit cell growth or proliferation in vivo. In certain embodiments, an anti-Axl antibody thereof is tested for its ability to inhibit tumor growth in vivo. In vivo model systems, such as xenograft models, can be used for such testing. In an exemplary xenograft system, human tumor cells are introduced into a suitably immunocompromised non-human animal, e.g., an athymic "nude" mouse. An antibody of the invention is administered to the animal. The ability of the antibody to inhibit or decrease tumor growth is measured. In certain embodiments of the above xenograft system, the human tumor cells are tumor cells from a human patient. Such xenograft models are commercially available from Oncotest GmbH (Frieberg, Germany). In certain embodiments, the human tumor cells are cells from a human tumor cell line, such as MDA-MB-231 breast cancer cells or A549 non-small cell lung cancer cells. In certain embodiments, the human tumor cells are introduced into a suitably immunocompromised non-human animal by subcutaneous injection or by transplantation into a suitable site, such as a mammary fat pad.

It is understood that any of the above assays may be carried out using an immunoconjugate of the invention in place of or in addition to an anti-Axl antibody.

It is understood that any of the above assays may be carried out using anti-Axl antibody and an additional therapeutic agent, such as a VEGF antagonist and/or an EGFR antagonist and/or a chemotherapeutic agent.

D. Immunoconjugates

The invention also provides immunoconjugates comprising an anti-Axl antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., Cancer Res. 53:3336-3342 (1993); and Lode et al., Cancer Res. 58:2925-2928 (1998)); an anthracycline such as daunomycin or doxorubicin (see Kratz et al., Current Med. Chem. 13:477-523 (2006); Jeffrey et al., Bioorganic & Med. Chem. Letters 16:358-362 (2006); Torgov et al., Bioconj. Chem. 16:717-721 (2005); Nagy et al., Proc. Natl. Acad. Sci. USA 97:829-834 (2000); Dubowchik et al., Bioorg. & Med. Chem. Letters 12:1529-1532 (2002); King et al., J. Med. Chem. 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from Pseudomonas aeruginosa), ricin A chain, abrin A chain, modeccin A chain, alpha-sarcin, Aleurites fordii proteins, dianthin proteins, Phytolaca americana proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., Cancer Res. 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SLAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

E. Methods and Compositions for Diagnostics and Detection

In certain embodiments, any of the anti-Axl antibodies provided herein is useful for detecting the presence of Axl in a biological sample. The term "detecting" as used herein encompasses quantitative or qualitative detection. In certain embodiments, a biological sample comprises a cell or tissue, such as breast, pancreas, esophagus, lung and/or brain.

In one embodiment, an anti-Axl antibody for use in a method of diagnosis or detection is provided. In a further aspect, a method of detecting the presence of Axl in a biological sample is provided. In certain embodiments, the method comprises contacting the biological sample with an anti-Axl antibody as described herein under conditions permissive for binding of the anti-Axl antibody to Axl, and detecting whether a complex is formed between the anti-Axl antibody and Axl. Such method may be an in vitro or in vivo method. In one embodiment, an anti-Axl antibody is used to select subjects eligible for therapy with an anti-Axl antibody, e.g. where Axl is a biomarker for selection of patients.

Exemplary disorders that may be diagnosed using an antibody of the invention include cancer (for example, cancer of the breast, lung, pancreas, brain, kidney, ovary, stomach, leukemia, uterine endometrium, colon, prostate, thyroid, liver, osteosarcoma, and/or melanoma).

In certain embodiments, labeled anti-Axl antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an anti-Axl antibody as described herein are prepared by mixing such antibody having the desired degree of purity with one or more optional pharmaceutically acceptable carriers (Remington's Pharmaceutical Sciences 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. For example, it may be desirable to further provide an EGFR antagonist (such as erlotinib), an anti-angiogenic agent (such as VEGF antagonist, such as an anti-VEGF antibody) or a chemotherapeutic agent (such as a taxoid or a platinum agent).

Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the anti-Axl antibodies provided herein may be used in therapeutic methods.

In one aspect, an anti-Axl antibody for use as a medicament is provided. In further aspects, an anti-Axl antibody for use in treating cancer (e.g., breast cancer, non-small cell lung cancer, pancreatic cancer, brain cancer, cancer of pancreas, brain, kidney, ovary, stomach, leukemia, uterine endometrium, colon, prostate, thyroid, liver, osteosarcoma, and/or melanoma) is provided. In certain embodiments, an anti-Axl antibody for use in a method of treatment is provided. In certain embodiments, the invention provides an anti-Axl antibody for use in a method of treating an individual having cancer comprising administering to the individual an effective amount of the anti-Axl antibody. In certain embodiments, the invention provides an anti-Axl antibody for use in a method of treating an individual having an immune disorder (e.g., an autoimmune disorder), a cardiovascular disorder (e.g., atherosclerosis, hypertension, thrombosis), an infectious disease (e.g., Ebola virus, Marburg virus) or diabetes, comprising administering to the individual an effective amount of the anti-Axl antibody. In one such embodiment, the method further comprises administering to the individual an effective amount of at least one additional therapeutic agent, e.g., as described below. In further embodiments, the invention provides an anti-Axl antibody for use in inhibiting angiogenesis, inhibiting cell proliferation, inhibiting immune function, inhibiting inflammatory cytokine secretion (e.g., from tumor-associated macrophages), inhibiting tumor vasculature (e.g., intratumoral vasculature or tumor-associated vasculature), and/or inhibiting tumor stromal function.

In certain embodiments, the invention provides an anti-Axl antibody for use in a method of inhibiting angiogenesis, inhibiting cell proliferation, inhibiting immune function, inhibiting inflammatory cytokine secretion (e.g., from tumor-associated macrophages), inhibiting tumor vasculature (e.g., intratumoral vasculature or tumor-associated vasculature), and/or inhibiting tumor stromal function in an individual comprising administering to the individual an effective of the anti-Axl antibody to inhibit angiogenesis, inhibit cell proliferation, inhibit immune function, inhibit inflammatory cytokine secretion (e.g., from tumor-associated macrophages), inhibit tumor vasculature development (e.g., intratumoral vasculature or tumor-associated vasculature), and/or inhibit tumor stromal function. An "individual" according to any of the above embodiments is preferably a human.

In a further aspect, the invention provides for the use of an anti-Axl antibody in the manufacture or preparation of a medicament. In one embodiment, the medicament is for treatment of cancer (in some embodiments, breast cancer, non-small cell lung cancer, pancreatic cancer, brain cancer, cancer of the pancreas, brain, kidney, ovary, stomach, leukemia, uterine endometrium, colon, prostate, thyroid, liver, osteosarcoma, and/or melanoma). In a further embodiment, the medicament is for use in a method of treating cancer comprising administering to an individual having cancer an effective amount of the medicament. In a further embodiment, the medicament is for use in a method of treating an immune disorder (e.g., an autoimmune disorder), a cardiovascular disorder (e.g., atherosclerosis, hypertension, thrombosis), an infectious disease (e.g., Ebola virus, Marburg virus) or diabetes, comprising administering to the individual an effective amount of the anti-Axl antibody. In one such embodiment, the method further comprises administering to the individual an effective amount of at least one additional therapeutic agent, e.g., as described below. In a further embodiment, the medicament is for inhibiting angiogenesis, inhibiting cell proliferation, inhibiting immune function, inhibiting inflammatory cytokine secretion (e.g., from tumor-associated macrophages), inhibiting tumor vasculature (e.g., intratumoral vasculature or tumor-associated vasculature), and/or inhibiting tumor stromal function. In a further embodiment, the medicament is for use in a method of inhibiting angiogenesis, inhibiting cell proliferation, inhibiting immune function, inhibiting inflammatory cytokine secretion (e.g., from tumor-associated macrophages), inhibiting tumor vasculature (e.g., intratumoral vasculature or tumor-associated vasculature), and/or inhibiting tumor stromal function in an individual comprising administering to the individual an amount effective of the medicament to inhibit angiogenesis, inhibit cell proliferation, promote immune function, induce inflammatory cytokine section (e.g., from tumor-associated macrophages), inhibit tumor vasculature development (e.g., intratumoral vasculature or tumor-associated vasculature), and/or inhibit tumor stromal function. An "individual" according to any of the above embodiments may be a human.

In a further aspect, the invention provides a method for treating a cancer. In one embodiment, the method comprises administering to an individual having such cancer an effective amount of an anti-Axl antibody. In one such embodiment, the method further comprises administering to the individual an effective amount of at least one additional therapeutic agent, as described below. An "individual" according to any of the above embodiments may be a human.

In a further aspect, the invention provides a method for treating an immune disorder (e.g., an autoimmune disorder), a cardiovascular disorder (e.g., atherosclerosis, hypertension, thrombosis), an infectious disease (e.g., Ebola virus, Marburg virus) or diabetes. In one such embodiment, the method further comprises administering to the individual an effective amount of at least one additional therapeutic agent, as described below. An "individual" according to any of the above embodiments may be a human.

In a further aspect, the invention provides a method for inhibiting angiogenesis, inhibiting cell proliferation, inhibiting immune function, inhibiting inflammatory cytokine secretion (e.g., from tumor-associated macrophages), inhibiting tumor vasculature (e.g., intratumoral vasculature or tumor-associated vasculature), and/or inhibiting tumor stromal function in an individual. In one embodiment, the method comprises administering to the individual an effective amount of an anti-Axl antibody to inhibit angiogenesis, inhibit cell proliferation, promote immune function, induce inflammatory cytokine section (e.g., from tumor-associated macrophages), inhibit tumor vasculature development (e.g., intratumoral vasculature or tumor-associated vasculature), and/or inhibit tumor stromal function. In one embodiment, an "individual" is a human.

In a further aspect, the invention provides pharmaceutical formulations comprising any of the anti-Axl antibodies provided herein, e.g., for use in any of the above therapeutic methods. In one embodiment, a pharmaceutical formulation comprises any of the anti-Axl antibodies provided herein and a pharmaceutically acceptable carrier. In another embodiment, a pharmaceutical formulation comprises any of the anti-Axl antibodies provided herein and at least one additional therapeutic agent, e.g., as described below.

Antibodies of the invention can be used either alone or in combination with other agents in a therapy. For instance, an antibody of the invention may be co-administered with at least one additional therapeutic agent. In certain embodiments, an additional therapeutic agent is an anti-angiogenic agent. In certain embodiments, an additional therapeutic agent is a VEGF antagonist (in some embodiments, an anti-VEGF antibody, for example bevacizumab). In certain embodiments, an additional therapeutic agent is an EGFR antagonist (in some embodiment, erlotinib). In certain embodiments, an additional therapeutic agent is a chemotherapeutic agent and/or a cytostatic agent. In certain embodiments, an additional therapeutic agent is a taxoid (e.g., paclitaxel) and/or a platinum agent (e.g., carboplatinum).

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent and/or adjuvant. Antibodies of the invention can also be used in combination with radiation therapy.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 μg/kg to 40 mg/kg of antibody can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using an immunoconjugate of the invention in place of or in addition to an anti-Axl antibody.

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-Axl antibody.

III. Examples

Materials and Methods

Antibodies and Cell Lines.

Antibodies were obtained from the following suppliers: Mouse monoclonal antibody (mAb) against human Axl (Abnova, Taiwan), phospho-Akt mouse mAb and Akt polyclonal antibody (Cell Signaling). Mouse recombinant Gas6 and ELISA kit for phospho-Axl were purchased from R&D System. Human carcinoma cell lines were obtained from ATCC, and cultured in PRMI1640 medium supplemented with 10% FBS. Hybridoma anti-human Axl monoclonal antibodies 12A11 and 3G9 were provided by Genentech (see Li (2009)).

Generation of Phage Anti-Axl Monoclonal Antibodies.

For antibody generation, human phage antibody libraries with synthetic diversities in the selected complementary determining regions (H1, H2, H3), mimicking the natural diversity of human IgG repertoire were used for panning. Fab fragments were displayed bivalently on the surface of M13 bacteriophage particles (Lee et al, 2004). The phage antibody libraries were panned against human and murine Axl ECD in alternative rounds. Phage antibodies that bound to human Axl ECD-His and murine Axl ECD-Fc fusion protein were identified by ELISA and DNA sequencing, and antibody clones were reformatted to express full-length IgGs (Liang et al, 2007). Individual clones were transiently expressed in mammalian cells and purified with protein A columns (Carter et al, 1992).

Phage clones were screened for their ability to inhibit Gas6-dependent proliferation of Baf3-Axl cells. Two clones that exhibited highest potency in inhibition of Baf3Axl cell proliferation were chosen for affinity maturation.

For affinity maturation, phagemid displaying monovalent Fab on the surface of M13 bacteriophage (Liang et al, 2007) served as the library template for grafting light chain ($V_L$) and heavy chain ($V_H$) variable domains of the phage Ab. A soft randomization strategy was adopted for affinity maturation as described (Liang et al, 2007), and a high-throughput single-point competitive phage ELISA was used to rapidly screen for high-affinity clones as described (Sidhu et al, 2004).

Affinity Measurement of Anti-Axl Antibodies.

For binding affinity determinations of anti-Axl antibodies, surface Plasmon Resonance (SRP) measurement with a BIAcore™-3000 instrument was used. To measure the affinity between anti-Axl antibodies and human Axl ECD-His protein, Anti-Axl human IgG was captured by CM5 biosensor chips coated with mouse anti-human IgG to achieve approximately 250 response units (RU). For kinetics measurements, two-fold serial dilutions of human Axl ECD-His (440 nM-28 nM) were injected in PBT buffer (PBS with 0.05% Tween 20) at 25° C. with a flow rate of 30 μl/min. Association rates ($k_{on}$) and dissociation rates ($k_{off}$) were calculated using a simple one-to-one Langmuir binding model (BIAcore Evaluation Software version 3.2). The equilibrium dissociation constant ($K_D$) was calculated as the $k_{off}/k_{on}$, ratio. To measure the affinity of anti-Axl antibodies to murine Axl ECD-Fc fusion protein, murine Axl ECD human IgG fusion protein was captured by CM5 biosensor chips coated mouse anti-human IgG to achieve approximately 150 response units (RU). For kinetics measurements, two-fold serial dilutions of the anti-Axl Fab fragment (200 nM-12 nM) were injected in PBST buffer (PBS with 0.05% Tween 20) at 25° C. with a flow rate of 30 μl/min.

Cell Proliferation Assay.

Cells were seeded at 5000 cells/well in 96-well plates and treated with Axl mAb at various concentrations for 72 hours. Cell proliferation was measured using CellTiter-Glo Luminescent Cell Viability Assay (Promega) according to manufacturer's instructions.

ELISA and Fluorescence-Activated Cell Sorting (FACS).

ELISA assays were performed as follows: goat anti-human IgG Fc coated plates were blocking with 0.5% BSA, PBS, 0.05% Tween 20 (PBST). For cross reaction assay, coated plates were incubated with human Axl.Fc, mouse Axl.Fc or human Mer.Fc, Tyro-3.Fc for 1 hr at room temperature, washed four times in PBST, incubated with anti-Axl mAbs and HRP-conjugated anti-mouse Ig. For binding assay, coated plates were incubated with human Axl.Fc for 1 hr at room temperature, washed four times in PBST, incubated with rmGas 6 and anti-Axl mAbs for 1 hr at room temperature. Plates were washed four times in PBST, incubated with biotinylated anti-mGas6 and strepavidin-HRP. Secreted Ang-2 and DKK3 was measured using R&D ELISA kit, according to the manufacturer's instruction. Axl expression on cell surface was determined by FACS using standard techniques. Briefly, cells were harvested, stained with anti-Axl mAb (12A11, 10 ug/ml) for 30 mins on ice, washed twice in PBS, and then staining with PE-conjugated second antibody. To determine antibodies blocking of Gas6 binding to Axl on cell surface, cells were harvested, stained with anti-Axl mAbs for 30-mins and incubated with rmGas6 for 30-mins on ice. They were washed twice in PBS, and stained with biotinylated anti-Gas6 and PE-conjugated strepavidin. Samples were analyzed on BD FACScalibur Flow Cytometer.

Xenograft Experiments.

All studies were conducted in accordance with the "Guide for the Care and Use of Laboratory Animals" (NIH), and approved by the Institutional Animal Care and Used Committee (IACUC). A total of $5\times10^6$ (A549) or $10^7$ cells in matrigel (MDA-MB-231) were implanted subcutaneously into right flank of nude (A549) or SCID mice (MDA-MB-231), respectively. When the average tumor sized reached 100 $mm^3$, mice were randomized and divided into different treatment groups (n=10 for each group). Anti-Axl or control IgG1 antibodies were at administrated at 10-30 mg/kg, anti-VEGF at 1-2 mg/kg, via intraperitoneal injection (IP), twice weekly. Erlotinib was administrated by oral gavage at 100 mg/kg/day. Paclitaxel and carboplatin were administrated subcutaneously at 6.25 mg/kg/day for 5 days, and 100 mg/kg for a single dose, respectively, at the beginning of the treatment. Statistic analyses were performed using Anova two-way for comparison of tumor growth in different treatment groups.

For pharmacodynamic (PD) studies, mice were treated with antibodies for 0, 24, 72 and 168 hours. At each time point, tumors were excised, processed for immunohistochemical staining and image analysis, and used to generate cell lysates for Western blot analysis.

For metastasis studies, $5\times10^5$ MDA-MB-231 cells stably transfected with a luciferase reporter gene (Li et al, 2009) were implanted into SCID mice via tail vein injection. Metastasis of tumor cells to various organs was monitor by bioluminescence detection as described (Li et al, 2009).

Immunohistochemistry.

Xenograft tumor samples were fixed in 10% neutral buffered formalin, processed, embedded in paraffin, and sectioned at 4 μm. Thin sections were then treated with primary antibodies for Ki67, cleaved caspase 3 and MECA32, followed by biotinylated secondary antibodies and the DAB chromagen.

Primary human breast cancer tissue microarray was obtained from Cureline Inc, including ductal and metastatic adenocarcinomas. Axl IHC was performed using anti-Axl monoclonal antibody described previously (Li et al, 2009), and macrophages were stained using CD68. For dual Axl/CD68 IHC, Axl staining was performed first at 2 μg/ml using Vector ABC Elite HRP reagents and DAB substrate. CD68 staining was run sequentially at 0.5 μg/ml, also using ABC Elite-HRP reagents but Vector SG chromogen (Blue/Grey) instead. A second target antigen retrieval step was performed in between the two complexes to elute off the first complex in order to avoid the cross reactivity of the two markers.

Vascular Density Measurement and Data Analysis.

Tumor samples were stained with MECA32, a pan endothelial cell marker. Images were acquired by the Ariol SL-50 automated slide scanning platform (Genetix Ltd.; Hampshire, UK) at 100× final magnification. Tumor-specific areas were exported for analysis in the Metamorph software package (MDS Analytical Technologies; Ontario, Canada) as individual 8-bit images. The brown DAB-specific staining was isolated from the Hematoxylin counterstain using a blue-normalization algorithm as described (Brey et al, 2003). A segmentation algorithm identified vessels, and removed noise based on size and shape. Cells were identified as either tumor or non-tumor based on size, shape, and density of Hematoxylin staining. Non-tumor areas were identified by the density of non-tumor cells versus tumor cells. After analysis was complete, images were reviewed manually to remove artifacts identified incorrectly as vessels or tumor areas. Area measurements were recorded for individual vessels, as well as the tumor and non-tumor areas in each image. Raw values based on image analysis were analyzed using the JMP 8.0 software (SAS Institute, Inc. North Carolina, USA). A student's t test was performed to compare each pair of means, with $p<0.05$.

Isolation of Tumor-Associated Macrophages (TAM) and Detection of Secreted Cytokines.

Tumors were dissected, chopped into small pieces and incubated in RPMI1640 medium with 2.5% FBS, 0.2 units/ml Liberase Blendzymes II and 5 units/ml DNaseI, (Roche). Tumor cells were disassociated using MACS Dissociator (Miltenyi Biotec) and maintained for 20 minutes at room temperature. EDTA (final concentration 0.002%) was added to stop the reaction. Single cell suspensions were prepared, and red blood cells were removed using RBC lysis buffer (eBioscience). Cells were resuspended at $10^7$ cells/ml in PBS containing 1% FBS and incubated with 20 g/ml FcRII, III and IV for 20 minutes. Anti-F4/80-PE (eBioscience) and anti-CD11c-APC (BD Pharmingen) (0.2 μg/$10^6$ cells) were added and incubated for 30 minutes on ice. F4/80 and CD11c positive cells were sorted by FACSAria (BD Biosciences). A total of $2\times10^5$ F4/80 and CD11c positive cells were seeded in 96-well plate and cultured overnight. Cultured media was collected and the levels of cytokines and chemokines were determined using Bio-Plex mouse cytokine assays (Bio-Rad) according to manufacturer's instructions.

Epitope Mapping

Axl-2 (PRK HuAxl(1-134Aa)/HuIgG1Fc), Axl-3 (PRK HuAxl(1-221Aa)/HuIgG1Fc), Axl-4 (PRK HuAxl(1-324Aa)/HuIgG1Fc), and Axl-5 (PRK HuAxl(1-435Aa)/HuIgG1Fc) plasmid constructs were made by standard molecular-biology techniques. All plasmids were confirmed by direct sequencing and/or restriction digestion. Plasmids encoding various portion of Axl extracellular domain (aa1-134, aa1-221, aa1-324, aa1-435) were in vitro transcribed and translated using Promega L2080 TNT SP6 Quick transcription/translation system kit and were used as antigens in ELISA. Axl portions used in these experiments included: Amino acids 1-134 of human Axl (comprising Ig1 of Axl): MAWRCPRMGRVPLAWCLALCGWAC-MAPRGTQAEESPFVGNPGNITGARGLTGTLR CQLQVQGEPPEVHWLRDGQILELADSTQTQV-PLGEDEQDDWIVVSQLRITSLQLSDTGQY QCLVFL-GHQTFVSQPGYVG (SEQ ID NO:111), and amino acids 221-324 of human Axl (comprising Axl fibronectin domain): ITVLPQQPRNLHLVSRQPTELEVAWTPGLSGI-YPLTHCTLQAVLSDD GMGIQAGEPDPPEEPLTSQAS-VPPHQLRLGSLHPHTPYHIRVACTSSQGPSSWTHWL (SEQ ID NO:130).

Antibody Competition Experiments.

To determine whether phage anti-Axl mabs YW327.6 or YW327.42 competed with hybridoma anti-Axl mAbs 12A11 and 3G9, A549 cells were co-stained with an anti-Axl phage antibody (each at 50 μg/ml) and a hybridoma anti-Axl antibody (each at 10 μg/ml) for 30 minutes. Cells were washed twice in PBS, and stained with anti-mouse Ig-PE. Samples were analyzed on BD FACScalibur Flow Cytometer (BD Biosciences) as described above for FACS analysis.

Results

Generation of a Phage Derived Monoclonal Antibody that Blocks Axl Function.

To identify antibodies that cross-react with murine and human Axl, we employed phage-displayed antibody libraries with synthetic diversities in the selected complementary determining regions, mimicking the natural diversity of human IgG antibodies (Lee et al, 2004). Phage antibodies that bound to both human and murine Axl ECD were identified by ELISA and DNA sequencing, and antibody clones were reformatted to express full-length IgGs (Liang et al, 2007). A panel of full length IgGs was then screened for their ability to inhibit Gas6-dependent growth of Baf3Axl cells (Li et al, 2009), and one of the clones YW327.6 was affinity matured and purified.

Affinity matured Axl mAb YW327.6S2 binds to both human and murine Axl with high affinity, with a Kd of about 1 nM, and 545 pM, respectively (FIG. 7A-B). Specifically, Ka was $1.7\times10^5$, kd was $1.7\times10^4$, and KD was $9.9\times10^{-10}$. This antibody also binds to cynomolgus Axl, but it does not cross-react with related receptors Tyro3 and Mer (FIG. 7C). YW327.6S2 blocks binding of ligand Gas6 to Axl as demonstrated in both a cell free ELISA and on cell surface by FACS, in a dose-dependent manner (FIG. 7D-E).

Affinity matured Axl Mabs YW327.6S11, YW327.42S8 and YW327.42S31 were also characterized. YW327.6S11, YW327.42S8 and YW327.42S31 bind both human and murine Axl with high affinity. For example, biacore analysis of antibody binding to human Axl resulted in the following:

| Hu Axl | Ka | kd | KD |
|---|---|---|---|
| YW327.6S11 | $1.7\times10^5$ | $1.7\times10^4$ | $1.3\times10^9$ |
| YW327.42S8 | $5.2.\times10^4$ | $1.3\times10^4$ | $2.5\times10^9$ |
| YW327.42S31 | $6.3\times10^4$ | $1.5\times10^4$ | $2.4\times10^9$ |

These antibodies do not cross-react with Tyro3 and Mer. YW327.6S2 (and parent antibody YW 327.6) blocks binding of ligand Gas6 to Axl, while YW327.42S8 and YW327.42S31 (and parent Mab YW327.42) do not block binding of ligand Gas6 to Axl.

Axl Epitope Analysis.

Axl antibody binding to various portions of human Axl extracellular domain was analyzed using ELISA. The results were obtained.

| | YW327.6 | YW327.42 |
|---|---|---|
| Axl2 (aa1-134) | + | – |
| Axl-3 (aa1-221) | + | – |
| Axl-4 (aa1-324) | + | + |

YW327.6 bound to Axl-Fc fusions comprising amino acids 1-134 of human Axl. By contrast, YW327.42 bound an Axl-Fc fusion comprising amino acids 1-324 of human Axl, but did not bind Axl Fc fusions comprising amino acids 1-134, and 1-221. Thus, we concluded that YW327.6 binds a polypeptide consisting of amino acids 1-134 of human Axl, and that human Axl amino acids 222-234 was required for YW327.42 binding. Amino acids 1-134 contains Axl IgI domain, and amino acids 222-234 contain Axl fibronectin domain.

Competition experiments with anti-Axl hybridoma antibodies. We determined whether antibodies YW326.6 and YW327.42 could compete for human Axl binding with anti-Axl hybridoma antibodies 12A11 and 3G9 (Li, (2009), U.S. patent application No. 61/228,915 filed Jul. 27, 2009). In antibody competition binding experiments to human Axl, Antibody YW327.6 did not compete for human Axl binding with either of hybridoma antibodies 12A11 or 3G9, demonstrating that these antibodies do not recognize the same epitopes. Antibody YW327.42 competed for human Axl binding with hybridoma antibody 12A11, but did not compete for human Axl binding with hybridoma antibody 3G9.

YW327.6S2 Down Regulates Axl Expression, Inhibits its Activation, Signaling and Gas6-Dependent Baf3Axl Cell Proliferation.

Figure 7F:
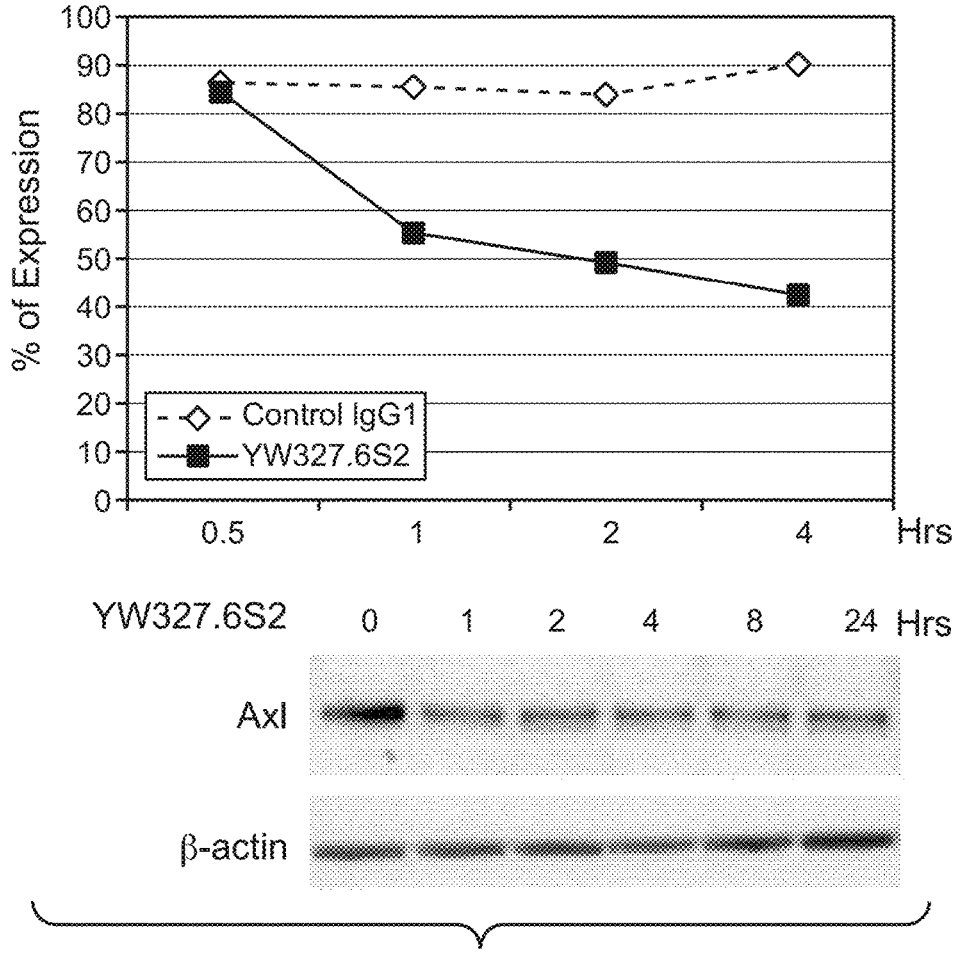
Figure 7G:
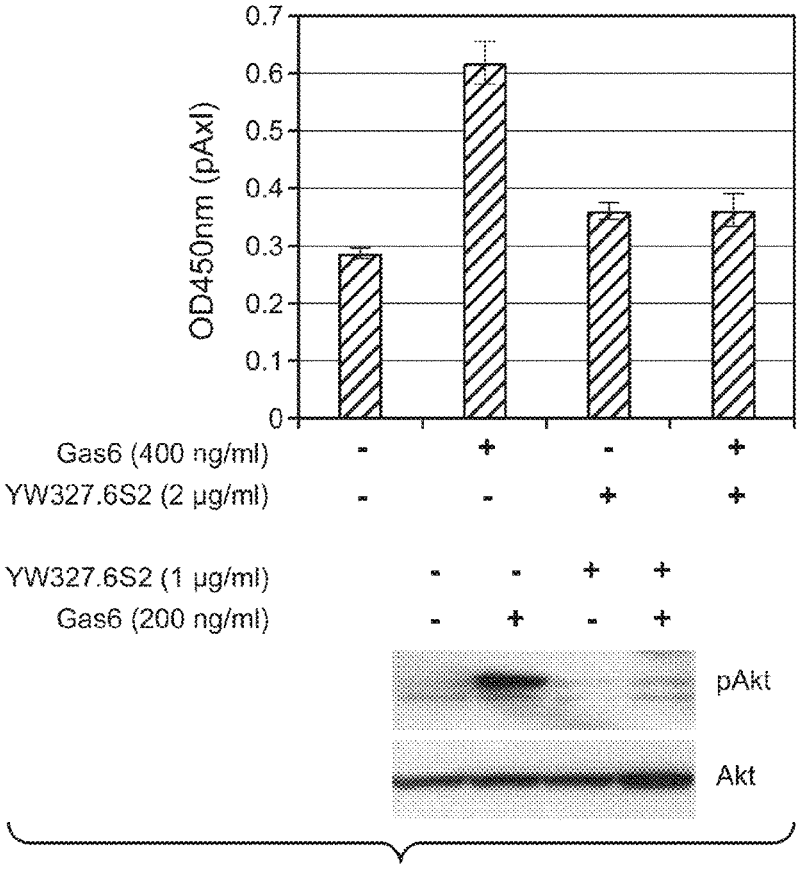
Figure 7H:
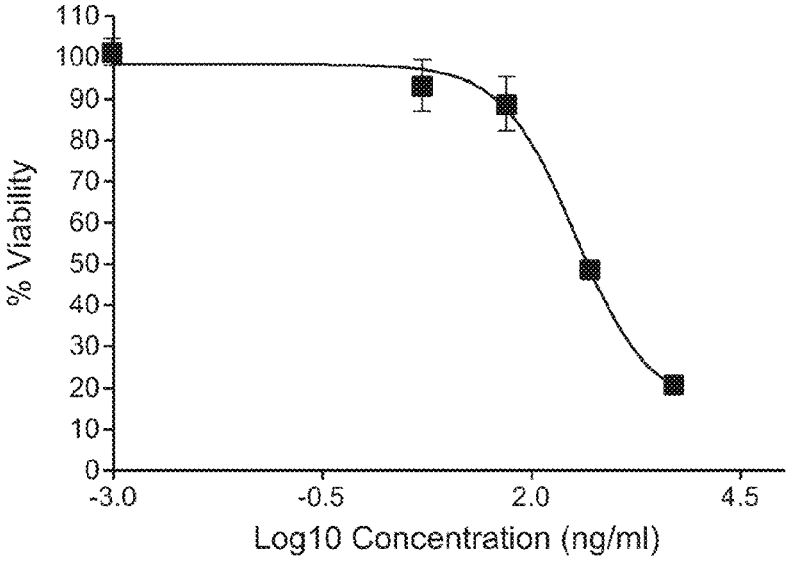

To test whether YW327.6S2 affects Axl biological functions, we first evaluated its effect on Axl expression and signaling. Treatment of NSCLC cell line A549 with YW327.6S2 resulted in rapid down-regulation of Axl expression on cell surface (FIG. 7F, upper panel) and this down regulation is sustained for 24 hrs (FIG. 7F, lower panel). Gas6 treatment of H1299 NSCLC cells induces Axl phosphorylation that was inhibited when cells were pre-incubated with YW327.6S2 (FIG. 7G, upper panel). Consequently, pre-incubation of H1299 cells with YW327.6S2 blocks Gas6-induced phosphorylation of the down-stream signaling molecule Akt (FIG. 7G, lower panel). Down-regulation of Axl expression and inactivation of its signaling by YW327.6S2 potently inhibited Gas6-dependent growth of Baf3Axl cells, with an IC50 of 340 ng/ml (FIG. 7H).

YW327.6S2 Reduces A549 Xenograft Growth and Enhances the Effect of Anti-VEGF.

In a previous study, we showed that inhibition of Axl by either RNAi or treatment with anti-human Axl hybridoma monoclonal antibodies significantly attenuated A549 NSCLC tumor growth (Li et al, 2009). We therefore first tested the effect of YW327.6S2 on tumor growth in this model. YW327.6S2 alone at 10 mg/kg, twice a week dosing regimen significantly reduced A549 tumor growth (FIG. 8A), and this inhibitory effect is comparable to that of anti-human Axl hybridoma antibodies (FIG. 8C).

Figure 8A:
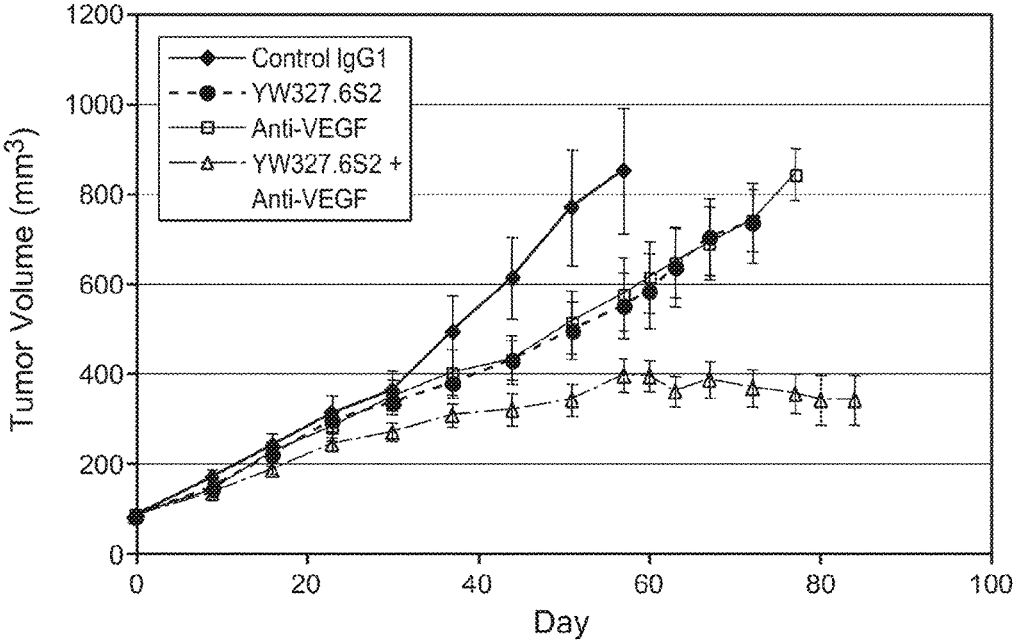

Axl is expressed on endothelial cells and enhances VEGF-induced endothelial tubule formation (Li et al, 2009; Holland et al, 2005); we tested whether anti-Axl mAb could enhance the anti-tumor growth property of anti-VEGF (Liang et al, 2006). Anti-VEGF antibody alone and YW327.6S2 alone had similar effects on A549 tumor growth (FIG. 8A). Combination of the two antibodies together resulted in enhanced tumor growth inhibition compared with either antibody alone, with 30% inhibition by single agent versus 60% inhibition by the combination treatment (FIG. 8A).

Figure 8B:
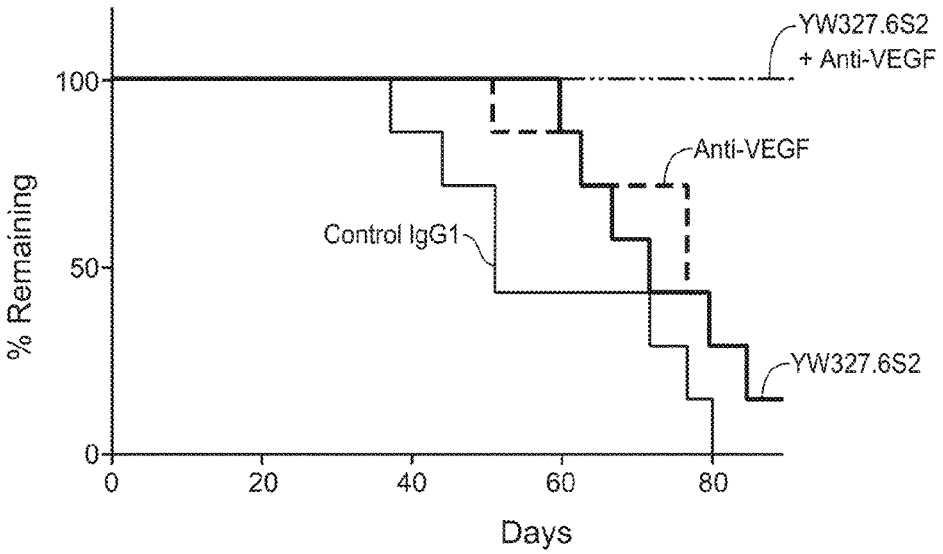

Animals in this study were dosed twice weekly for 60 days and followed to day 85 to examine the delay in tumor growth (animals were removed from the study when tumor sizes exceeded 800 $mm^3$; no animals were removed as a result of toxicity). YW327.6S2 in combination with anti-VEGF significantly delayed tumor growth as compared to a single agent (FIG. 8A). There was no tumor re-growth in the combination treatment group during the time elapsed from the last dose to the end of the experiment (day 85), which lead to the survival of all the animals in this group at the end of the experiment as shown in the Kaplan-Meier plot (FIG. 8B).

Figure 8C:
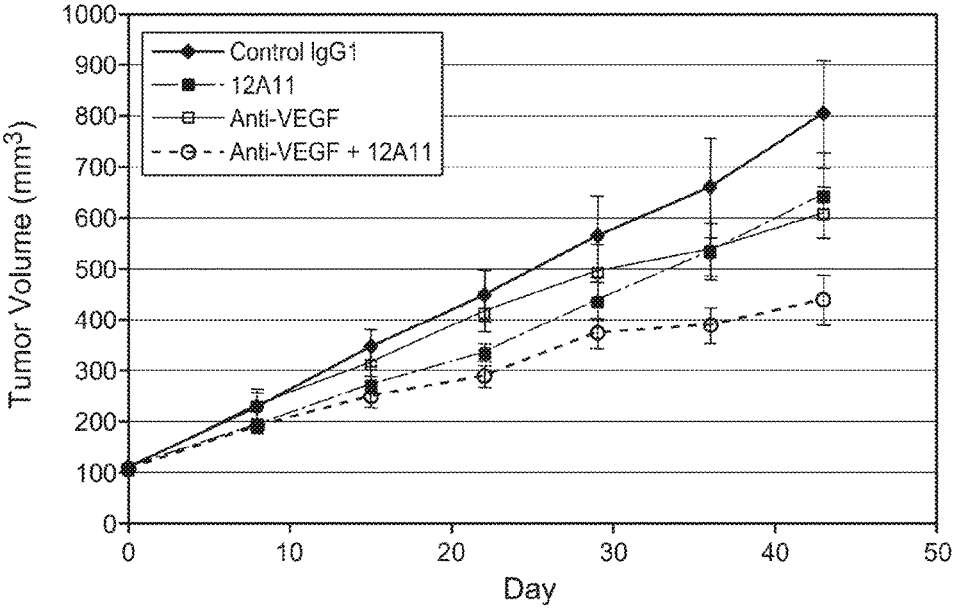
Figure 8D:
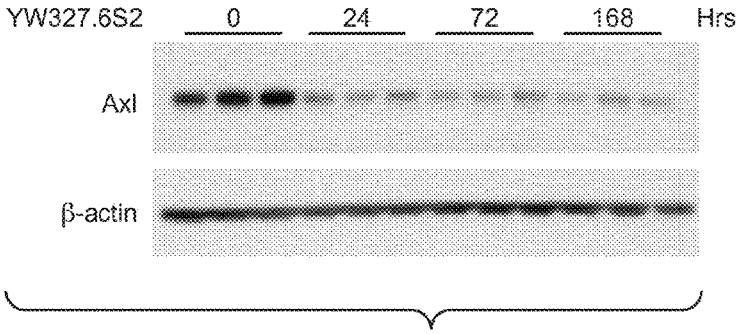
Figure 8E:
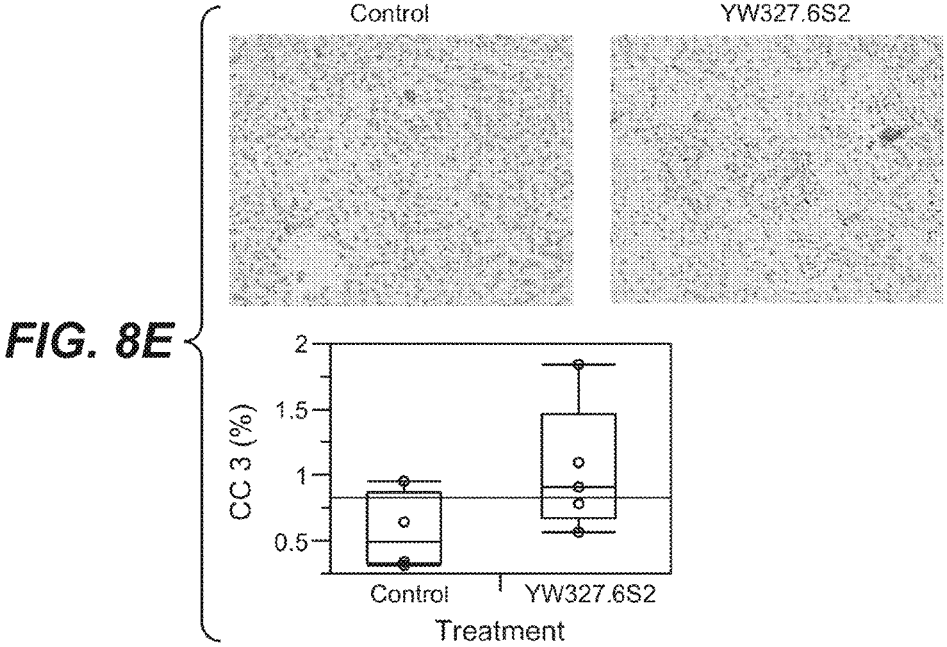

The anti-human Axl hybridoma monoclonal antibody 12A11, which does not cross-react with murine Axl, significantly attenuated A549 xenograft tumor growth (Li et al, 2009), it also enhances the effect of anti-VEGF as shown in FIG. 8C. This is expected, since 12A11 directly inhibits tumor cell growth and anti-VEGF affects tumor vasculature.

YW327.6S2 Down-Regulates Receptor Expression and Induces Apoptosis of A549 Tumor Cells.

To begin to understand the mechanisms that mediate YW327.6S2 effect on reducing tumor growth, we performed a pharmacodynamic study. A549 tumor bearing mice was treated with YW327.6S2, and tumors were excised at 0, 24, 72, and 168 hrs post dosing. Western blotting analysis of tumor lysates showed that Axl expression was down-regulated 24 hr after antibody administration and sustained over 168 hrs (FIG. 8D), suggesting that the anti-tumor growth effect of YW327.6S2 is mediated in part by down regulation of Axl expression.

To determine whether YW327.6S2 has direct effect on tumor cell proliferation and apoptosis, A549 xenograft tumors treated with control or YW327.6S2 for two weeks were excised and cleaved caspase 3 (CC3) and Ki67 IHC were performed. Tumors treated with YW327.6S2 exhibited increased CC3 compared with the control (FIG. 8E), suggesting that YW327.6S2 induces apoptosis of tumor cells. There was no significant difference in Ki67 positive nuclei between control and YW327.6S2 treated tumors, suggesting that YW327.6S2 does not directly affect tumor cell proliferation.

Figure 8F:
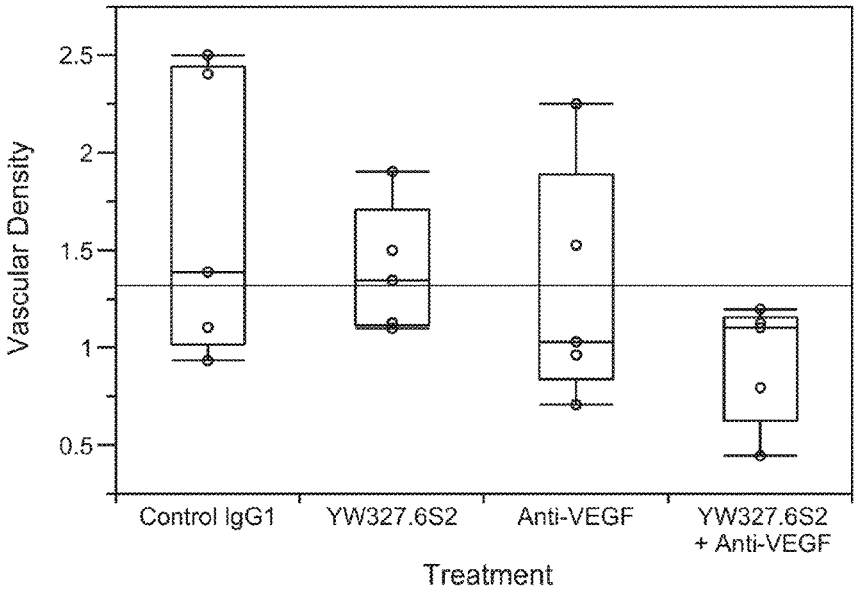

To investigate whether YW327.6S2 affects tumor-associated vasculature, we treated A549 tumor bearing mice with YW327.6S2 alone or in combination with anti-VEGF. Tumors were excised and stained with MECA32, a pan endothelial marker, to examine the intratumoral vascular density. YW327.6S2 alone did not significantly reduced vascular density compared with control but combination with anti-VEGF resulted in significant decrease of the tumor associated vascular density (FIG. 8F). In contrast, 12A11 has no significant effect on intratumoral vascular density by itself or in combination with anti-VEGF.

YW327.6S2 Enhances the Effect of Erlotinib and Chemotherapy.

To test whether YW327.6S2 could enhance the therapeutic index of standard care for NSCLC, we performed combination treatment of YW327.6S2 with EGFR small molecule inhibitor (SMI) erlotinib and chemotherapy.

A549 contains wild type EGFR and is only moderately sensitive to erlotinib (Yauch et al, 2005); we therefore investigated whether anti-Axl mAb can sensitize these cells to EGFR SMI. YW327.6S2 and erlotinib when administrated as a single agent resulted in 30% reduction in tumor growth but in combination reduced the tumor growth rate by more than 50% (FIG. 9A), suggesting that anti-Axl mAb enhances the anti-tumor growth effect of erlotinib.

We then investigated whether anti-Axl mAb was able to enhance the therapeutic index of standard chemotherapy for NSCLC. Mice bearing A549 xenografts were treated with one cycle of chemotherapy consisting paclitaxel (6.25 mg/kg/day, 5 days) and carboplatin (100 mg/kg, one dose) administrated at the beginning of the treatment (day 0, FIG. 9B). Chemotherapy alone has similar effect on tumor growth as YW327.6S2 administrated alone, and combination of the two resulted in enhanced inhibition of tumor growth (FIG. 9B).

YW327.6S2 Reduces Vascular Density and Inhibits Inflammatory Cytokine Secretion from Tumor-Associated Macrophages in MDA-MB-231 Breast Cancer Xenograft Model.

Figure 10A:
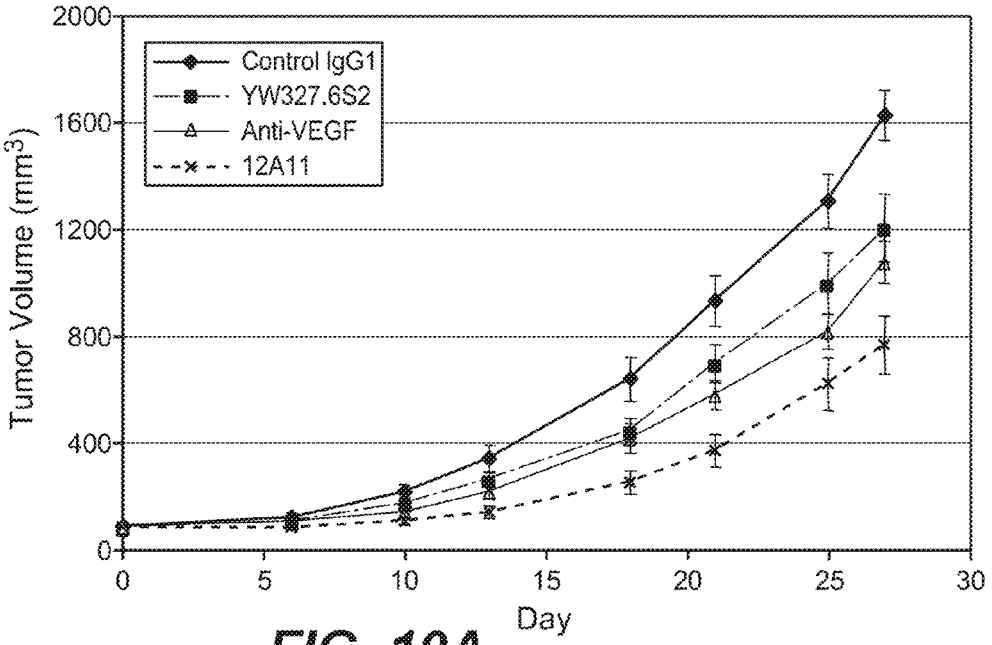
Figure 10B:
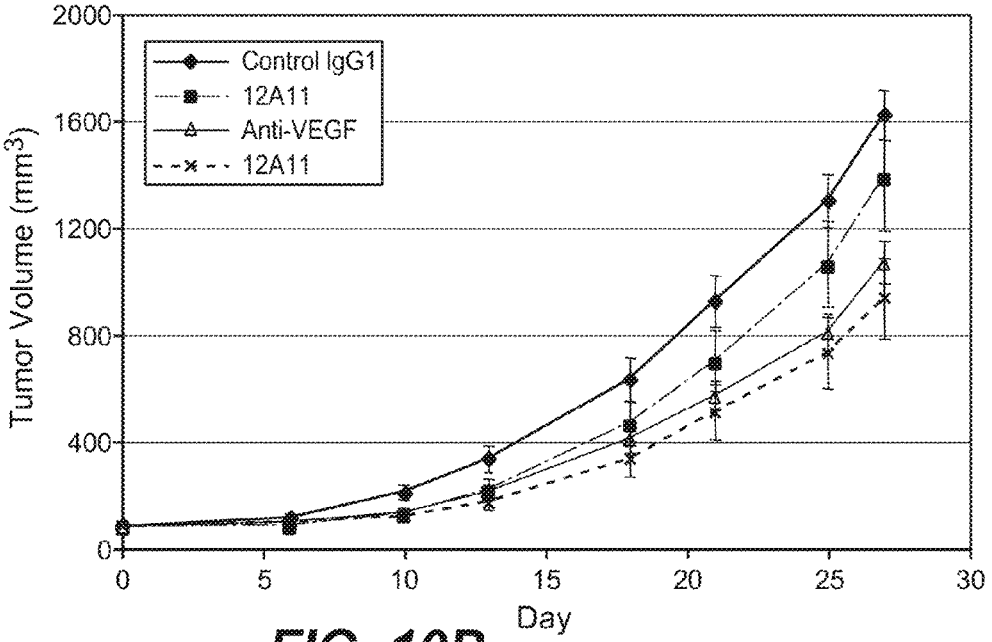
Figure 10C:
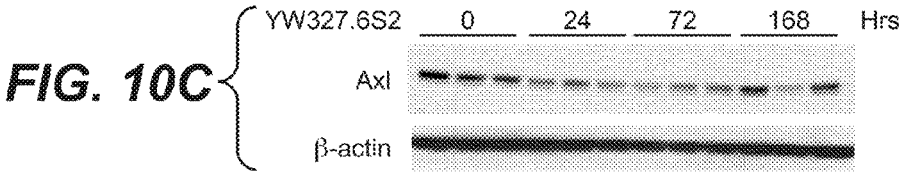
Figure 10D:
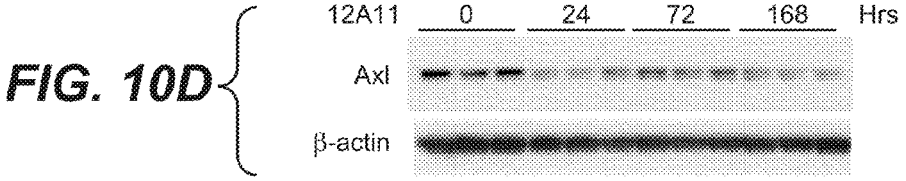

Since Axl knockdown by shRNA has only moderate effect on MDA-MB-231 xenograft tumor growth (Li et al, 2009), we asked whether YW327.6S2 is efficacious in this model. YW327.6S2 alone was able to reduce tumor growth (25%), and had similar effect to anti-VEGF used as a single agent in this model (FIG. 10A). The combination therapy leads to a 50% reduction in tumor growth, suggesting that YW327.6S2 potentiates the effect of anti-VEGF (FIG. 10A). In contrast, the anti-Axl hybridoma antibody 12A11 (Li et al, 2009) which does not cross-react with murine Axl, has no significant effect on tumor growth as a single agent in this model, nor does affects anti-VEGF (FIG. 10B). Western blot analysis showed that both YW327.6S2 and 12A11 down-regulate Axl expression in tumors (FIGS. 10C & D). These results suggest that the anti-tumor growth effect of YW327.6S2 might be mediated by modulation of tumor stromal functions.

Figure 10E:
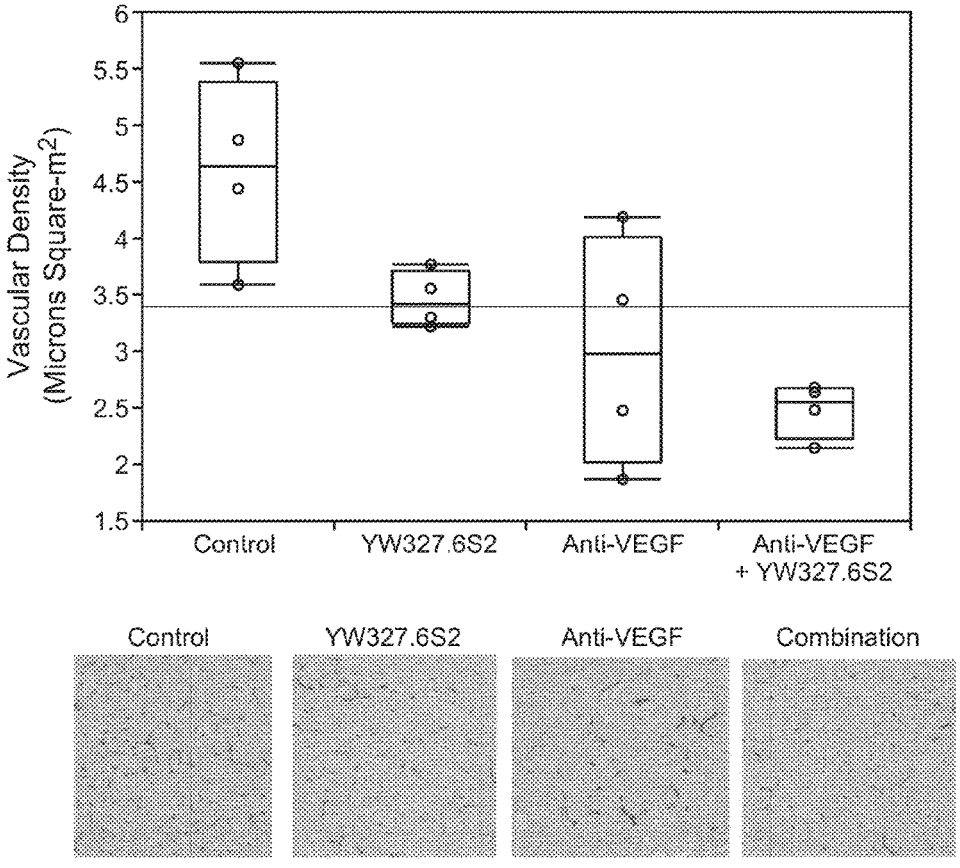

To investigate further how YW327.6S2 might modulate tumor stromal functions, we treated MDA-MB-231 tumor bearing mice with YW327.6S2 alone or in combination with anti-VEGF. At various time points after administration of the antibodies, tumors were excised and stained with MECA32 to examine the intra-tumoral vascular density. Both YW327.6S2 and anti-VEGF significantly reduced vascular density compared with control (FIG. 10E). And combination of the two antibodies resulted in further reduction of the tumor associated vascular density. These results suggest that YW327.6S2 reduces MDA-MB-231 tumor growth in part by altering vascular functions.

Figure 10F:
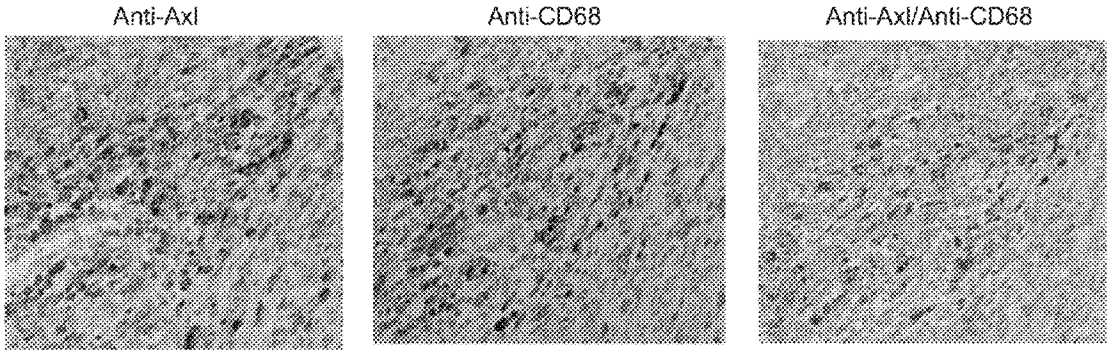
Figure 10G:
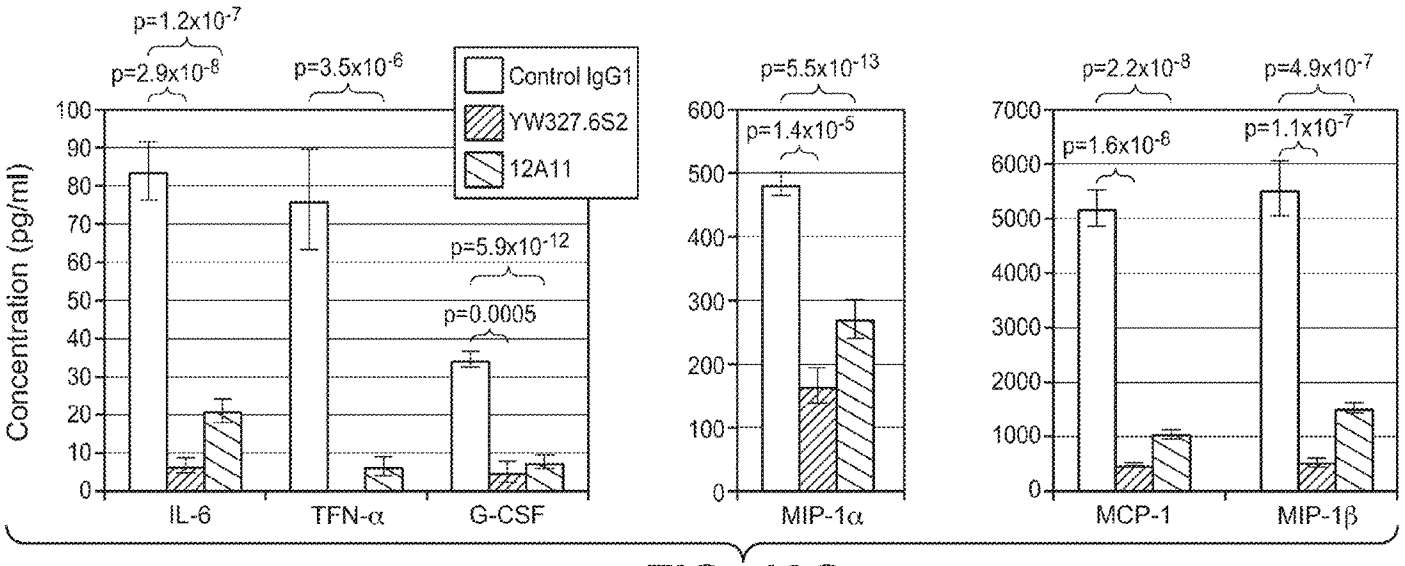

In primary human breast cancer specimens, we found that Axl protein is strongly expressed in infiltrating macrophages (FIG. 10F) and therefore asked whether Axl mAb YW327.6S2 might affect tumor associate macrophages (TAMs) functions. MDA-MB-231 xenograft tumors were treated for one week with YW327.6S2, 12A11 or control antibody, and TAMs were isolated by sorting for F4/80 positive cells. Cells were cultured in serum free media overnight, and the supernatant was collected and assayed for the presence of various cytokines and chemokines. TAMs from tumors treated with YW327.6S2 and 12A11 produced much lower levels of inflammatory cytokines and chemokines compared with TAMs treated with control antibody (FIG. 10G). Treatment with either Axl-mAb does not affect Axl expression levels on TAMs (data not shown) in contrast to down-regulation of Axl expression on tumor cells by theses antibodies (FIGS. 10C & D). These results suggest that Axl mAbs most likely modulate inflammatory cytokine/chemokine secretion from TAMs in an indirect manner, perhaps by blocking the crosstalk between tumor and stromal cells.

YW327.6S2 Reduces MDA-MB-231 Breast Cancer Cells Metastasis to the Bone.

In a previous study we showed that Axl knockdown by shRNA inhibits metastasis of MDA-MB-231 breast cancer cells to the lung in an orthotopic model (Li et al, 2009), we therefore tested whether YW327.6S2 affects metastasis of these cells. MDA-MB-231 cells stably expressing the luciferase reporter gene (20) were injected via tail vein into SCID mice. Four weeks after injection, strong luminescent signals were detected at craniofacial region, tibia and femur of all five animals in the control antibody treated group. The sites detected by bioluminescence in control groups are 5, 5, 4, 3 and 1 in each animal, with a total of 18 (FIG. 11A). In mice treated with YW327.6S2, the sites detected by bioluminescence were significantly reduced, with 0, 1, 2, 3, and 1 sites in each animal and a total of 7 for the entire group (FIG. 11A). The presence of metastatic foci in bone was verified by histological analysis (FIG. 11B). These results suggest that YW327.6S2 is able to reduce MDA-MB-231 breast cancer cells metastasis to distant organs.

Discussion

We have developed and characterized a human anti-Axl monoclonal antibody (YW327.6S2) that exhibits cross-species reactivity and blocks various functions of Axl in tumorigenesis. Besides being the first reported fully humanized blocking antibody for Axl, YW327.6S2 not only serves as a powerful tool to dissect out the impact of Axl activation/signaling in multiple aspects of cancer development and progression, but also represents a potential therapeutic for treatment of various cancers.

Our results show that YW327.6S2 blocks Axl functions by down-regulation of Axl expression as well as inhibition of ligand Gas6 binding to the receptor, leading to inactivation of Axl and its down-stream signaling (FIG. 7). The ability of YW327.6S2 to down-regulate Axl expression in cancer cells represents an important mechanism for its inhibitory effects, since many cancers express constitutively activated Axl and are no longer responsive to exogenous Gas6 (Li et al, 2009).

In the A549 NSCLC model, YW327.6S2 significantly attenuated tumor growth when administrated as a single agent (FIG. 8A). This inhibitory effect is comparable to that of anti-Axl hybridoma antibodies in this model (Li et al (2009); FIG. 8C). YW327.6S2 rapidly down-regulates Axl expression in xenografts (FIG. 8D), and induces apoptosis of tumor cells (FIG. 8E), which is likely one of the mechanisms that mediates its inhibitory effect on tumor growth. Our previous findings that Axl modulates endothelial cell functions by regulating the DKK3 and angiopoietin/Tie2 pathways (Li et al, 2009) raised the possibility that anti-Axl mAb could enhance the effect of anti-VEGF in reducing tumor growth. Our results (FIGS. 8A & F) are consistent with this hypothesis, in that YW327.6S2 impacts tumor vasculature by enhancing the effect of anti-VEGF to reduce intra-tumoral vascular density. Indeed, co-administration of YW327.6S2 and anti-VEGF in A549 model resulted in tumor stasis that was maintained for at least 4 weeks after treatment cessation (FIG. 8B). The hybridoma antibody 12A11 also enhances the anti-tumor effect of anti-VEGF in this model (FIG. 8C). However, unlike YW327.6S2, 12A11 does not have direct effect on tumor vasculature; rather it directly inhibits tumor cell proliferation and induces apoptosis (Li et al. 2009). The effect of 12A11 on tumor growth and the anti-VEGF on tumor vasculature resulted in an increased effect when the two agents are used together.

EGFR small molecule inhibitors such as erlotinib are efficacious in treatment of NSCLC tumors that harbor EGFR mutations or amplification (Lynch et al, 2004; Paez et al, 2004; Eberhard et al, 2005; Giaccone et al, 2005; Tsao et al, 2005). It is also known that treatment of breast cancer cells with Her2/EGFR small molecules inhibitor Lapatinib or anti-Her2 antibody Herceptin leads to induction of Axl expression and consequently results in resistance of cancer cells to these therapies (Liu et al, 2009). We have found recently that Axl expression is induced in HCC827 NSCLC (a cell line that harbors both EGFR mutation and amplification) cells that have acquired resistance to erlotinib and Axl knockdown in resistant cells restores their sensitivity to erlotinib, suggesting that Axl may play a role in erlotinib resistance in NSCLC. Since A549 cells contains wild type EGFR and are only moderately sensitive to EGFR inhibition in vitro (Yauch et al, 2005), we asked whether anti-Axl mAb would sensitize these cells to erlotinib. Our results showed that YW327.6S2 potentiates the effect of erlotinib in reducing tumor growth (FIG. 9A), suggesting that anti-Axl mAb may enhance the efficacy of EGFR inhibitors in tumors that are refractory to EGFR inhibition alone, perhaps by directly reducing Axl expression in tumor cells.

Systemic chemotherapy plays the largest part in the treatment paradigms for NSCLC. For recurrent or advanced disease, patients treated with chemotherapy that consists of carboplatin/paclitaxel have a response rate of 15% and median survival of 10.3 months (Sandley et al, 2006). Our results in A549 NSCLC model showed that YW327.6S2 is able to enhance the anti-tumor efficacy of carboplatin/paclitaxel (FIG. 9B), suggesting blocking Axl functions might improve therapeutic index of chemotherapy in this disease. Our results are consistent with a recent report demonstrating an Axl small molecule inhibitor synergized with cisplatin to suppress liver micrometastasis in 4T1 breast cancer orthotopic model (Holland et al, 2010).

In the MDA-MB-231 breast cancer model, YW327.6S2 alone is able to significantly attenuate tumor growth (FIG. 10A). The anti-Axl hybridoma antibody, which does not cross react with murine Axl and therefore would only affect tumor cells, has no significant effect on tumor growth in this model (FIG. 10B). These results suggest that YW327.6S2 is likely to exert its anti-tumor effect through its actions on tumor stroma. Our results show that YW327.6S2 reduces intra-tumoral vascular density (FIG. 10E) and enhances the effect of anti-VEGF. Through its effect on tumor vasculature, YW327.6S2 may impact on tumor growth.

An association between the development of cancer and inflammation has long been appreciated (Balkwill & Mantovani, 2001; Coussens & Werb, 2002). The chronic inflammation associated with infection and irritation may lead to environments that foster genomic lesions and tumor initiation. There is increasing evidence that TAMs have causal roles in tumor progression including promotion of angiogenesis and matrix remodeling (Balkwill et al, 2005; Pollard, 2004). The signals responsible for this are thought to be inflammatory cytokines, including tumor necrosis factor-α (TNF-α), interleukin 6 (IL-6) and a plethora of chemokines. These cytokines and chemokines not only recruit immune cells to the specific sites that stimulate tumor progression, but it has been shown that their receptors are expressed on tumor cells where they can increase tumor growth and migration (Haghnegandar et al, 2000). In primary human breast cancer, Axl protein is expressed at high levels on tumor associated macrophages (TAMs) (FIG. 10F). We provide evidence here that anti-Axl mAbs could modulate the functions of these cells through an indirect mechanism. Our data showed that treatment of MDA-MB-231 xenografts with either YW327.6S2 or 12A11 (which does not cross react with murine Axl and therefore should not have direct effect on TAMs) inhibits secretion of inflammatory cytokines and chemokines from TAMs (FIG. 10G). Since Axl-mAbs do not seem to have significant effect on Axl expression on TAMs but down-regulate receptor expression on tumor cells, it is likely that anti-Axl-mAbs modulate cytokine/chemokine secretion from TAMs by blocking the crosstalk between tumor and stromal cells. These results are consistent with the recent reports that tumor cells could promote their growth by educating infiltrating leukocytes to induce expression of Gas6 (Loges et al, 2010); and a small molecule inhibitor of Axl reduced GM-CSF expression in 4T1 breast tumor cells (Holland et al, 2010).

Previous studies have established the role of Axl in promoting tumor cell migration, invasion and metastasis (Zhang et al, 2008; Li et al, 2009; Tai et al, 2008; Vajkoczy et al, 2006; Gjerdrum et al, 2010). Here we showed that YW327.6S2 is able to reduce metastasis of MDA-MB-231 breast cancer cells to the bone. These results are consistent with our previous data that Axl silencing by RNAi in breast cancer cells inhibits their metastasis to the lung in an orthotropic model (Li et al, 2009; Gjerdrum et al, 2010), suggesting that this anti-Axl antibody could have therapeutic potential not only in treatment of primary tumor but also in metastatic disease.

In conclusion, we have developed a human monoclonal antibody that blocks Axl functions. This anti-Axl mAb exerts its anti-tumor effect through multiple mechanisms including induction of tumor cell apoptosis, regulation of angiogenesis and modulation of tumor associated immune cells functions. Additionally, this anti-Axl mAb enhances the anti-tumor efficacy of anti-VEGF, EGFR SMI as well as chemotherapy, may therefore represent a novel therapeutic approach in clinical settings where these therapies are standard care.

PARTIAL REFERENCE LIST

Balkwill F, Mantovani A. Inflammation and cancer: back to Virchow? (2001). Lancet 357: 539-45.

Balkwill F, Charles K A, Mantovani A. (2005). Smoldering and polarized inflammation in the initiation and promotion of malignant disease. Cancer Cell 7: 211-7.

Berclaz G, Alternatt H J, Rohrbach V, Kieffer I, Dreher E, Andres A C. (2001). Estrogen dependent expression of the receptor tyrosine kinase axl in normal and malignant human breast. Ann Oncol 12: 819-24.

Brey E M, Lalani Z, Johnston C, Wong M, McIntire L V, Duke P J, Patrick Jr C W. (2003). Automated Selection of DAB-labeled Tissue for Immunohistochemical Quantification. J Histochem & Cytochem 51: 575-84.

Carter P, Presta L, Gorman C M, Ridgway J B, Henner D, Wong W L, Rowland A M, Kotts C, Carver M E, Shepard H M. (1992). Humanization of an anti-p185HER2 antibody for human cancer therapy. Proc Natl Acad Sci USA 89:4285-89.

Chung B I, Malkowicz S B, Nguyen T B, Libertino J A, McGarvey T W. (2003). Expression of the proto-oncogene Axl in renal cell carcinoma. DNA Cell Biol 22:533-40.

Coussens L M, Werb Z. (2002). Inflammation and cancer. Nature 420: 860-7.

Craven R J, Xu L H, Weiner T M, Fridell Y W, Dent G A, Srivastava S, Varnum B, Liu E T, Cance W G. (1995). Receptor tyrosine kinases expressed in metastatic colon cancer. Int J Cancer 60:791-7.

Eberhard D A, Johnson B E, Amler L C, et al. (2005). Mutations in the epidermal growth factor receptor and in KRAS are predictive and prognostic indicators in patients with non-small cell lung cancer treated with chemotherapy alone and in combination with erlotinib. J Clin Oncol 23: 5900-9.

Giaccone G. (2005). Epidermal growth factor receptor inhibitors in the treatment of non-small-cell lung cancer. J Clin Oncol 23: 3235-42.

Gjerdrum C, Tiron C, Hoiby T, Stefansson I, Haugen H, Sandal T, et al. (2010). Axl is an essential epithelial-to-mesenchymal transition-induced regulator of breast cancer metastasis and patient survival. Proc Natl Acad Sci USA 107: 1124-29.

Haghnegandar H, Du J, Wang D, Strieter R M, Burdick M D, Nanney L B, Cardwell N, Luan J, Shattuck-Brandt R, Richmond A. (2000). The tumorigenic and angiogenic effects of MGSA/GRO proteins in melanoma. J Leukoc Biol 67:53-62.

Holland S J, Powell M J, Franci C, Chan E W, Friera A M, Atchison R E, et al. (2005). Multiple roles for the receptor tyrosine kinase axl in tumor formation. Cancer Res 65: 9294-303.

Holland S J, Pan A, Franci C, Hu Y, Chang B, Li W, et al. (2010). R428, a selective small molecule inhibitor of Axl kinase, blocks tumor spread and prolongs survival in models of metastatic breast cancer. Cancer Res 70:1544-54.

Hong C C, Lay J D, Huang J S, Cheng A L, Tang J L, Lin M T, Lai G M, Chuang S E. (2008). Receptor tyrosine kinase AXL is induced by chemotherapy drugs and overexpression of AXL confers drug resistance in acute myeloid leukemia. Cancer Lett 268: 314-24.

Hutterer M, Knyazev P, Abate A, Reschke M, Maier H, Stefanova N, Knyazeva T, et al. (2008). Axl and growth arrest-specific gene 6 are frequently overexpressed in human gliomas and predict poor prognosis in patients with glioblastoma multiforme. Clin Cancer Res 14:130-8.

Ito T, Ito M, Naito S, Ohtsuru A, Nagayama Y, Kanematsu T, Yamashita S, Sekine I. (1999). Expression of the Axl receptor tyrosine kinase in human thyroid carcinoma. Thyroid 9: 563-7.

Janssen J W, Schulz A S, Steenvoorden A C, Schmidberger M, Strehl S, Ambros P F, Bartram C R. (1991). A novel putative tyrosine kinase receptor with oncogenic potential. Oncogene 6: 2113-20.

Koorstra J B, Karikari C A, Feldmann G, Bisht S, Rojas P L, Offerhaus G J, Alvarez H, Maitra A. (2009). The Axl receptor tyrosine kinase confers an adverse prognostic influence in pancreatic cancer and represents a new therapeutic target. Cancer Biol Ther 8: 618-26.

Lai C, Lemke G. (1991). An extended family of protein-tyrosine linase genes differentially expressed in the vertebrate nervous system. Neuron 6: 691-704.

Lee C V, Liang W C, Dennis M S, Eigenbrot C, Sidhu S S, Fuh G. (2004). High-affinity human antibodies from phage-displayed synthetic Fab libraries with a single framework scaffold. J Mol Biol 340:1073-93.

Li Y, Ye X, Tan C, Hongo J A, Zha J, Liu J, Kallop D, Ludlam M J, Pei L. (2009). Axl as a potential therapeutic target in cancer: role of Axl in tumor growth, metastasis and angiogenesis. Oncogene 28: 3442-55.

Lian W C, Wu X, Peale F V, Lee C V, Meng Y G, Gutierrez J, et al. (2006). Cross-speciess vascular endothelial growth factor (VEGF)-blocking antibodies completely inhibit the growth of human tumor xenografts and measure the contribution of stromal VEGF. J Biol Chem 281: 951-61.

Liang W C, Dennis M S, Stawicki S, Chanthery Y, Pan Q, Chen Y, Eigenbrot C, Yin J, Koch A W, Wu X, et al. (2007). Function blocking antibodies to neuropilin-1 generated from a designed human synthetic antibody phage library. J Mol Biol 366: 815-29.

Liu L, Greger J, Shi H, Liu Y, Greshock J, Annan R, Halsey W, Sathe G M, Martin A M, Gilmer T M. (2009). Novel mechanism of lapatinib resistance in HER2-positive breast tumor cells: activation of AXL. Cancer Res 69: 6871-8.

Loges S, Schmidt T, Tjwa M, van Geyte K, Lievens D, Lutgens E, et al. (2010). Malignant cells fuel tumor growth by educating infiltrating leukocytes to produce the mitogen Gas6. Blood 115:2264-73.

Lynch T J, Bell T W, Sordella R, et al. (2004). Activating mutations in the epidermal growth factor receptor underlying responsiveness of non-small-cell lung cancer to gefitinib. N Engl J Med 350:2129-39.

Mahadevan D, Cooke L, Riley C, Swart R, Simons B, Della Croce K, Wisner L, Iorio M, Shakalya K, Garewal H, Nagle R, Bearss D. (2007). A novel tyrosine kinase switch is a mechanism of imatinib resistance in gastrointestinal stromal tumors. Oncogene 26: 3909-19.

Meric F, Lee W P, Sahin A, Zhang H, Kung H J, Hung M C. (2002). Expression profile of tyrosine kinases in breast cancer. Clin Cancer Res 8:361-7.

O'Bryan J P, Frye R A, Cogswell P C, Neubauer A, Kitch B, Prokop C, et al, (1991). Axl, a transforming gene isolated from primary human myeloid leukemia cells, encodes a novel receptor tyrosine kinase. Mol Cell Biol 11:5016-31.

Paez J G, Janne P A, Lee J C, et al. (2004). EGFR mutations in lung cancer: correlation with clinical response to gefitinib therapy. Science 304: 1497-500.

Pollard J W. (2004). Tumour-educated macrophages promote tumour progression and metastasis. Nat Rev Cancer 4:71-8.

Rikova K, Guo A, Zeng Q, Possemato A, Yu J, Haack H, et al. (2007). Global survey of phosphotyrosine signaling identifies oncogenic kinases in lung cancer. Cell 131: 1190-203.

Sainaghi P P, Castello L, Bergamasco L, Galletti M, Bellosta P, Avanzi G C. (2005). Gas6 induces proliferation in prostate carcinoma cell lines expressing the Axl receptor. J Cell Physiol 204:36-44.

Sandley A, Gray R, Perry M C et al. (2006). Palitaxel-carboplatin alone or with bevacizumab for no-small cell lung cancer. N Engl J Med 355: 2542-50.

Shieh Y S, Lai C Y, Kao Y R, Shiah S G, Chu Y W, Lee H S, Wu C W. (2005). Expression of axl in lung adenocarcinoma and correlation with tumor progression. Neoplasia 7:1058-64.

Sidhu S S, Li B, Chen Y, Fellouse F A, Eigenbrot C, Fuh G. (2004). Phage-displayed antibody libraries of synthetic heavy chain complementarity determining regions. J Mol Biol 338:299-310.

Sun W, Fujimoto J, Tamaya T. (2004). Coexpression of Gas6/Axl in human ovarian cancers. Oncology 66:450-7.

Tai K Y, Shieh Y S, Lee C S, Shiah S G, Wu C W. (2008). Axl promotes cell invasion by inducing MMP-9 activity through activation of NF-kappaB and Brg-1. Oncogene 27: 4044-55.

Tsao M S, Sakurada A, Lorimer I, et al. (2005). Molecular analysis of the epidermal growth factor receptor (EGFR) gene and protein expression in patients treated with erlotinib in National Cancer Institute of Canada Clinical Trials Group (NCIC CTG) trial BR.21. J Clin Oncol 23: 7007. Meeting Abstracts.

Vajkoczy P, Knyazev P, Kunkel A, Capelle H H, Behrndt S, von Tengg-Kobligk H, et al. (2006). Dominant-negative inhibition of the Axl receptor tyrosine kinase suppresses brain tumor cell growth and invasion and prolongs survival. Proc Natl Acad Sci USA 103:5799-5804.

Wu C W, Li A F, Chi C W, Lai C H, Huang C L, Lo S S, Lui W Y, Lin W C. (2002). Clinical significance of AXL kinase family in gastric cancer. Anticancer Res 22:1071-8.

Yauch R L, Januario T, Eberhard D A, Cavet G, Zhu W, Fu L, et al. (2005). Epithelial versus mesenchymal phenotype determines in vitro sensitivity and predicts clinical activity of erlotinib in lung cancer patients. Clin Cancer Res 11:8686-98.

Zhang Y X, Knyazev P G, Cheburkin Y V, Sharma K, Knyazev Y P, Orfi L, et al. (2008). AXL is a potential target for therapeutic intervention in breast cancer progression. Cancer Res 68:1905-15.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

SEQUENCE LISTING

```
<160> NUMBER OF SEQ ID NOS: 166

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Phe Thr Phe Thr Gly His Trp Ile His
1               5                   10


<210> SEQ ID NO 2
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Trp Ile Ser Pro Tyr Gly Gly Ser Thr Tyr Tyr Ala Asp Ser Val
1               5                   10                  15

Lys Gly


<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Arg Glu Tyr Ser Gly Trp Gly Gly Ser Ser Val Gly Tyr Ala Met
1               5                   10                  15

Asp Tyr


<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
```

peptide

<400> SEQUENCE: 4

Arg Ala Ser Gln Asp Val Ser Thr Ala Val Ala
1 5 10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 5

Ser Ala Ser Phe Leu Tyr Ser
1 5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 6

Gln Gln Ser Tyr Thr Thr Pro Pro Thr
1 5

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 7

Gly Phe Ser Leu Ser Gly Ser Trp Ile His
1 5 10

<210> SEQ ID NO 8
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 8

Gly Trp Ile Asn Pro Tyr Arg Gly Tyr Ala Tyr Tyr Ala Asp Ser Val
1 5 10 15

Lys Gly

<210> SEQ ID NO 9
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 9

Ala Arg Glu Tyr Ser Gly Trp Gly Gly Ser Ser Val Gly Tyr Ala Met
1 5 10 15

Asp Tyr

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 10

Arg Ala Ser Gln Asp Val Ser Thr Ala Val Ala
1 5 10

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 11

Ser Ala Ser Phe Leu Tyr Ser
1 5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 12

Gln Gln Ser Tyr Thr Thr Pro Pro Thr
1 5

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 13

Gly Phe Ser Phe Thr Gly Thr Trp Ile His
1 5 10

<210> SEQ ID NO 14
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 14

Gly Trp Ile Ala Pro Tyr Ser Arg His Pro Tyr Tyr Ala Asp Ser Val
1 5 10 15

Lys Gly

<210> SEQ ID NO 15
<211> LENGTH: 18
<212> TYPE: PRT
<213> ORGANISM: Artificial Sequence <220> FEATURE:
<223> OTHER INFORMATION: Description of Artificial Sequence: Synthetic
peptide

<400> SEQUENCE: 15

Ala Arg Glu Tyr Ser Gly Trp Gly Gly Ser Ser Val Gly Tyr Ala Met
1 5 10 15

Asp Tyr

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 16

Arg Ala Ser Gln Asp Val Ser Thr Ala Val Ala
1 5 10

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 17

Ser Ala Ser Phe Leu Tyr Ser
1 5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 18

Gln Gln Ser Tyr Thr Thr Pro Pro Thr
1 5

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 19

Gly Phe Thr Phe Thr Gly Ser Trp Ile His
1 5 10

<210> SEQ ID NO 20
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 20

Gly Trp Ile Ser Pro Tyr Gly Gly Ser Thr Tyr Tyr Ala Asp Ser Val 1 5 10 15

Lys Gly

<210> SEQ ID NO 21
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 21

Ala Arg Glu Tyr Asn Asp Trp Arg Gly Ser Ser Val Gly Tyr Ala Met
1 5 10 15

Asp Tyr

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 22

Arg Ala Ser Gln Asp Val Ser Thr Ala Val Ala
1 5 10

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 23

Ser Ala Ser Phe Leu Tyr Ser
1 5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 24

Gln Gln Ser Tyr Ser Asn Pro Tyr Thr
1 5

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 25

Gly Phe Thr Phe Thr Gly Ser Trp Ile His
1 5 10

<210> SEQ ID NO 26
<211> LENGTH: 18

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 26

Gly Trp Ile Ser Pro Tyr Gly Gly Ser Thr Tyr Tyr Ala Asp Ser Val
1 5 10 15

Lys Gly

<210> SEQ ID NO 27
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 27

Ala Arg Glu Tyr Ser Gly Trp Ala Ser Ser Tyr Val Gly Tyr Ala Met
1 5 10 15

Asp Tyr

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 28

Arg Ala Ser Gln Asp Val Ser Thr Ala Val Ala
1 5 10

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 29

Ser Ala Ser Phe Leu Tyr Ser
1 5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 30

Gln Gln Ser Tyr Thr Ser Pro Ser Thr
1 5

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 31

Gly Phe Thr Phe Thr Gly Ser Trp Ile His
1 5 10

<210> SEQ ID NO 32
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 32

Gly Trp Ile Ser Pro Tyr Gly Gly Ser Thr Tyr Tyr Ala Asp Ser Val
1 5 10 15

Lys Gly

<210> SEQ ID NO 33
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 33

Ala Arg Glu Tyr Pro Gly Trp Gly Gly Ser Ser Ile Gly Tyr Glu Met
1 5 10 15

Asp Tyr

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 34

Arg Ala Ser Gln Asp Val Ser Thr Ala Val Ala
1 5 10

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 35

Ser Ala Ser Phe Leu Tyr Ser
1 5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 36

Gln Gln Ser Tyr Tyr Phe Arg Ser Thr
1 5

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 37

Gly Phe Thr Phe Thr Gly Thr Gly Ile His
1 5 10

<210> SEQ ID NO 38
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 38

Ala Gly Ile Ser Pro Ala Gly Gly Tyr Thr Tyr Tyr Ala Asp Ser Val
1 5 10 15

Lys Gly

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 39

Ala Arg Trp Arg Ser Leu Ser Ser Gly Met Asp Tyr
1 5 10

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 40

Arg Ala Ser Gln Asp Val Ser Thr Ala Val Ala
1 5 10

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 41

Ser Ala Ser Phe Leu Tyr Ser
1 5

<210> SEQ ID NO 42
<211> LENGTH: 9
<212> TYPE: PRT
<213> ORGANISM: Artificial Sequence
<220> FEATURE:

<223> OTHER INFORMATION: Description of Artificial Sequence: Synthetic
peptide

<400> SEQUENCE: 42

Gln Gln Ser Tyr Thr Thr Pro Pro Thr
1 5

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 43

Gly Phe Thr Phe Thr Gly Thr Gly Ile His
1 5 10

<210> SEQ ID NO 44
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 44

Ala Gly Ile Pro Pro Val Gly Ser Tyr Thr Tyr Tyr Ala Asp Ser Val
1 5 10 15

Lys Gly

<210> SEQ ID NO 45
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 45

Ala Arg Trp Arg Ser Leu Ser Ser Gly Met Asp Tyr
1 5 10

<210> SEQ ID NO 46
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 46

Arg Ala Ser Gln Asp Val Ser Thr Ala Val Ala
1 5 10

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 47

Ser Ala Ser Phe Leu Tyr Ser
1 5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 48

Gln Gln Ser Lys Thr Thr Pro Pro Thr
1 5

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 49

Gly Phe Ser Phe Thr Ser Ile Gly Ile His
1 5 10

<210> SEQ ID NO 50
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 50

Ala Gly Ile Pro Pro Val Gly Arg Tyr Thr Tyr Tyr Ala Asp Ser Val
1 5 10 15

Lys Gly

<210> SEQ ID NO 51
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 51

Ala Arg Trp Arg Ser Leu Ser Ser Gly Met Asp Tyr
1 5 10

<210> SEQ ID NO 52
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 52

Arg Ala Ser Gln Asp Val Ser Thr Ala Val Ala
1 5 10

<210> SEQ ID NO 53
<211> LENGTH: 7
<212> TYPE: PRT
<213> ORGANISM: Artificial Sequence
<220> FEATURE:

<223> OTHER INFORMATION: Description of Artificial Sequence: Synthetic
peptide

<400> SEQUENCE: 53

Ser Ala Ser Phe Leu Tyr Ser
1 5

<210> SEQ ID NO 54
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 54

Gln Gln Ser Tyr Met Ser Pro Leu Thr
1 5

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 55

Gly Phe Thr Phe Thr Gly Thr Gly Ile His
1 5 10

<210> SEQ ID NO 56
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 56

Ala Gly Ile Ser Pro Ala Gly Gly Tyr Thr Tyr Tyr Ala Asp Ser Val
1 5 10 15

Lys Gly

<210> SEQ ID NO 57
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 57

Ala Arg Trp Arg Ser Leu Ser Ser Gly Met Asp Tyr
1 5 10

<210> SEQ ID NO 58
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 58

Arg Ala Ser Gln Asp Val Ser Thr Ala Val Ala
1 5 10

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 59

Ser Ala Ser Phe Leu Tyr Ser
1 5

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 60

Gln Gln Ser Lys Arg Thr Pro Pro Thr
1 5

<210> SEQ ID NO 61
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 61

Gly Phe Ser Val Arg Gly Thr Gly Leu His
1 5 10

<210> SEQ ID NO 62
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 62

Ala Gly Ile Ser Pro Val Gly Gly Tyr Thr Tyr Tyr Ala Asp Ser Val
1 5 10 15

Lys Gly

<210> SEQ ID NO 63
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 63

Ala Arg Trp Arg Ser Leu Ser Ser Gly Met Asp Tyr
1 5 10

<210> SEQ ID NO 64
<211> LENGTH: 11
<212> TYPE: PRT
<213> ORGANISM: Artificial Sequence
<220> FEATURE:

<223> OTHER INFORMATION: Description of Artificial Sequence: Synthetic
peptide

<400> SEQUENCE: 64

Arg Ala Ser Gln Asp Val Ser Thr Ala Val Ala
1 5 10

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 65

Ser Ala Ser Phe Leu Tyr Ser
1 5

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 66

Gln Gln Ala Lys Thr Thr Pro Pro Thr
1 5

<210> SEQ ID NO 67
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 67

Gly Phe Thr Phe Thr Gly Thr Gly Ile His
1 5 10

<210> SEQ ID NO 68
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 68

Ala Gly Ile Ser Pro Ala Gly Gly Tyr Thr Tyr Tyr Ala Asp Ser Val
1 5 10 15

Lys Gly

<210> SEQ ID NO 69
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 69

Ala Arg Trp Arg Ser Leu Ser Ser Gly Met Asp Tyr
1 5 10

<210> SEQ ID NO 70
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 70

Arg Ala Ser Gln Asp Val Ser Thr Ala Val Ala
1 5 10

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 71

Ser Ala Ser Phe Leu Tyr Ser
1 5

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 72

Gln Gln Ala Lys Ser Thr Pro Pro Thr
1 5

<210> SEQ ID NO 73
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 73

Gly Phe Thr Phe Thr Gly Thr Gly Ile His
1 5 10

<210> SEQ ID NO 74
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 74

Ala Gly Ile Ser Pro Ala Gly Gly Tyr Thr Tyr Tyr Ala Asp Ser Val
1 5 10 15

Lys Gly

<210> SEQ ID NO 75
<211> LENGTH: 12
<212> TYPE: PRT
<213> ORGANISM: Artificial Sequence
<220> FEATURE:

<223> OTHER INFORMATION: Description of Artificial Sequence: Synthetic
peptide

<400> SEQUENCE: 75

Ala Arg Trp Arg Ser Leu Ser Ser Gly Met Asp Tyr
1 5 10

<210> SEQ ID NO 76
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 76

Arg Ala Ser Gln Asp Val Ser Thr Ala Val Ala
1 5 10

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 77

Ser Ala Ser Phe Leu Tyr Ser
1 5

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 78

Gln Gln Ala Lys Arg Thr Pro Pro Thr
1 5

<210> SEQ ID NO 79
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 79

Gly Phe Thr Phe Thr Gly Thr Gly Ile His
1 5 10

<210> SEQ ID NO 80
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 80

Ala Gly Ile Ser Pro Ala Gly Gly Tyr Thr Tyr Tyr Ala Asp Ser Val
1 5 10 15

Lys Gly

<210> SEQ ID NO 81
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 81

Ala Arg Trp Arg Ser Leu Ser Ser Gly Met Asp Tyr
1 5 10

<210> SEQ ID NO 82
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 82

Arg Ala Ser Gln Asp Val Ser Thr Ala Val Ala
1 5 10

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 83

Ser Ala Ser Phe Leu Tyr Ser
1 5

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 84

Gln Gln Ala Lys Thr Thr Pro Pro Thr
1 5

<210> SEQ ID NO 85
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 85

Gly Phe Thr Phe Thr Gly Thr Gly Ile His
1 5 10

<210> SEQ ID NO 86
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 86

Ala Gly Ile Ser Pro Ala Gly Gly Tyr Thr Tyr Tyr Ala Asp Ser Val
1 5 10 15

Lys Gly

<210> SEQ ID NO 87
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 87

Ala Arg Trp Arg Ser Leu Ser Ser Gly Met Asp Tyr
1 5 10

<210> SEQ ID NO 88
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 88

Arg Ala Ser Gln Ile Ile Gly Ile Ser Leu Ala
1 5 10

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 89

Ala Ala Ser Asn Leu Ala Ser
1 5

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 90

Gln Gln Ser Tyr Ser Thr Pro Leu Thr
1 5

<210> SEQ ID NO 91
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 91

Gly Phe Thr Phe Thr Gly Thr Gly Ile His
1 5 10

<210> SEQ ID NO 92
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 92

Ala Gly Ile Ser Pro Ala Gly Gly Tyr Thr Tyr Tyr Ala Asp Ser Val
1 5 10 15

Lys Gly

<210> SEQ ID NO 93
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 93

Ala Arg Trp Arg Ser Leu Ser Ser Gly Met Asp Tyr
1 5 10

<210> SEQ ID NO 94
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 94

Arg Ala Ser Gln Ser Ile Arg Asn Ser Leu Ala
1 5 10

<210> SEQ ID NO 95
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 95

Val Ala Ser Ser Leu Ala Ser
1 5

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 96

Gln Gln Ser Tyr Ser Thr Pro Leu Thr
1 5

<210> SEQ ID NO 97
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 97

Gly Phe Thr Phe Thr Gly Thr Gly Ile His
1 5 10

<210> SEQ ID NO 98
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 98

Ala Gly Ile Ser Pro Ala Gly Gly Tyr Thr Tyr Tyr Ala Asp Ser Val
1 5 10 15

Lys Gly

<210> SEQ ID NO 99
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 99

Ala Arg Trp Arg Ser Leu Ser Ser Gly Met Asp Tyr
1 5 10

<210> SEQ ID NO 100
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 100

Arg Ala Ser Gln Ile Ile Gly Arg Ser Leu Ala
1 5 10

<210> SEQ ID NO 101
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 101

Val Ala Ser Asn Leu Ala Ser
1 5

<210> SEQ ID NO 102
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 102

Gln Gln Ser Asn Ala Thr Pro Pro Thr
1 5

<210> SEQ ID NO 103
<211> LENGTH: 121
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 103

Glu Val Gln Leu Val Glu Ser Gly Gly Gly Leu Val Gln Pro Gly Gly
1 5 10 15

Ser Leu Arg Leu Ser Cys Ala Ala Ser Gly Phe Ser Leu Ser Gly Ser
20 25 30

Trp Ile His Trp Val Arg Gln Ala Pro Gly Lys Gly Leu Glu Trp Val
35 40 45

Gly Trp Ile Asn Pro Tyr Arg Gly Tyr Ala Tyr Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ala Arg Glu Tyr Ser Gly Trp Gly Gly Ser Ser Val Gly Tyr Ala Met
100 105 110

Asp Tyr Trp Gly Gln Gly Thr Leu Val
115 120

<210> SEQ ID NO 104
<211> LENGTH: 108
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 104

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Val Ser Thr Ala
20 25 30

Val Ala Trp Tyr Gln Gln Lys Pro Gly Lys Ala Pro Lys Leu Leu Ile
35 40 45

Tyr Ser Ala Ser Phe Leu Tyr Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Tyr Thr Thr Pro Pro
85 90 95

Thr Phe Gly Gln Gly Thr Lys Val Glu Ile Lys Arg
100 105

<210> SEQ ID NO 105
<211> LENGTH: 121
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 105

Glu Val Gln Leu Val Glu Ser Gly Gly Gly Leu Val Gln Pro Gly Gly
1 5 10 15

```
Ser Leu Arg Leu Ser Cys Ala Ala Ser Gly Phe Ser Phe Thr Gly Thr
            20                  25                  30

Trp Ile His Trp Val Arg Gln Ala Pro Gly Lys Gly Leu Glu Trp Val
        35                  40                  45

Gly Trp Ile Ala Pro Tyr Ser Arg His Pro Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Tyr Ser Gly Trp Gly Gly Ser Ser Val Gly Tyr Ala Met
            100                 105                 110

Asp Tyr Trp Gly Gln Gly Thr Leu Val
        115                 120


<210> SEQ ID NO 106
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys Arg
            100                 105


<210> SEQ ID NO 107
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Gly Thr
            20                  25                  30

Gly Ile His Trp Val Arg Gln Ala Pro Gly Lys Gly Leu Glu Trp Val
        35                  40                  45

Ala Gly Ile Pro Pro Val Gly Ser Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80
```

```
Leu Gln Met Asn Ser Leu Arg Ala Glu Asp Thr Ala Val Tyr Tyr Cys
                85                  90                  95

Ala Arg Trp Arg Ser Leu Ser Ser Gly Met Asp Tyr Trp Gly Gln Gly
            100                 105                 110

Thr Leu Val
        115


<210> SEQ ID NO 108
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Lys Thr Thr Pro Pro
                85                  90                  95

Thr Phe Gly Gln Gly Thr Lys Val Glu Ile Lys Arg
            100                 105


<210> SEQ ID NO 109
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Thr Ser Ile
            20                  25                  30

Gly Ile His Trp Val Arg Gln Ala Pro Gly Lys Gly Leu Glu Trp Val
        35                  40                  45

Ala Gly Ile Pro Pro Val Gly Arg Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Trp Arg Ser Leu Ser Ser Gly Met Asp Tyr Trp Gly Gln Gly
            100                 105                 110

Thr Leu Val
        115


<210> SEQ ID NO 110
```

<211> LENGTH: 108
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 110

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Val Ser Thr Ala
20 25 30

Val Ala Trp Tyr Gln Gln Lys Pro Gly Lys Ala Pro Lys Leu Leu Ile
35 40 45

Tyr Ser Ala Ser Phe Leu Tyr Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Tyr Met Ser Pro Leu
85 90 95

Thr Phe Gly Gln Gly Thr Lys Val Glu Ile Lys Arg
100 105

<210> SEQ ID NO 111
<211> LENGTH: 134
<212> TYPE: PRT
<213> ORGANISM: Homo sapiens

<400> SEQUENCE: 111

Met Ala Trp Arg Cys Pro Arg Met Gly Arg Val Pro Leu Ala Trp Cys
1 5 10 15

Leu Ala Leu Cys Gly Trp Ala Cys Met Ala Pro Arg Gly Thr Gln Ala
20 25 30

Glu Glu Ser Pro Phe Val Gly Asn Pro Gly Asn Ile Thr Gly Ala Arg
35 40 45

Gly Leu Thr Gly Thr Leu Arg Cys Gln Leu Gln Val Gln Gly Glu Pro
50 55 60

Pro Glu Val His Trp Leu Arg Asp Gly Gln Ile Leu Glu Leu Ala Asp
65 70 75 80

Ser Thr Gln Thr Gln Val Pro Leu Gly Glu Asp Glu Gln Asp Asp Trp
85 90 95

Ile Val Val Ser Gln Leu Arg Ile Thr Ser Leu Gln Leu Ser Asp Thr
100 105 110

Gly Gln Tyr Gln Cys Leu Val Phe Leu Gly His Gln Thr Phe Val Ser
115 120 125

Gln Pro Gly Tyr Val Gly
130

<210> SEQ ID NO 112
<211> LENGTH: 10
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (3)..(3)
<223> OTHER INFORMATION: Ser or Thr
<220> FEATURE:
<221> NAME/KEY: MOD_RES <222> LOCATION: (4)..(4)
<223> OTHER INFORMATION: Leu, Phe or Val
<220> FEATURE:
<221> NAME/KEY: MOD_RES
<222> LOCATION: (5)..(5)
<223> OTHER INFORMATION: Ser, Thr or Arg
<220> FEATURE:
<221> NAME/KEY: MOD_RES
<222> LOCATION: (6)..(6)
<223> OTHER INFORMATION: Gly or Ser
<220> FEATURE:
<221> NAME/KEY: MOD_RES
<222> LOCATION: (7)..(7)
<223> OTHER INFORMATION: Ser, His, Thr or Ile
<220> FEATURE:
<221> NAME/KEY: MOD_RES
<222> LOCATION: (8)..(8)
<223> OTHER INFORMATION: Trp or Gly
<220> FEATURE:
<221> NAME/KEY: MOD_RES
<222> LOCATION: (9)..(9)
<223> OTHER INFORMATION: Ile or Leu

<400> SEQUENCE: 112

Gly Phe Xaa Xaa Xaa Xaa Xaa Xaa Xaa His
1 5 10

<210> SEQ ID NO 113
<211> LENGTH: 18
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (1)..(1)
<223> OTHER INFORMATION: Gly or Ala
<220> FEATURE:
<221> NAME/KEY: MOD_RES
<222> LOCATION: (2)..(2)
<223> OTHER INFORMATION: Trp or Gly
<220> FEATURE:
<221> NAME/KEY: MOD_RES
<222> LOCATION: (4)..(4)
<223> OTHER INFORMATION: Asn, Ser, Ala or Pro
<220> FEATURE:
<221> NAME/KEY: MOD_RES
<222> LOCATION: (6)..(6)
<223> OTHER INFORMATION: Tyr, Ala or Val
<220> FEATURE:
<221> NAME/KEY: MOD_RES
<222> LOCATION: (7)..(8)
<223> OTHER INFORMATION: Arg, Gly or Ser
<220> FEATURE:
<221> NAME/KEY: MOD_RES
<222> LOCATION: (9)..(9)
<223> OTHER INFORMATION: Tyr, Ser or His
<220> FEATURE:
<221> NAME/KEY: MOD_RES
<222> LOCATION: (10)..(10)
<223> OTHER INFORMATION: Ala, Thr or Pro

<400> SEQUENCE: 113

Xaa Xaa Ile Xaa Pro Xaa Xaa Xaa Xaa Xaa Tyr Tyr Ala Asp Ser Val
1 5 10 15

Lys Gly

<210> SEQ ID NO 114
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)..(3)
<223> OTHER INFORMATION: Glu or Trp
<220> FEATURE:
<221> NAME/KEY: MOD_RES
<222> LOCATION: (4)..(4)
<223> OTHER INFORMATION: Tyr or Arg
<220> FEATURE:
<221> NAME/KEY: MOD_RES
<222> LOCATION: (5)..(5)
<223> OTHER INFORMATION: Ser, Asn or Pro
<220> FEATURE:
<221> NAME/KEY: MOD_RES
<222> LOCATION: (6)..(6)
<223> OTHER INFORMATION: Gly, Asp or Leu
<220> FEATURE:
<221> NAME/KEY: MOD_RES
<222> LOCATION: (7)..(7)
<223> OTHER INFORMATION: Trp or Ser
<220> FEATURE:
<221> NAME/KEY: MOD_RES
<222> LOCATION: (8)..(8)
<223> OTHER INFORMATION: Gly, Arg, Ala or Ser
<220> FEATURE:
<221> NAME/KEY: MOD_RES
<222> LOCATION: (9)..(9)
<223> OTHER INFORMATION: Gly or Ser
<220> FEATURE:
<221> NAME/KEY: MOD_RES
<222> LOCATION: (10)..(10)
<223> OTHER INFORMATION: Ser or absent
<220> FEATURE:
<221> NAME/KEY: MOD_RES
<222> LOCATION: (11)..(11)
<223> OTHER INFORMATION: Ser, Tyr or absent
<220> FEATURE:
<221> NAME/KEY: MOD_RES
<222> LOCATION: (12)..(12)
<223> OTHER INFORMATION: Val, Ile or absent
<220> FEATURE:
<221> NAME/KEY: MOD_RES
<222> LOCATION: (13)..(13)
<223> OTHER INFORMATION: Gly or absent
<220> FEATURE:
<221> NAME/KEY: MOD_RES
<222> LOCATION: (14)..(14)
<223> OTHER INFORMATION: Tyr or absent
<220> FEATURE:
<221> NAME/KEY: MOD_RES
<222> LOCATION: (15)..(15)
<223> OTHER INFORMATION: Ala, Glu or absent

<400> SEQUENCE: 114

Ala Arg Xaa Xaa Xaa Xaa Xaa Xaa Xaa Xaa Xaa Xaa Xaa Xaa Xaa Met
1 5 10 15

Asp Tyr

<210> SEQ ID NO 115
<211> LENGTH: 11
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (5)..(5)
<223> OTHER INFORMATION: Asp, Ile or Ser
<220> FEATURE:
<221> NAME/KEY: MOD_RES
<222> LOCATION: (6)..(6)
<223> OTHER INFORMATION: Val or Ile
<220> FEATURE:
<221> NAME/KEY: MOD_RES <222> LOCATION: (7)..(7)
<223> OTHER INFORMATION: Ser, Gly or Arg
<220> FEATURE:
<221> NAME/KEY: MOD_RES
<222> LOCATION: (8)..(8)
<223> OTHER INFORMATION: Thr, Ile, Asn or Arg
<220> FEATURE:
<221> NAME/KEY: MOD_RES
<222> LOCATION: (9)..(9)
<223> OTHER INFORMATION: Ala or Ser
<220> FEATURE:
<221> NAME/KEY: MOD_RES
<222> LOCATION: (10)..(10)
<223> OTHER INFORMATION: Val or Leu

<400> SEQUENCE: 115

Arg Ala Ser Gln Xaa Xaa Xaa Xaa Xaa Xaa Ala
1 5 10

<210> SEQ ID NO 116
<211> LENGTH: 7
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (1)..(1)
<223> OTHER INFORMATION: Ser, Ala or Val
<220> FEATURE:
<221> NAME/KEY: MOD_RES
<222> LOCATION: (4)..(4)
<223> OTHER INFORMATION: Phe, Asn or Ser
<220> FEATURE:
<221> NAME/KEY: MOD_RES
<222> LOCATION: (6)..(6)
<223> OTHER INFORMATION: Tyr or Ala

<400> SEQUENCE: 116

Xaa Ala Ser Xaa Leu Xaa Ser
1 5

<210> SEQ ID NO 117
<211> LENGTH: 9
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (3)..(3)
<223> OTHER INFORMATION: Ser or Ala
<220> FEATURE:
<221> NAME/KEY: MOD_RES
<222> LOCATION: (4)..(4)
<223> OTHER INFORMATION: Tyr, Lys or Asn
<220> FEATURE:
<221> NAME/KEY: MOD_RES
<222> LOCATION: (5)..(5)
<223> OTHER INFORMATION: Thr, Ser, Tyr, Met, Arg or Ala
<220> FEATURE:
<221> NAME/KEY: MOD_RES
<222> LOCATION: (6)..(6)
<223> OTHER INFORMATION: Thr, Asn, Ser or Phe
<220> FEATURE:
<221> NAME/KEY: MOD_RES
<222> LOCATION: (7)..(7)
<223> OTHER INFORMATION: Pro or Arg
<220> FEATURE:
<221> NAME/KEY: MOD_RES
<222> LOCATION: (8)..(8)
<223> OTHER INFORMATION: Pro, Tyr, Ser or Leu

<400> SEQUENCE: 117

Gln Gln Xaa Xaa Xaa Xaa Xaa Xaa Thr
1 5

<210> SEQ ID NO 118
<211> LENGTH: 10
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (3)..(3)
<223> OTHER INFORMATION: Thr or Ser
<220> FEATURE:
<221> NAME/KEY: MOD_RES
<222> LOCATION: (4)..(4)
<223> OTHER INFORMATION: Phe or Leu
<220> FEATURE:
<221> NAME/KEY: MOD_RES
<222> LOCATION: (5)..(5)
<223> OTHER INFORMATION: Thr or Ser
<220> FEATURE:
<221> NAME/KEY: MOD_RES
<222> LOCATION: (7)..(7)
<223> OTHER INFORMATION: His, Ser or Thr

<400> SEQUENCE: 118

Gly Phe Xaa Xaa Xaa Gly Xaa Trp Ile His
1 5 10

<210> SEQ ID NO 119
<211> LENGTH: 18
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (4)..(4)
<223> OTHER INFORMATION: Ser, Asn or Ala
<220> FEATURE:
<221> NAME/KEY: MOD_RES
<222> LOCATION: (7)..(7)
<223> OTHER INFORMATION: Gly, Arg or Ser
<220> FEATURE:
<221> NAME/KEY: MOD_RES
<222> LOCATION: (8)..(8)
<223> OTHER INFORMATION: Gly or Arg
<220> FEATURE:
<221> NAME/KEY: MOD_RES
<222> LOCATION: (9)..(9)
<223> OTHER INFORMATION: Ser, Tyr or His
<220> FEATURE:
<221> NAME/KEY: MOD_RES
<222> LOCATION: (10)..(10)
<223> OTHER INFORMATION: Thr, Ala or Pro

<400> SEQUENCE: 119

Gly Trp Ile Xaa Pro Tyr Xaa Xaa Xaa Xaa Tyr Tyr Ala Asp Ser Val
1 5 10 15

Lys Gly

<210> SEQ ID NO 120
<211> LENGTH: 18
<212> TYPE: PRT
<213> ORGANISM: Artificial Sequence
<220> FEATURE:
<223> OTHER INFORMATION: Description of Artificial Sequence: Synthetic
peptide <220> FEATURE:
<221> NAME/KEY: MOD_RES
<222> LOCATION: (5)..(5)
<223> OTHER INFORMATION: Ser, Asn or Pro
<220> FEATURE:
<221> NAME/KEY: MOD_RES
<222> LOCATION: (6)..(6)
<223> OTHER INFORMATION: Gly or Asp
<220> FEATURE:
<221> NAME/KEY: MOD_RES
<222> LOCATION: (8)..(8)
<223> OTHER INFORMATION: Gly, Arg or Ala
<220> FEATURE:
<221> NAME/KEY: MOD_RES
<222> LOCATION: (9)..(9)
<223> OTHER INFORMATION: Gly or Ser
<220> FEATURE:
<221> NAME/KEY: MOD_RES
<222> LOCATION: (11)..(11)
<223> OTHER INFORMATION: Ser or Tyr
<220> FEATURE:
<221> NAME/KEY: MOD_RES
<222> LOCATION: (12)..(12)
<223> OTHER INFORMATION: Val or Ile
<220> FEATURE:
<221> NAME/KEY: MOD_RES
<222> LOCATION: (15)..(15)
<223> OTHER INFORMATION: Ala or Glu

<400> SEQUENCE: 120

Ala Arg Glu Tyr Xaa Xaa Trp Xaa Xaa Ser Xaa Xaa Gly Tyr Xaa Met
1 5 10 15

Asp Tyr

<210> SEQ ID NO 121
<211> LENGTH: 9
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (5)..(5)
<223> OTHER INFORMATION: Thr, Ser or Tyr
<220> FEATURE:
<221> NAME/KEY: MOD_RES
<222> LOCATION: (6)..(6)
<223> OTHER INFORMATION: Thr, Asn, Ser or Phe
<220> FEATURE:
<221> NAME/KEY: MOD_RES
<222> LOCATION: (7)..(7)
<223> OTHER INFORMATION: Pro or Arg
<220> FEATURE:
<221> NAME/KEY: MOD_RES
<222> LOCATION: (8)..(8)
<223> OTHER INFORMATION: Pro, Tyr or Ser

<400> SEQUENCE: 121

Gln Gln Ser Tyr Xaa Xaa Xaa Xaa Thr
1 5

<210> SEQ ID NO 122
<211> LENGTH: 25
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 122

Glu Val Gln Leu Val Glu Ser Gly Gly Gly Leu Val Gln Pro Gly Gly
1 5 10 15

Ser Leu Arg Leu Ser Cys Ala Ala Ser
20 25

<210> SEQ ID NO 123
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 123

Trp Val Arg Gln Ala Pro Gly Lys Gly Leu Glu Trp Val
1 5 10

<210> SEQ ID NO 124
<211> LENGTH: 30
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 124

Arg Phe Thr Ile Ser Arg Asp Asn Ser Lys Asn Thr Leu Tyr Leu Gln
1 5 10 15

Met Asn Ser Leu Arg Ala Glu Asp Thr Ala Val Tyr Tyr Cys
20 25 30

<210> SEQ ID NO 125
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 125

Trp Gly Gln Gly Thr Leu Val Thr Val Ser Ser
1 5 10

<210> SEQ ID NO 126
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 126

Asp Ile Gln Met Thr Gln Ser Pro Ser Ser Leu Ser Ala Ser Val Gly
1 5 10 15

Asp Arg Val Thr Ile Thr Cys
20

<210> SEQ ID NO 127
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 127

Trp Tyr Gln Gln Lys Pro Gly Lys Ala Pro Lys Leu Leu Ile Tyr
1 5 10 15

<210> SEQ ID NO 128
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 128

Gly Val Pro Ser Arg Phe Ser Gly Ser Gly Ser Gly Thr Asp Phe Thr
1 5 10 15

Leu Thr Ile Ser Ser Leu Gln Pro Glu Asp Phe Ala Thr Tyr Tyr Cys
20 25 30

<210> SEQ ID NO 129
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 129

Phe Gly Gln Gly Thr Lys Val Glu Ile Lys
1 5 10

<210> SEQ ID NO 130
<211> LENGTH: 104
<212> TYPE: PRT
<213> ORGANISM: Homo sapiens

<400> SEQUENCE: 130

Ile Thr Val Leu Pro Gln Gln Pro Arg Asn Leu His Leu Val Ser Arg
1 5 10 15

Gln Pro Thr Glu Leu Glu Val Ala Trp Thr Pro Gly Leu Ser Gly Ile
20 25 30

Tyr Pro Leu Thr His Cys Thr Leu Gln Ala Val Leu Ser Asp Asp Gly
35 40 45

Met Gly Ile Gln Ala Gly Glu Pro Asp Pro Pro Glu Glu Pro Leu Thr
50 55 60

Ser Gln Ala Ser Val Pro Pro His Gln Leu Arg Leu Gly Ser Leu His
65 70 75 80

Pro His Thr Pro Tyr His Ile Arg Val Ala Cys Thr Ser Ser Gln Gly
85 90 95

Pro Ser Ser Trp Thr His Trp Leu
100

<210> SEQ ID NO 131
<211> LENGTH: 30
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 131

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr
20 25 30

<210> SEQ ID NO 132
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 132

Trp Val Arg Gln Ala Pro Gly Gln Gly Leu Glu Trp Met Gly
1 5 10

<210> SEQ ID NO 133
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 133

Arg Val Thr Ile Thr Ala Asp Thr Ser Thr Ser Thr Ala Tyr Met Glu
1 5 10 15

Leu Ser Ser Leu Arg Ser Glu Asp Thr Ala Val Tyr Tyr Cys Ala Arg
20 25 30

<210> SEQ ID NO 134
<211> LENGTH: 25
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 134

Gln Val Gln Leu Val Gln Ser Gly Ala Glu Val Lys Lys Pro Gly Ala
1 5 10 15

Ser Val Lys Val Ser Cys Lys Ala Ser
20 25

<210> SEQ ID NO 135
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 135

Trp Val Arg Gln Ala Pro Gly Gln Gly Leu Glu Trp Met
1 5 10

<210> SEQ ID NO 136
<211> LENGTH: 31
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 136

Arg Val Thr Ile Thr Ala Asp Thr Ser Thr Ser Thr Ala Tyr Met Glu
1 5 10 15

Leu Ser Ser Leu Arg Ser Glu Asp Thr Ala Val Tyr Tyr Cys Ala
20 25 30

<210> SEQ ID NO 137
<211> LENGTH: 30
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 137

Arg Val Thr Ile Thr Ala Asp Thr Ser Thr Ser Thr Ala Tyr Met Glu
1 5 10 15

Leu Ser Ser Leu Arg Ser Glu Asp Thr Ala Val Tyr Tyr Cys
20 25 30

<210> SEQ ID NO 138
<211> LENGTH: 30
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 138

Gln Val Gln Leu Gln Glu Ser Gly Pro Gly Leu Val Lys Pro Ser Gln
1 5 10 15

Thr Leu Ser Leu Thr Cys Thr Val Ser Gly Gly Ser Val Ser
20 25 30

<210> SEQ ID NO 139
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 139

Trp Ile Arg Gln Pro Pro Gly Lys Gly Leu Glu Trp Ile Gly
1 5 10

<210> SEQ ID NO 140
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 140

Arg Val Thr Ile Ser Val Asp Thr Ser Lys Asn Gln Phe Ser Leu Lys
1 5 10 15

Leu Ser Ser Val Thr Ala Ala Asp Thr Ala Val Tyr Tyr Cys Ala Arg
20 25 30

<210> SEQ ID NO 141
<211> LENGTH: 25
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 141

Gln Val Gln Leu Gln Glu Ser Gly Pro Gly Leu Val Lys Pro Ser Gln
1 5 10 15

Thr Leu Ser Leu Thr Cys Thr Val Ser

```
            20                  25


<210> SEQ ID NO 142
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Trp Ile Arg Gln Pro Pro Gly Lys Gly Leu Glu Trp Ile
1               5                   10


<210> SEQ ID NO 143
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala
            20                  25                  30


<210> SEQ ID NO 144
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys
            20                  25                  30


<210> SEQ ID NO 145
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30


<210> SEQ ID NO 146
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Trp Val Arg Gln Ala Pro Gly Lys Gly Leu Glu Trp Val Ser
```

1 5 10

<210> SEQ ID NO 147
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 147

Arg Phe Thr Ile Ser Arg Asp Asn Ser Lys Asn Thr Leu Tyr Leu Gln
1 5 10 15

Met Asn Ser Leu Arg Ala Glu Asp Thr Ala Val Tyr Tyr Cys Ala Arg
20 25 30

<210> SEQ ID NO 148
<211> LENGTH: 31
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 148

Arg Phe Thr Ile Ser Arg Asp Asn Ser Lys Asn Thr Leu Tyr Leu Gln
1 5 10 15

Met Asn Ser Leu Arg Ala Glu Asp Thr Ala Val Tyr Tyr Cys Ala
20 25 30

<210> SEQ ID NO 149
<211> LENGTH: 30
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 149

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys
20 25 30

<210> SEQ ID NO 150
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 150

Arg Phe Thr Ile Ser Ala Asp Thr Ser Lys Asn Thr Ala Tyr Leu Gln
1 5 10 15

Met Asn Ser Leu Arg Ala Glu Asp Thr Ala Val Tyr Tyr Cys Ser Arg
20 25 30

<210> SEQ ID NO 151
<211> LENGTH: 31
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 151

Arg Phe Thr Ile Ser Ala Asp Thr Ser Lys Asn Thr Ala Tyr Leu Gln
1 5 10 15

Met Asn Ser Leu Arg Ala Glu Asp Thr Ala Val Tyr Tyr Cys Ser
20 25 30

<210> SEQ ID NO 152
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 152

Arg Phe Thr Ile Ser Ala Asp Thr Ser Lys Asn Thr Ala Tyr Leu Gln
1 5 10 15

Met Asn Ser Leu Arg Ala Glu Asp Thr Ala Val Tyr Tyr Cys Ala Arg
20 25 30

<210> SEQ ID NO 153
<211> LENGTH: 31
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 153

Arg Phe Thr Ile Ser Ala Asp Thr Ser Lys Asn Thr Ala Tyr Leu Gln
1 5 10 15

Met Asn Ser Leu Arg Ala Glu Asp Thr Ala Val Tyr Tyr Cys Ala
20 25 30

<210> SEQ ID NO 154
<211> LENGTH: 30
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 154

Arg Phe Thr Ile Ser Ala Asp Thr Ser Lys Asn Thr Ala Tyr Leu Gln
1 5 10 15

Met Asn Ser Leu Arg Ala Glu Asp Thr Ala Val Tyr Tyr Cys
20 25 30

<210> SEQ ID NO 155
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 155

Asp Ile Val Met Thr Gln Ser Pro Leu Ser Leu Pro Val Thr Pro Gly
1 5 10 15

Glu Pro Ala Ser Ile Ser Cys
20

<210> SEQ ID NO 156
<211> LENGTH: 15

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 156

Trp Tyr Leu Gln Lys Pro Gly Gln Ser Pro Gln Leu Leu Ile Tyr
1 5 10 15

<210> SEQ ID NO 157
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 157

Gly Val Pro Asp Arg Phe Ser Gly Ser Gly Ser Gly Thr Asp Phe Thr
1 5 10 15

Leu Lys Ile Ser Arg Val Glu Ala Glu Asp Val Gly Val Tyr Tyr Cys
20 25 30

<210> SEQ ID NO 158
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 158

Glu Ile Val Leu Thr Gln Ser Pro Gly Thr Leu Ser Leu Ser Pro Gly
1 5 10 15

Glu Arg Ala Thr Leu Ser Cys
20

<210> SEQ ID NO 159
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 159

Trp Tyr Gln Gln Lys Pro Gly Gln Ala Pro Arg Leu Leu Ile Tyr
1 5 10 15

<210> SEQ ID NO 160
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 160

Gly Ile Pro Asp Arg Phe Ser Gly Ser Gly Ser Gly Thr Asp Phe Thr
1 5 10 15

Leu Thr Ile Ser Arg Leu Glu Pro Glu Asp Phe Ala Val Tyr Tyr Cys
20 25 30

<210> SEQ ID NO 161
<211> LENGTH: 23

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 161

Asp Ile Val Met Thr Gln Ser Pro Asp Ser Leu Ala Val Ser Leu Gly
1 5 10 15

Glu Arg Ala Thr Ile Asn Cys
20

<210> SEQ ID NO 162
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 162

Trp Tyr Gln Gln Lys Pro Gly Gln Pro Pro Lys Leu Leu Ile Tyr
1 5 10 15

<210> SEQ ID NO 163
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 163

Gly Val Pro Asp Arg Phe Ser Gly Ser Gly Ser Gly Thr Asp Phe Thr
1 5 10 15

Leu Thr Ile Ser Ser Leu Gln Ala Glu Asp Val Ala Val Tyr Tyr Cys
20 25 30

<210> SEQ ID NO 164
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 164

Gly Val Pro Ser Arg Phe Ser Gly Ser Arg Ser Gly Thr Asp Phe Thr
1 5 10 15

Leu Thr Ile Ser Ser Leu Gln Pro Glu Asp Phe Ala Thr Tyr Tyr Cys
20 25 30

<210> SEQ ID NO 165
<211> LENGTH: 885
<212> TYPE: PRT
<213> ORGANISM: Homo sapiens

<400> SEQUENCE: 165

Met Ala Trp Arg Cys Pro Arg Met Gly Arg Val Pro Leu Ala Trp Cys
1 5 10 15

Leu Ala Leu Cys Gly Trp Ala Cys Met Ala Pro Arg Gly Thr Gln Ala
20 25 30

Glu Glu Ser Pro Phe Val Gly Asn Pro Gly Asn Ile Thr Gly Ala Arg
35 40 45

```
Gly Leu Thr Gly Thr Leu Arg Cys Gln Leu Gln Val Gln Gly Glu Pro
    50                  55                  60

Pro Glu Val His Trp Leu Arg Asp Gly Gln Ile Leu Glu Leu Ala Asp
65                  70                  75                  80

Ser Thr Gln Thr Gln Val Pro Leu Gly Glu Asp Glu Gln Asp Asp Trp
                85                  90                  95

Ile Val Val Ser Gln Leu Arg Ile Thr Ser Leu Gln Leu Ser Asp Thr
            100                 105                 110

Gly Gln Tyr Gln Cys Leu Val Phe Leu Gly His Gln Thr Phe Val Ser
        115                 120                 125

Gln Pro Gly Tyr Val Gly Leu Glu Gly Leu Pro Tyr Phe Leu Glu Glu
    130                 135                 140

Pro Glu Asp Arg Thr Val Ala Ala Asn Thr Pro Phe Asn Leu Ser Cys
145                 150                 155                 160

Gln Ala Gln Gly Pro Pro Glu Pro Val Asp Leu Leu Trp Leu Gln Asp
                165                 170                 175

Ala Val Pro Leu Ala Thr Ala Pro Gly His Gly Pro Gln Arg Ser Leu
            180                 185                 190

His Val Pro Gly Leu Asn Lys Thr Ser Ser Phe Ser Cys Glu Ala His
        195                 200                 205

Asn Ala Lys Gly Val Thr Thr Ser Arg Thr Ala Thr Ile Thr Val Leu
    210                 215                 220

Pro Gln Gln Pro Arg Asn Leu His Leu Val Ser Arg Gln Pro Thr Glu
225                 230                 235                 240

Leu Glu Val Ala Trp Thr Pro Gly Leu Ser Gly Ile Tyr Pro Leu Thr
                245                 250                 255

His Cys Thr Leu Gln Ala Val Leu Ser Asp Asp Gly Met Gly Ile Gln
            260                 265                 270

Ala Gly Glu Pro Asp Pro Pro Glu Glu Pro Leu Thr Ser Gln Ala Ser
        275                 280                 285

Val Pro Pro His Gln Leu Arg Leu Gly Ser Leu His Pro His Thr Pro
    290                 295                 300

Tyr His Ile Arg Val Ala Cys Thr Ser Ser Gln Gly Pro Ser Ser Trp
305                 310                 315                 320

Thr His Trp Leu Pro Val Glu Thr Pro Glu Gly Val Pro Leu Gly Pro
                325                 330                 335

Pro Glu Asn Ile Ser Ala Thr Arg Asn Gly Ser Gln Ala Phe Val His
            340                 345                 350

Trp Gln Glu Pro Arg Ala Pro Leu Gln Gly Thr Leu Leu Gly Tyr Arg
        355                 360                 365

Leu Ala Tyr Gln Gly Gln Asp Thr Pro Glu Val Leu Met Asp Ile Gly
    370                 375                 380

Leu Arg Gln Glu Val Thr Leu Glu Leu Gln Gly Asp Gly Ser Val Ser
385                 390                 395                 400

Asn Leu Thr Val Cys Val Ala Ala Tyr Thr Ala Ala Gly Asp Gly Pro
                405                 410                 415

Trp Ser Leu Pro Val Pro Leu Glu Ala Trp Arg Pro Val Lys Glu Pro
            420                 425                 430

Ser Thr Pro Ala Phe Ser Trp Pro Trp Trp Tyr Val Leu Leu Gly Ala
        435                 440                 445

Val Val Ala Ala Ala Cys Val Leu Ile Leu Ala Leu Phe Leu Val His
    450                 455                 460

Arg Arg Lys Lys Glu Thr Arg Tyr Gly Glu Val Phe Glu Pro Thr Val
```

465 470 475 480

Glu Arg Gly Glu Leu Val Val Arg Tyr Arg Val Arg Lys Ser Tyr Ser
485 490 495

Arg Arg Thr Thr Glu Ala Thr Leu Asn Ser Leu Gly Ile Ser Glu Glu
500 505 510

Leu Lys Glu Lys Leu Arg Asp Val Met Val Asp Arg His Lys Val Ala
515 520 525

Leu Gly Lys Thr Leu Gly Glu Gly Glu Phe Gly Ala Val Met Glu Gly
530 535 540

Gln Leu Asn Gln Asp Asp Ser Ile Leu Lys Val Ala Val Lys Thr Met
545 550 555 560

Lys Ile Ala Ile Cys Thr Arg Ser Glu Leu Glu Asp Phe Leu Ser Glu
565 570 575

Ala Val Cys Met Lys Glu Phe Asp His Pro Asn Val Met Arg Leu Ile
580 585 590

Gly Val Cys Phe Gln Gly Ser Glu Arg Glu Ser Phe Pro Ala Pro Val
595 600 605

Val Ile Leu Pro Phe Met Lys His Gly Asp Leu His Ser Phe Leu Leu
610 615 620

Tyr Ser Arg Leu Gly Asp Gln Pro Val Tyr Leu Pro Thr Gln Met Leu
625 630 635 640

Val Lys Phe Met Ala Asp Ile Ala Ser Gly Met Glu Tyr Leu Ser Thr
645 650 655

Lys Arg Phe Ile His Arg Asp Leu Ala Ala Arg Asn Cys Met Leu Asn
660 665 670

Glu Asn Met Ser Val Cys Val Ala Asp Phe Gly Leu Ser Lys Lys Ile
675 680 685

Tyr Asn Gly Asp Tyr Tyr Arg Gln Gly Arg Ile Ala Lys Met Pro Val
690 695 700

Lys Trp Ile Ala Ile Glu Ser Leu Ala Asp Arg Val Tyr Thr Ser Lys
705 710 715 720

Ser Asp Val Trp Ser Phe Gly Val Thr Met Trp Glu Ile Ala Thr Arg
725 730 735

Gly Gln Thr Pro Tyr Pro Gly Val Glu Asn Ser Glu Ile Tyr Asp Tyr
740 745 750

Leu Arg Gln Gly Asn Arg Leu Lys Gln Pro Ala Asp Cys Leu Asp Gly
755 760 765

Leu Tyr Ala Leu Met Ser Arg Cys Trp Glu Leu Asn Pro Gln Asp Arg
770 775 780

Pro Ser Phe Thr Glu Leu Arg Glu Asp Leu Glu Asn Thr Leu Lys Ala
785 790 795 800

Leu Pro Pro Ala Gln Glu Pro Asp Glu Ile Leu Tyr Val Asn Met Asp
805 810 815

Glu Gly Gly Gly Tyr Pro Glu Pro Pro Gly Ala Ala Gly Gly Ala Asp
820 825 830

Pro Pro Thr Gln Pro Asp Pro Lys Asp Ser Cys Ser Cys Leu Thr Ala
835 840 845

Ala Glu Val His Pro Ala Gly Arg Tyr Val Leu Cys Pro Ser Thr Thr
850 855 860

Pro Ser Pro Ala Gln Pro Ala Asp Arg Gly Ser Pro Ala Ala Pro Gly
865 870 875 880

Gln Glu Asp Gly Ala
885

```
<210> SEQ ID NO 166
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gly or Ala
<220> FEATURE:
<221> NAME/KEY: MOD_RES
<222> LOCATION: (2)..(2)
<223> OTHER INFORMATION: Trp or Gly
<220> FEATURE:
<221> NAME/KEY: MOD_RES
<222> LOCATION: (4)..(4)
<223> OTHER INFORMATION: Asn, Ser, Ala or Pro
<220> FEATURE:
<221> NAME/KEY: MOD_RES
<222> LOCATION: (6)..(6)
<223> OTHER INFORMATION: Tyr, Ala or Val
<220> FEATURE:
<221> NAME/KEY: MOD_RES
<222> LOCATION: (7)..(8)
<223> OTHER INFORMATION: Arg, Gly or Ser
<220> FEATURE:
<221> NAME/KEY: MOD_RES
<222> LOCATION: (9)..(9)
<223> OTHER INFORMATION: Tyr, Ser or His
<220> FEATURE:
<221> NAME/KEY: MOD_RES
<222> LOCATION: (10)..(10)
<223> OTHER INFORMATION: Ala, Thr or Pro
<220> FEATURE:
<221> NAME/KEY: MOD_RES
<222> LOCATION: (11)..(12)
<223> OTHER INFORMATION: Any amino acid or absent

<400> SEQUENCE: 166

Xaa Xaa Ile Xaa Pro Xaa Xaa Xaa Xaa Xaa Xaa Xaa Tyr Tyr Ala Asp
1               5                   10                  15

Ser Val Lys Gly
            20
```

What is claimed is:

1. An isolated antibody that binds to human Axl, [wherein the antibody binds human Axl with an affinity of ≤600 pM, wherein the antibody binds mouse Axl with an affinity of ≤1 nM, and] wherein the antibody comprises (a) HVR-H1 comprising $GFX_1X_2X_3GX_4WIH$, wherein $X_1$ is T or S, $X_2$ is F or L, $X_3$ is T or S, $X_4$ is H, S or T (SEQ ID NO:118); (b) HVR-H2 comprising $GWIX_1PYX_2X_3X_4X_5YYADSVKG$, wherein $X_1$ is S, N or A; $X_2$ is G, R or S; $X_3$ is G or R; $X_4$ is S, Y or H; $X_5$ is T, A or P (SEQ ID NO:119); (c) HVR-H3 comprising $AREYX_1X_2WX_3X_4SX_5X_6GYX_7MDY$, wherein $X_1$ is S, N or P; $X_2$ is G or D; $X_3$ is G, R, or A; $X_4$ is G or S; $X_5$ is S or Y; $X_6$ is V or I; $X_7$ is A or E (SEQ ID NO:120); (d) HVR-L1 comprising RASQDVSTAVA (SEQ ID NO:10); (e) HVR-L2 comprising SASFLYS (SEQ ID NO:11); and (f) HVR-L3 comprising $QQSYX_1X_2X_3X_4T$, wherein $X_1$ is T, S or Y; $X_2$ is T, N, S or F; $X_3$ is P or R; $X_4$ is P, Y or S (SEQ ID NO:121).

2. The antibody of claim 1, wherein the antibody promotes Axl receptor downregulation and/or inhibits constitutive Axl activation.

3. The antibody of claim 1, wherein the antibody binds a polypeptide comprising, consisting essentially of or consisting of the following amino acid sequence: SEQ ID NO:111.

4. The antibody of claim 1, which is a monoclonal antibody.

5. The antibody of claim 1, which is a full length IgG1 antibody.

6. The antibody of claim 1, which is a human antibody, humanized antibody, chimeric antibody, or antibody fragment that binds Axl.

7. The antibody of claim 1, wherein the antibody comprises (a) HVR-H3 comprising the amino acid sequence of SEQ ID NO:9, (b) HVR-L3 comprising the amino acid sequence of SEQ ID NO:12, and (c) HVR-H2 comprising the amino acid sequence of SEQ ID NO:8.

8. The antibody of claim 1, wherein the antibody comprises (a) HVR-H1 comprising the amino acid sequence of SEQ ID NO:7, (b) HVR-H2 comprising the amino acid sequence of SEQ ID NO:8, and (c) HVR-H3 comprising the amino acid sequence of SEQ ID NO:9.

9. The antibody of claim 1, wherein the antibody comprises (a) HVR-L1 comprising the amino acid sequence of SEQ ID NO:10; (b) HVR-L2 comprising the amino acid sequence of SEQ ID NO:11; and (c) HVR-L3 comprising the amino acid sequence of SEQ ID NO:12.

10. The antibody of claim 8, wherein the antibody comprises (a) HVR-L1 comprising the amino acid sequence of SEQ ID NO:10; (b) HVR-L2 comprising the amino acid sequence of SEQ ID NO:11; and (c) HVR-L3 comprising the amino acid sequence of SEQ ID NO:12.

11. The antibody of claim 10, comprising (a) a VH sequence having at least 95% sequence identity to the amino acid sequence of SEQ ID NO:103; (b) a VL sequence having at least 95% sequence identity to the amino acid sequence of SEQ ID NO:104; or (c) a VH sequence as in (a) and a VL sequence as in (b).

12. The antibody of claim 11, comprising a VH sequence of SEQ ID NO:103 and/or a VL sequence of SEQ ID NO:104.

13. Isolated nucleic acid encoding the antibody of claim 1.

14. A host cell comprising the nucleic acid of claim 13.

15. A method of producing an antibody comprising culturing the host cell of claim 14 so that the antibody is produced.

16. The method of claim 15, further comprising recovering the antibody from the host cell.

17. An immunoconjugate comprising the antibody of claim 1 and a cytotoxic agent.

18. A pharmaceutical formulation comprising the antibody of claim 1 and a pharmaceutically acceptable carrier.

19. The pharmaceutical formulation of claim 18, further comprising an additional therapeutic agent.

20. The pharmaceutical formulation of claim 19, wherein the additional therapeutic agent is selected from a VEGF antagonist, an EGFR antagonist, and a chemotherapeutic agent.

21. The antibody of claim 1 for use in inhibiting cell proliferation, promoting Axl downregulation, inhibiting metastasis, and/or inhibiting angiogenesis.

* * * * *